United States Patent
Nakatsuji et al.

(10) Patent No.: US 12,201,655 B2
(45) Date of Patent: *Jan. 21, 2025

(54) ANTIMICROBIAL THERAPY

(71) Applicant: The Regents of the University of California, Oakland, CA (US)

(72) Inventors: Teruaki Nakatsuji, San Diego, CA (US); Richard L. Gallo, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/220,308

(22) Filed: Apr. 1, 2021

(65) Prior Publication Data
US 2021/0228652 A1 Jul. 29, 2021

Related U.S. Application Data

(60) Continuation of application No. 16/653,911, filed on Oct. 15, 2019, now Pat. No. 10,980,848, which is a division of application No. 15/570,272, filed as application No. PCT/US2016/031067 on May 5, 2016, now abandoned.

(60) Provisional application No. 62/157,248, filed on May 5, 2015, provisional application No. 62/300,274, filed on Feb. 26, 2016.

(51) Int. Cl.
| | |
|---|---|
| *A61K 35/741* | (2015.01) |
| *A61K 9/00* | (2006.01) |
| *A61K 9/06* | (2006.01) |
| *A61K 9/14* | (2006.01) |
| *A61K 35/00* | (2006.01) |
| *A61K 35/744* | (2015.01) |
| *A61K 38/16* | (2006.01) |
| *A61K 38/17* | (2006.01) |
| *A61P 17/00* | (2006.01) |
| *A61P 31/04* | (2006.01) |
| *C07K 14/31* | (2006.01) |

(52) U.S. Cl.
CPC .......... *A61K 35/741* (2013.01); *A61K 9/0014* (2013.01); *A61K 9/06* (2013.01); *A61K 9/14* (2013.01); *A61K 35/744* (2013.01); *A61K 38/164* (2013.01); *A61K 38/1729* (2013.01); *A61P 17/00* (2018.01); *A61P 31/04* (2018.01); *C07K 14/31* (2013.01); *A61K 2035/115* (2013.01)

(58) Field of Classification Search
CPC ...... C07K 14/31; A61K 38/1729; A61K 9/06; A61K 2035/115; A61K 9/14; A61K 35/744; A61K 9/0014; A61K 35/741; A61K 38/164; A61P 31/04; A61P 17/00
See application file for complete search history.

(56) References Cited

U.S. PATENT DOCUMENTS

| | | | |
|---|---|---|---|
| 5,925,556 A | | 7/1999 | Tokiwa et al. |
| 10,980,848 B2 * | | 4/2021 | Nakatsuji ............. A61K 35/744 |
| 2008/0026999 A1 | | 1/2008 | Van Der Donk et al. |
| 2009/0041727 A1 | | 2/2009 | Suzuki et al. |
| 2009/0305260 A1 | | 12/2009 | Kuribayashi et al. |
| 2010/0166708 A1 | | 7/2010 | Gallo et al. |
| 2015/0050253 A1 | | 2/2015 | Gabant |

FOREIGN PATENT DOCUMENTS

| | | |
|---|---|---|
| WO | 2011/125015 A2 | 10/2011 |
| WO | 2012/112548 A2 | 8/2012 |

OTHER PUBLICATIONS

Christensen et al., Bacterial skin commensals and their role as host guardians. Beneficial Microbes, 2014, vol. 5(2): 201-215. (Year : 2014).*
Genchi G., An overview on D-amino acids. Amino Acids, 2017, vol. 49:1521-1533. (Year: 2017).*
Williams et al., Quorum sensing between bacterial species on the skin protects against epidermal injury in atopic dermatitis. Sci. Transl. Med. 11, eaat8329, 2019, pp. 1-12. (Year: 2019).*
Excipient, 4 pages downloaded from https://en.wikipedia.org on Apr. 13, 2023 (Year: 2023).*
Nagaoka et al., Therapeutic Potential of Cathelicidin Peptide LL-37, an Antimicrobial Agent, in a Murine Sepsis Model. Int. J. Mol. Sci., 2020, vol. 21, 5973, pp. 1-16. (Year: 2020).*
Murakami et al., Cathelicidin Anti-Microbial Peptide Expression in Sweat, an Innate Defense System for the Skin. The Soc, Invest. Dermatology., 2002, vol. 119(5): 1090-1095. (Year: 2002).*
Travis et al., Bactericidal Activity of Mammalian Cathelicidin-Derived Peptides. Infn. Immun., 2000, vol. 68(5): 2748-2755. (Year: 2000).*
Zaiou et al., Antimicrobial and Protease Inhibitory Functions of the Human Cathelicidin (hCAP18/LL-37) Prosequence. The Soc, Invest. Dermatology., 2003, vol. 120(5): 810-816. (Year: 2003).*
Hasegawa, Akane, Office Action, Patent Application No. 2017-557323, Japanese Patent Office, Feb. 16, 2021.
Mendoza-Olazaran et al., "Microbiological and Molecular Characterization of *Staphylococcus hominis* Isolates from Blood", PLOS One, Apr. 2013, vol. 8, Issue 4, e61161, pp. 1-6.
Thomas, Shane, International Search Report and Written Opinion, PCT/US16/31067, Oct. 20, 2016.
Baharlou, International Preliminary Report on Patentability and Written Opinion, PCT/US2016/031067, The International Bureau of WIPO, Nov. 16, 2017.

(Continued)

*Primary Examiner* — Ganapathirama Raghu
(74) *Attorney, Agent, or Firm* — Gavrilovich, Dodd & Lindsey LLP

(57) ABSTRACT

Methods and compositions comprising hogocidin peptides (SH-lantibiotics), derivatives and variants are provided. Also provided are methods and compositions comprising probiotic compositions utilizing strains of *S. hominis* and *S. epidermidis* that produce hogocidin, hogocidin-like peptides, or other inhibitors of skin pathogens. Methods of treatment for microbial skin infections and atopic dermatitis are also provided.

20 Claims, 43 Drawing Sheets
Specification includes a Sequence Listing.

(56) References Cited

OTHER PUBLICATIONS

Cogen, Anna L. et al., "Selective Antimicrobial Action is Provided by Phenol-Soluble Modulins Derived from *Staphylococcus epidermidis*, a Normal Resident of the Skin", Journal of Investigative Dermatology, vol. 130, No. 1, Jan. 1, 2010, pp. 192-200.
Gallo, Richard L. et al., "Microbial Symbiosis with the Innate Immune Defense System of the Skin", Journal of Investigative Dermatology, vol. 131, No. 10, Oct. 1, 2011, pp. 1974-1980.
Higaki et al., "Distrubution and Antimicrobial Susceptability of Coagulase-negative *Staphylococci* from Skin Lesions," J. of Intern. Med. Res., 27:191-195, 1999.
Kloos et al., "Update on Clinical Significance of Coagulase-Negative *Staphylococci*," Clin. Microbiol. Rev., 7 (1):117-140, 1994.
Nakatsuji et al., "Dermatological Therapy by Topical Application of Non-Pathogenic Bacteria", Journal of Investigative Dermatology, vol. 134, No. 1, Jan. 1, 2014, pp. 11-14.
Winger, Rudolf, Extended European Search Report, European Patent Office, Application No. 16790119.8, Dec. 20, 2018.
Islam et al., "Antimicrobial mechanism of lantibiotics", Biochem. Soc. Trans., Dec. 2012, 1:40(6):1528-33.
Ogawa, Tomohiro, Office Action, Patent Application No. 2021-187890, Japanese Patent Office, Nov. 22, 2022.
Nakano, Ai, Office Action, Japan Patent Office, Application No. 2023-144981, Aug. 20, 2024.
Power et al., "A Naturally Occurring Novel Allele of Escherichia coli Outer Membrane Protein A Reduces Sensitivity to Bacteriophage", Applied and Environmental Microbiology, Dec. 2006, pp. 7930-7932.

\* cited by examiner

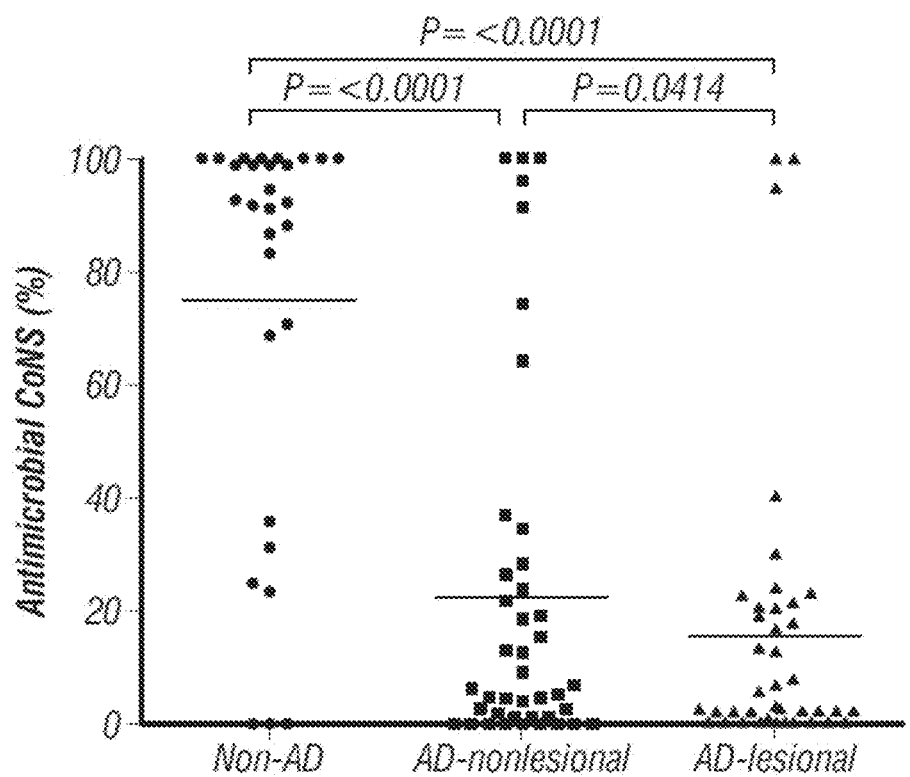
FIG. 2A
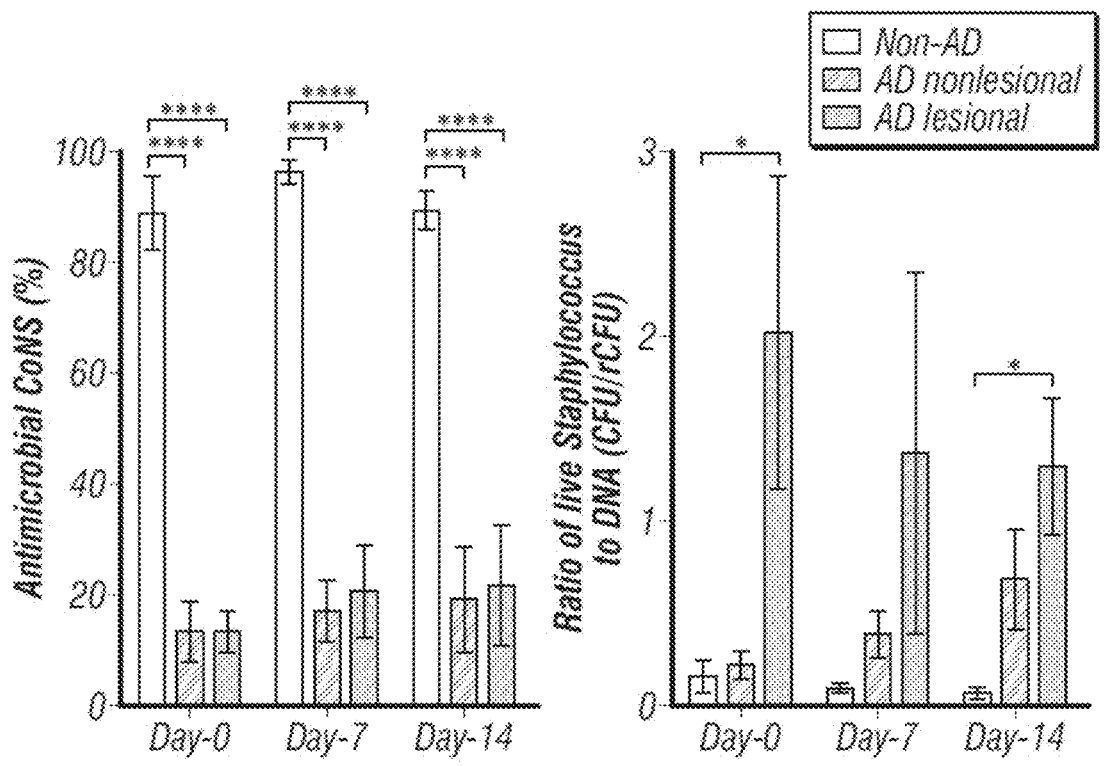
FIG. 2B
FIG. 2C

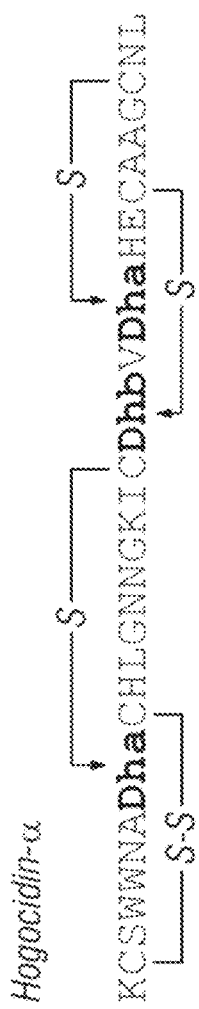
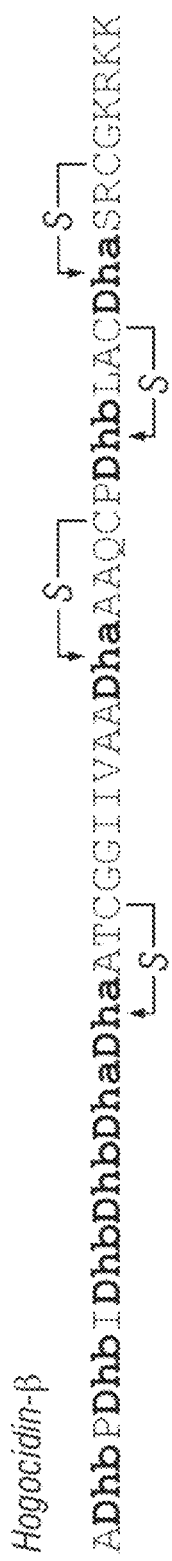
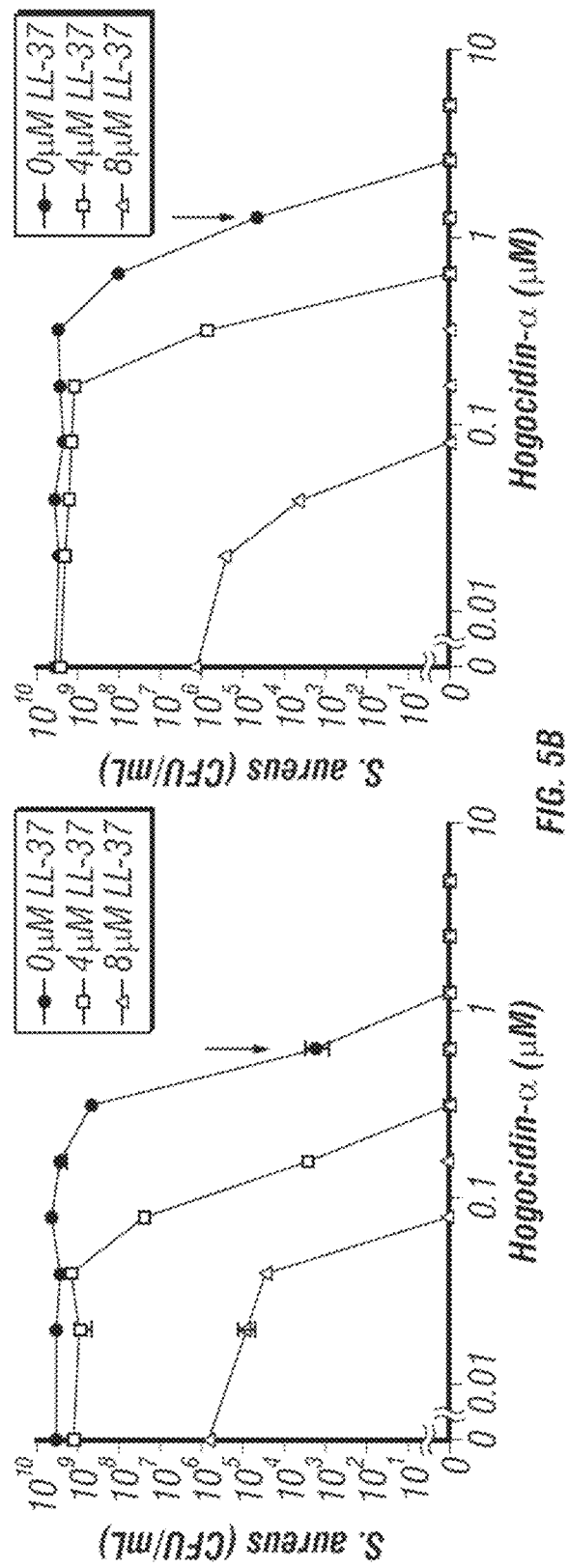
FIG. 5A
FIG. 5B

| Code | Gene | Gene Locus* | Function |
|---|---|---|---|
| $A_1$ | Hogocidin-α | 1847~2032<br>26151~26336 | Lantibiotic Precursor |
| $A_2$ | Hogocidin-β | 2050~2250<br>26354~26554 | Lantibiotic Precursor |
| C | LanC homolog | 2315~4894<br>26619~29189 | Putative lantibiotic modifying enzyme |
| T | LanT homolog | 4914~7027<br>29218~31332 | Putative lantibiotic transporter |
| M | LanM homolog | 7025~9598<br>31329~33902 | Putative lantibiotic modifying enzyme |

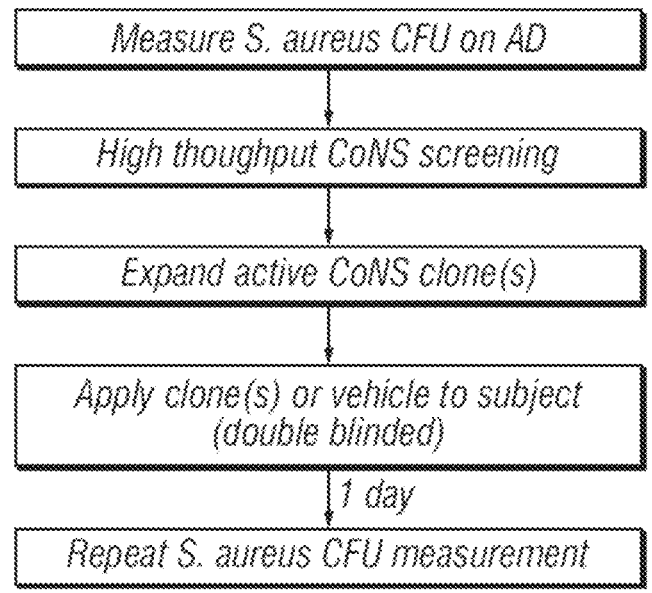

*FIG. 20C*

| Subject ID | % anti-S. aureus CoNS | Baseline S. aureus (CFU) | CoNS clones | Species | Antimicrobial class |
|---|---|---|---|---|---|
| AMT1 | 1.2 | $4.60 \times 10^6$ | AMT1-A9 | S. epidermidis | Lantibiotic |
| AMT2 | 0.6 | $6.24 \times 10^1$ | AMT2-A12 | S. hominis | Lantibiotic |
| AMT3 | 1.2 | $1.35 \times 10^6$ | AMT3-A12 | S. hominis | Lantibiotic |
| AMT4 | 15.5 | $3.35 \times 10^3$ | AMT4-C2 | S. hominis | Lantibiotic |
|  |  |  | AMT4-D12 | S. hominis | Lantibiotic |
|  |  |  | AMT4-G1 | S. hominis | Bacteriocin |
| AMT5 | 1.8 | $4.78 \times 10^1$ | AMT5-C5 | S. epidermidis | Bacteriocin |
|  |  |  | AMT5-G6 | S. epidermidis | Bacteriocin |

*FIG. 20D*

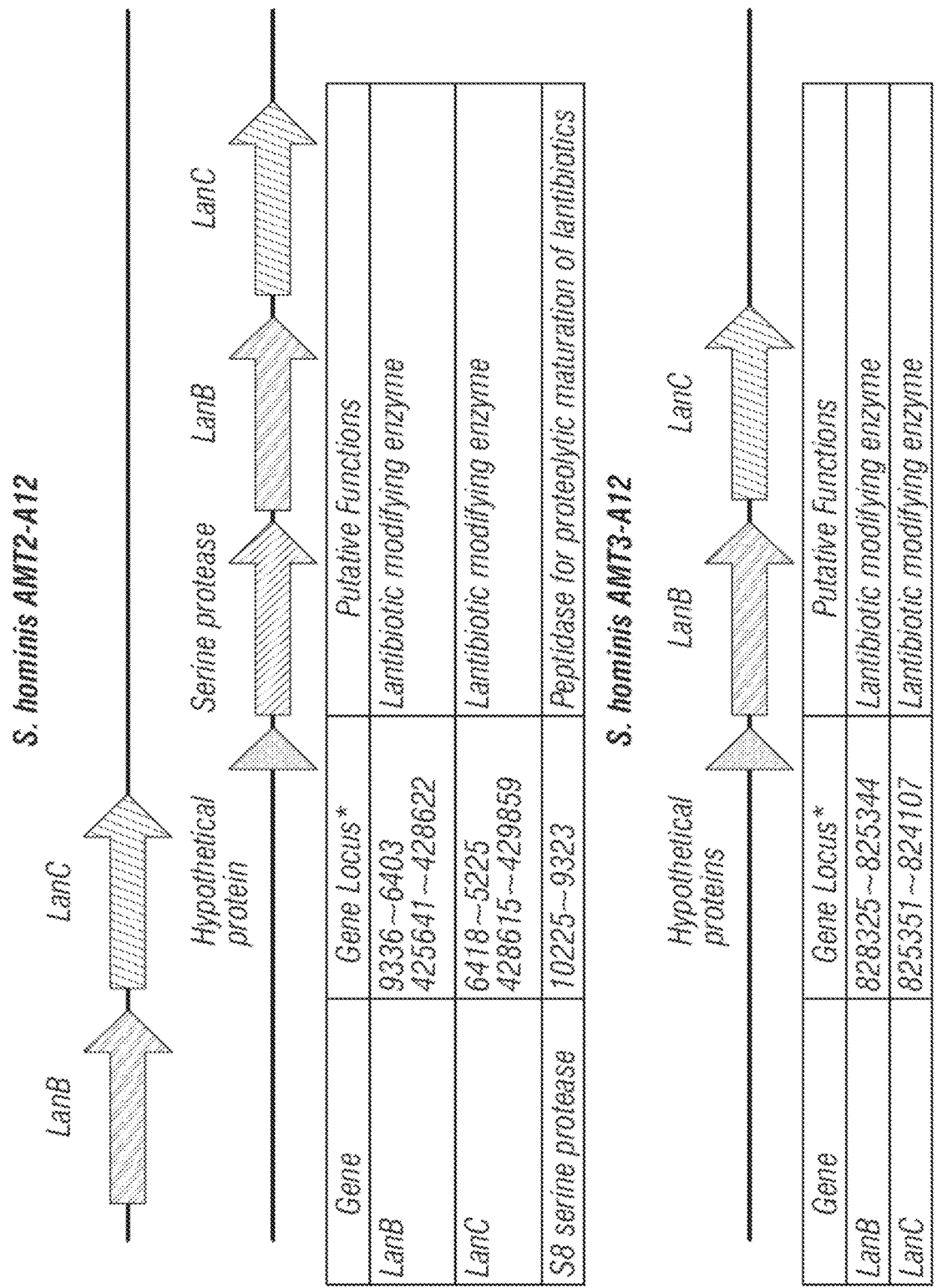

S. epidermidis AMT5-C5

S. epidermidis AMT5-G6

ANTIMICROBIAL THERAPY

CROSS REFERENCE TO RELATED APPLICATIONS

This application is a continuation of U.S. application Ser. No. 16/653,911, filed Oct. 15, 2019, which is a divisional of U.S. application Ser. No. 15/570,272, filed Oct. 27, 2017, which application is a U.S. National Stage Application filed under 35 U.S.C. § 371 and claims priority to International Application No. PCT/US2016/031067, filed May 5, 2016, which application claims priority under 35 U.S.C. § 119 from Provisional Application Ser. No. 62/157,248, filed May 5, 2015, and Provisional Application Ser. No. 62/300,274, filed Feb. 26, 2016, the disclosures of which are incorporated herein by reference.

STATEMENT REGARDING FEDERALLY SPONSORED R&D

This invention was made with government support under AI083358, AR067547 and HHSN272201000020C, awarded by the National Institutes of Health. The government has certain rights in the invention.

REFERENCE TO SEQUENCE LISTING

The present application includes a Sequence Listing in electronic format. The Sequence Listing is provided as a file entitled Sequence ST25.txt, created Apr. 13, 2022, which is 46,944 bytes in size. The information in the electronic format of the Sequence Listing is incorporated herein by reference in its entirety.

FIELD OF THE INVENTION

The disclosure relates to methods and compositions for treating infection, and modulating skin and mucosal microflora to treat diseases or disorders that are related to or exacerbated by dysbiosis.

BACKGROUND

Small, cationic antimicrobial peptides (AMPs) are naturally occurring antibiotics of the innate immune system. AMPs are widely distributed in animals and plants and are among the most ancient host defense factors. Their spectrum of activity includes Gram-positive and Gram-negative bacteria as well as fungi and certain infective agents. As resistance of pathogenic microbes to conventional antibiotics increases, researchers are exploring these endogenous antibiotics as a potential source or new therapies against variety of infectious diseases.

Patients with atopic dermatitis (AD) have recurrent skin infections by *Staphylococcus aureus* (SA) and dysbiosis of their cutaneous microbiome. The increased susceptibility to SA has been associated with diminished innate immune defense including abnormal barrier function and decreased induction of antimicrobial peptides (AMPs) such as cathelicidin and β-defensins.

Symptoms of atopic dermatitis, also referred to as eczema or atopic eczema include: dry skin that forms a rash; scaly, swollen, and red skin; rash on the face, or inside the knees, elbows, or wrists; blisters that ooze; changes in skin color after repeated episodes; thickened, cracked, dry, scaly skin or skin that looks leathery in patches; and severe itchiness (pruritis), especially at night, along with raw, sensitive, swollen skin from scratching. Atopic dermatitis (eczema) signs and symptoms vary widely from person to person and may further include: red to brownish-gray patches, especially on the hands, feet, ankles, wrists, neck, upper chest, eyelids, inside the bend of the elbows and knees, and, in infants, the face, scalp, back of the head, ears, legs, feet, arms, hands and buttocks; small, raised bumps, which may leak fluid and crust over when scratched. Atopic dermatitis most often begins before age 5 and may persist into adolescence and adulthood. For some people, it flares periodically and then clears up for a time, even for several years. The skin changes brought about by atopic dermatitis can facilitate high susceptibility of these patients to colonization and infections by *Staphylococcus aureus*.

Dysbiosis comprises an imbalance in the cutaneous or mucosal flora, including the nasal, oral, ophthalmic, urogenital, intestinal flora, wherein species such as *S. aureus* become overrepresented and other species become underrepresented. Generally, in a healthy flora, nonpathogenic bacteria may secrete inhibitors or simply occupy all available niches, thus either directly inhibiting or indirectly excluding pathogens that would otherwise be able to establish infectious states or foster the development of disease or disease-like states, such as atopic dermatitis.

SUMMARY

The disclosure provides compositions and methods for the treatment of disorders related to dysbiosis of the skin. These disorders, associated with imbalances in the normal skin flora and overgrowth of skin pathogens such as *S. aureus*, result in skin infections, atopic dermatitis, and psoriasis, among other conditions. The disclosure provides compositions and methods for treating these disorders by restoring the healthy cutaneous flora utilizing antimicrobial peptides derived from residents of the healthy cutaneous flora, or by directly administering probiotic compositions containing strains that are derived from a healthy cutaneous flora, or as the rare surviving florae cultured from the skin of diagnosed patients with a floral dysbiosis, and that are capable of either killing or inhibiting the growth of pathogenic species on the skin or species associated with a disease-like microbial imbalance.

Specifically, the disclosure provides a thickened topical composition comprising one or more probiotic bacterial strains, preferably of the genus *Staphylococcus*, and more preferably comprising the disclosed strains of *Staphylococcus hominis* and *Staphylococcus epidermidis*. These strains can be isolated from healthy cutaneous florae, or as the surviving florae cultured from the skin of diagnosed patients with a floral dysbiosis, by the methods disclosed herein, and may be identified by the secreted peptide sequences, fatty acid methyl ester profiles, and/or antimicrobial peptide codon organizations disclosed herein. The probiotic strains of the disclosure may be provided in live form, in freeze-dried form, or in a reconstitutable form. The disclosure further provides a composition comprising strains of *Staphylococcus epidermidis* and *Staphylococcus hominis* as described herein which may be formulated for topical administration to the skin, scalp, or mucosae. The disclosure further provides a composition wherein the probiotic bacterial strains comprise one or more of *S. epidermidis* strains *Staphylococcus epidermidis* strains MO34, MO38, A11, AMT1, AMT5-C5, and/or AMT5-G6 and/or *Staphylococcus hominis* strains A9, C2, AMT2, AMT3, AMT4-C2, AMT4-G1, and/or AMT4-D12.

The compositions of the disclosure may also comprise conditioned culture medium, or isolated antimicrobial compounds derived from the strains described herein, such as the peptides designated here as Hogocidins. The disclosure contemplates the use of heterologously expressed or synthetic hogocidins, hogocidin derivatives, or hogocidin-like peptides. The disclosure also provides a composition comprising a hogocidin peptide, derivative or variant and a cathelicidin peptide, derivative or variant. The disclosure further provides a composition of any of the foregoing embodiments, wherein the peptide comprises one or more D-amino acids, one or more non-naturally occurring amino acids, and/or one or more post-translational modifications. The disclosure provides a composition of any of the foregoing embodiments, wherein the peptide is substantially purified from other peptides. The disclosure provides a composition of any of the foregoing embodiments, wherein the peptide is partially purified from other peptides. The disclosure provides a composition wherein the peptide is present in a crude extract. The disclosure provides a composition of any of the foregoing embodiments in a formulation for topical administration.

The disclosure provides a composition of any of the foregoing embodiments, wherein the formulation comprises a lotion, ointment or spray or cream or oil suspension, but not limited to these formats.

The disclosure provides a composition of any of the foregoing embodiments, wherein the hogocidin peptide, derivative or variant comprises a sequence selected from SEQ ID NO:2, SEQ ID NO:4, SEQ ID NO:2 or 4 comprising a non-natural amino acid, SEQ ID NO:2 or 4 comprising a D-amino acid, or SEQ ID NO:2 or 4 comprising a fusion construct.

The disclosure also provides a method for inhibiting the spread and/or reducing the risk of infection with a microbe comprising contacting the microbe with an effective amount of a composition of the disclosure. In one embodiment, the contacting is in vivo. In another embodiment, the contacting in vivo is by topical administration. The disclosure further provides a method of treating skin or mucosal infections, atopic dermatitis, psoriasis, acne, or other disorders related to skin dysbiosis by applying to the skin or mucosa an effective amount of the compositions disclosed herein to a subject in need thereof.

The disclosure provides a method of treating atopic dermatitis comprising contacting a subject having or suspected of having atopic dermatitis with an effective amount of a probiotic composition comprising one or more of the bacterial strains disclosed herein.

The disclosure provides a method of treating atopic dermatitis comprising contacting a subject having or suspected of having atopic dermatitis with an effective amount of a hogocidin peptide, derivative or variant.

The disclosure provides a method of treating atopic dermatitis or dysbiosis of the skin by contacting the affected area with a composition comprising bacterial strains that secrete hogocidin, firmocidin, SH-lantibiotic peptide, SH-antimicrobial, SE-lantibiotic peptide, or SE antimicrobial such as *Staphylococcus hominis* strain A9, *Staphylococcus hominis* strain C2, *Staphylococcus hominis* strain AMT2, *Staphylococcus hominis* strain AMT3, *Staphylococcus hominis* strain AMT4-C2, *Staphylococcus hominis* strain AMT4-G1, *Staphylococcus hominis* strain AMT4-D12, *Staphylococcus epidermidis* strain AMT1, *Staphylococcus epidermidis* strain SE-A11, *Staphylococcus epidermidis* strain AMT5-C5, and *Staphylococcus epidermidis* strain AMT5-G6. The disclosure provides methods and compositions as described above which further comprise a cathelicidin peptide.

The disclosure provides a composition comprising a thickened topical formulation of one or more probiotic bacterial strains and optionally, a prebiotic compound, a protectant, humectant, emollient, abrasive, salt, and/or surfactant; wherein the one or more probiotic bacterial strain comprises one or more bacterial strains of the genus *Staphylococcus*; and wherein the composition is formulated for the topical treatment of disorders of dysbiosis of the skin, scalp, or mucosae. In one embodiment, the one or more probiotic bacterial strain comprises *Staphylococcus epidermidis*, *Staphylococcus hominis* or a combination of *Staphylococcus epidermidis* and *Staphylococcus hominis*. In a further embodiment, the one or more probiotic bacterial strain comprises *Staphylococcus epidermidis* strains MO34, MO38, A11, AMT1, AMT5-C5, and/or AMT5-G6. In another embodiment, one or more probiotic bacterial strains comprises *Staphylococcus hominis* strains A9, C2, AMT2, AMT3, AMT4-C2, AMT4-G1, and/or AMT4-D12. In yet another embodiment, each probiotic bacterial strain demonstrates a Fatty Acid Methyl Ester profile corresponding to one of those shown in any of FIG. 11, 12, 13, 14, 15, 16, 17, 18, or 19. In another embodiment, the one or more probiotic bacterial strains produces a peptide having a sequence selected from the group consisting of SEQ ID NO: 2, 4, 28, 30, 32, 34, 36, 38, 40, 42, 44, 46, 48, 50, 52, 54, and 55 and any combination thereof and wherein such peptide is optionally post-translationally modified. In another embodiment, the one or more probiotic bacterial strains is provided in a live form. In still another embodiment, the one or more probiotic bacterial strains is provided in a lyophilized or freeze-dried or spray dried form. In a further embodiment, the probiotic bacterium can be reconstituted into a live form.

The disclosure also provides a method of treating skin or mucosal infections, atopic dermatitis, psoriasis, mastitis, acne, or other disorders related to skin dysbiosis in humans or other mammals by applying to the skin or mucosa an effective amount of a composition as described herein and in the preceding paragraph. In one embodiment, the composition is applied topically. In a further embodiment, the composition is formulated as a cream, ointment, unguent, spray, powder, oil, thickened formulation or poultice.

The disclosure also provides a composition comprising one or more of a hogocidin peptide, derivative or variant, an SH-lantibiotic peptide, an SH-antimicrobial, an SE-lantibiotic peptide, and/or an SE antimicrobial; and further comprising one or more thickeners, solvents, emulsifiers, or pharmaceutically acceptable carriers or excipients. In one embodiment, the composition further comprises a cathelicidin peptide, derivative or variant. In yet a further or alternate embodiment, the hogocidin peptide, derivative or variant, the SH-lantibiotic peptide, and/or the SE-lantibiotic peptide comprises one or more D-amino acids or non-naturally occurring amino acids. In yet a further embodiment, the hogocidin peptide, SH-lantibiotic peptide, SH-antimicrobial, SE-lantibiotic peptide, or SE antimicrobial is produced in situ by one or more of *Staphylococcus hominis* strain A9, *Staphylococcus hominis* strain C2, *Staphylococcus hominis* strain AMT2, *Staphylococcus hominis* strain AMT3, *Staphylococcus hominis* strain AMT4-C2, *Staphylococcus hominis* strain AMT4-G1, *Staphylococcus hominis* strain AMT4-D12, *Staphylococcus epidermidis* strain AMT1, *Staphylococcus epidermidis* strain SE-A11, *Staphylococcus epidermidis* strain AMT5-05, *Staphylococcus epidermidis* strain AMT5-G6 and *Staphylococcus epidermidis* strain MO34. In yet another embodiment of any of the foregoing, the peptide is formulated for topical administration. In yet a further embodiment, the formulation comprises a lotion, ointment cream, powder, unguent, oil, or spray. In another embodiment of any of the foregoing the hogocidin peptide, derivative or variant comprises a sequence selected from SEQ ID NO:2 or SEQ ID NO:4 or an active fragment thereof having antimicrobial activity (e.g., a mature form). In yet another embodiment, the one or more of a hogocidin peptide, derivative or variant, an SH-lantibiotic peptide, an SH-antimicrobial, an SE-lantibiotic peptide, an SE antimicrobial, and a cathelicidin peptide, derivative or variant is provided as an extract or lysate of Staphylococcus hominis strain A9, Staphylococcus hominis strain C2, Staphylococcus hominis strain AMT2, Staphylococcus hominis strain AMT3, Staphylococcus hominis strain AMT4-C2, Staphylococcus hominis strain AMT4-G1, Staphylococcus hominis strain AMT4-D12, Staphylococcus epidermidis strain AMT1, Staphylococcus epidermidis strain SE-A11, Staphylococcus epidermidis strain AMT5-05, Staphylococcus epidermidis strain AMT5-G6 and Staphylococcus epidermidis strain MO34.

The disclosure also provides a method for treating skin or mucosal infection or atopic dermatitis in a subject comprising contacting the subject with an effective amount of a composition comprising one or more of a hogocidin peptide, derivative or variant, an SH-lantibiotic peptide, an SH-antimicrobial, an SE-lantibiotic peptide, and optionally, a cathelicidin peptide, derivative or variant. In one embodiment, the contacting is by topical administration or optionally by contacting the subject with one or more of SH-lantibiotic or bacteriocin-producing Staphylococcus hominis strains A9, C2, AMT2, AMT3, AMT4-C2, AMT4-G1, AMT4-D12 and Staphylococcus epidermidis strains AMT5-G6 and MO34.

The disclosure also provides a recombinant vector comprising a polynucleotide encoding a polypeptide that is at least 95% identical to SEQ ID NO:2 or 4, or a biologically active fragment thereof having antimicrobial activity. In one embodiment, the vector comprises a polynucleotide that encodes a polypeptide of SEQ ID NO:2 or 4. In yet another embodiment, the vector comprises a polynucleotides that encodes a polypeptide of SEQ ID NO:2 from about amino acid 32 to about amino acid 61. In a further embodiment, the vector comprises a polynucleotide that encodes a polypeptide of SEQ ID NO:4 from about amino acid 29 to about amino acid 66. In another embodiment, the vector comprises a polynucleotide that is at least 95% identical to SEQ ID NO:1 or 3 and encodes a polypeptide of SEQ ID NO:2 or 4, respectively. In yet another embodiment of the foregoing embodiments, the vector comprises a fragment of SEQ ID NO:1 or 3. In yet a further embodiment of any of the foregoing, the vector is an expression vector.

The disclosure also provides a host cell engineered to express a recombinant vector of the disclosure. In one embodiment, the host cell is a non-pathogenic attenuated host cell. The disclosure also provide a recombinant polypeptide produced by the host cell of the disclosure. In another embodiment, the recombinant polypeptide is purified from a host cell culture.

The disclosure also provides a composition comprising the host cell of disclosure.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1A: Culturable total Staphylococcus spp. were counted on a selective mannitol salt agar plate from 49 subjects with atopic dermatitis (AD) and 30 subjects without AD. FIG. 1B: CFU results for growth of S. aureus are shown from 30 non-atopic subjects and 49 atopic dermatitis patients. FIG. 1C: Total Staphylococcus spp. DNA abundance was determined by quantitative PCR (qPCR) on DNA from 14 non-atopic and 37 atopic subjects. Relative CFU (rCFU) was determined by comparison to a standard of known CFUs of S. epidermidis (ATCC12228). FIG. 1D: The ratio of live Staphylococcus spp. CFU to relative abundance of Staphylococcus determined by DNA was calculated at each corresponding skin site.

FIG. 2A-C. Atopic dermatitis skin is colonized by coagulase-negative Staphylococcus with a low frequency of antimicrobial activity. FIG. 2A: Coagulase-negative Staphylococcus (CoNS) with antimicrobial activity against S. aureus was determined by a high-throughput assay of individual culture isolates and the proportion (%) of total colonies that inhibited growth of S. aureus was determined. FIG. 2B: The proportion of CoNS with antimicrobial activity was determined from the same subjects at day-1, day-7 and day-14. FIG. 2C: The ratio of live Staphylococcus spp. to abundance of Staphylococcus DNA was determined from the same subjects as in FIG. 2B. *P<0.05, ****P<0.0001. 11 atopic and 11 non atopic subjects were randomly selected for analysis in Panels B and C.

FIG. 3A: The proportion of antimicrobial CoNS in each sample is plotted against the abundance of S. aureus cultured from each subject. Quadrants are divided based on frequency of antimicrobial CoNS (>50% or <50%) and detection of live S. aureus (<1 CFU/cm$^2$ or >1 CFU/cm$^2$). The proportion (%) of subjects in each quadrant to total subjects is shown. FIG. 3B: The frequency of antimicrobial CoNS in S. aureus-culture negative subjects (white) and S. aureus-culture positive subjects (solid) are shown. Data are mean±SE for 29 non-atopic subjects and 41 nonlesional or 40 lesional sites of atopic subjects.

FIG. 4A: Proportions of CoNS species identified with antimicrobial activity from 5 non-atopic subjects. FIG. 4B: Proportions of CoNS species identified from antimicrobial and non-antimicrobial colonies isolated from subjects with atopic dermatitis. Up to 48 CoNS isolates were sequenced from each individual. The relative proportion of colonies with antimicrobial (solid) and non-antimicrobial CoNS (white) from each AD subject is shown by pie chart.

FIG. 5A-B. Identification of antimicrobial peptides from a coagulase-negative Staphylococcus strain within the skin microbiome (SH-A9). FIG. 5A. Amino acid sequence and predicted mono and di-sulfide bonds from two antimicrobial peptides purified from S. hominis isolated from non-atopic skin. Peptides are named Hogocidin-α (SEQ ID NO:2 from aa 32-61) and Hogocidin-β (SEQ ID NO:4 aa 29-66) (SH-lantibiotic α and β). The calculated molecular weights of a hypothetical mature form of Hogocidin-α [3152.52 (M+H)] and Hogocidin-β [3548.04 (M+H)] are identical to the observed molecular masses [m/z 3152.22 and 3547.71 (M+H), respectively]. FIG. 5B shows dose response curves for the antimicrobial activity of Hogocidin-α and Hogocidin-β against *S. aureus*. Co-incubation with an antimicrobial peptide produced by human skin (LL-37) shows synergistic activity. Data represent mean±SE of triplicate assays. Arrow shows minimal inhibitory concentration (MIC) of each AMP, defined as 3-log reduction of viable bacteria in comparison to control. Dha, 2,3-didehydroalanine; Dhb, (Z)-2,3-didehydrobutyrine.

FIG. 9A shows the order of lantibiotic precursors (A1 and A2; SH-lantibiotic-α and β) and biosynthetic genes (C, T and M) on the *S. hominis* SH-A9 genome. FIG. 9B lists hypothetical gene, gene locus and putative function. This *S. hominis* strain contains multiple copies of the lantibiotic-related gene clusters.

FIG. 18A-B. Chromatograms showing results of FAME analysis of *S. hominis* strains C5 and C6, which do not produce hogocidin.

FIG. 20A-E. Transplantation of antimicrobial CoNS reduces survival of *S. aureus* on the skin. FIG. 20A: Effect of *S. hominis* on survival of *S. aureus* on pigskin. Live *S. hominis* A9 that produces hogocidin ($1\times10^5$ CFU/cm$^2$) was compared to controls including UV-killed and washed A9 strain, strains of live *S. hominis* that do not produce AMP activity (C4, C5 and C6) or vehicle cream alone with the pigskin assay. Data represent mean±s.e.m. of five independent assays. FIG. 20B: Effect of bacterial transplantation on survival of *S. aureus* on mouse skin. *S. aureus* was applied at $1\times10^5$ CFU/cm$^2$ on the shaved dorsal skin of mice. After two hours the control (vehicle alone), active *S. hominis* (A9), or inactive strains (C4, C5 and C6) were applied at equal concentrations ($1\times10^5$ CFU/cm$^2$). *S. aureus* recovery 20 hrs after application of CoNS or controls is shown. Data represent mean±s.e.m. of six mice. FIG. 20C: Work flow for autologous human microbiome transplant (AMT) on AD subjects colonized with *S. aureus*. FIG. 20D: Characterization of CoNS clones used for AMT. Antimicrobial class of each clone was identified by whole genome sequencing. FIG. 20E: Effect of transplantation of antimicrobial CoNS on the survival of *S. aureus* on the skin of subjects with AD. *S. aureus* survival was measured by colony counting of swabs taken before transplant (baseline) and 24 hrs after treatment. Difference in *S. aureus* between vehicle and AMT arms is shown as Δ % *S. aureus* CFU. Inactive strains have no effect.

FIG. 21A-C: Hypothetical antimicrobial genes identified in anti-*S. aureus* strains AMT1-A9 (FIG. 21A), AMT2-A12 (FIG. 21B), and AMT3-A12 (FIG. 21C) used for autologous microbiome transplant. Whole genome sequence of active CoNS clones were obtained by miSeq and analyzed on the RAST Server (rast.nmpdr.org) to identify antimicrobial class.

DETAILED DESCRIPTION

Figure 1A:
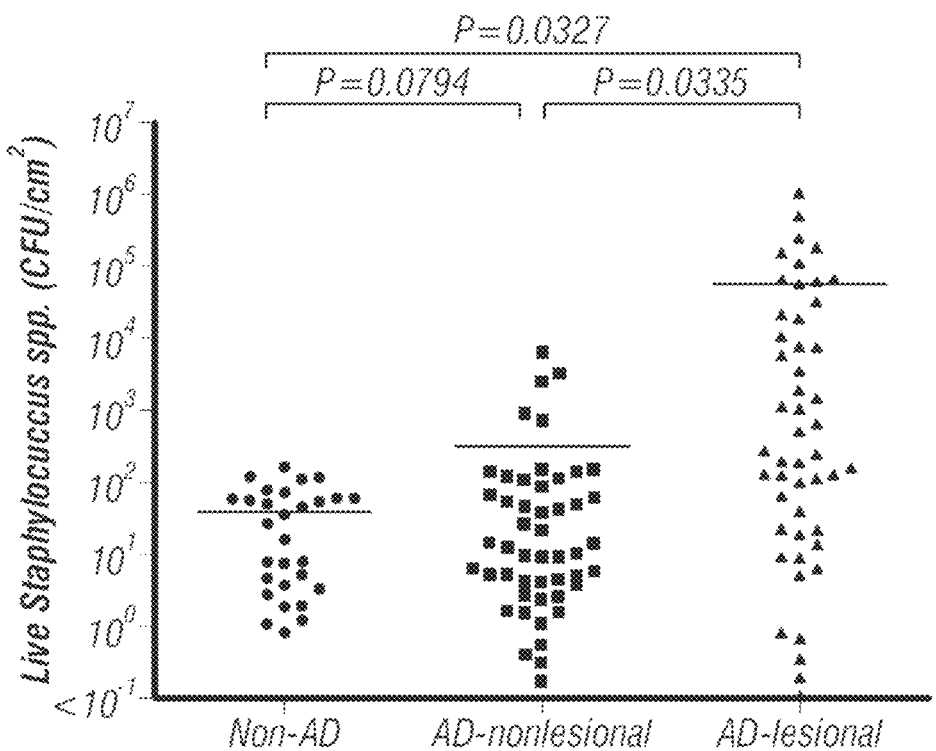
FIG. 1A-D. The ratio of culturable Staphylococcus compared to Staphylococcus DNA is higher in lesional skin of atopic dermatitis.

As used herein and in the appended claims, the singular forms "a," "and," and "the" include plural referents unless the context clearly dictates otherwise. Thus, for example, reference to "a probe" includes a plurality of such cells and reference to "the cell" includes reference to one or more cells and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. With respect to any term that is presented in one or more publications that is similar to, or identical with, a term that has been expressly defined in this disclosure, the definition of the term as expressly provided in this disclosure will control in all respects.

Atopic dermatitis is a common, chronic skin disorder characterized by dysfunction of the epidermal barrier and relapsing skin inflammation. The severity of this disease is associated with dysbiosis of the skin microbiome and the high susceptibility of these patients to colonization and infections by *Staphylococcus aureus*.

A unifying model for the etiology of atopic dermatitis has emerged with recognition that immunity is co-dependent upon functions provided by epithelia. For example, the production of antimicrobial peptides (AMPs) provides direct disinfectant activity against invading pathogens. In healthy skin, AMPs such as cathelicidins and β-defensins are increased after injury. However, the skin of patients with atopic dermatitis has a decreased capacity to produce certain AMPs and this is associated with an increased rate of infection by *S. aureus*, a pathogen that should be killed by these AMPs. *S. aureus* further exacerbates symptoms of atopic dermatitis and leads to immune dysfunction such as TH2 lymphocyte skewing, reduced AMPs, exacerbated allergic reactions and disruption of the skin barrier.

Prior studies of patients with atopic dermatitis have shown that the bacterial flora present on these patients is different than the bacteria found on the skin of non-atopic subjects. The microbiome of patients with atopic dermatitis is less diverse and typically has a higher abundance of Staphylococcal species. Without intending to be bound by any particular theory, it has been hypothesized that dysbiosis of the skin microbiome could contribute to the pathophysiology of this disease. Specifically, the diverse community of microorganisms that normally comprise the microbiome have been suggested to contribute to cutaneous homeostasis. For example, in mice, *Staphylococcus epidermidis* can control inflammation after injury, influence T-cell development and induce expression of AMPs. Furthermore, the microbiome may produce its own AMPs that could synergize with AMPs produced by host cells. Therefore, in addition to the deleterious effects of colonization by *S. aureus*, dysbiosis of the microbiome in atopic dermatitis could contribute to disease by loss of their beneficial functions.

Existing antibiotic therapies non-specifically kill bacteria, which impacts the homeostasis of the resident microflora. Imbalanced microflora contribute to the pathogenesis of skin inflammatory diseases, such as atopic dermatitis, rosacea and acne vulgaris etc. This disclosure provides compositions and formulations for disinfecting surfaces or treating infections but does not pose the safety risks of non-specific antibiotics. Further the disclosure provides for probiotic approaches wherein subjects may be provided with live *S. hominis* or *S. epidermidis* strains which may produce the necessary antimicrobial compounds in situ while simultaneously restoring the characteristics of a healthy cutaneous flora.

*Staphylococcus hominis* (*S. hominis*) is a major constituent of the microflora of healthy human skin. Recent studies indicate that *S. epidermidis* protect human skin by preventing pathogenic infections by producing phenol-soluble modulins (PSMs) and small molecule antibiotic, named "Firmocidin", which function as additional antimicrobial compounds on normal human skin (see, e.g., U.S. Pat. Publ. No. 2013/0331384A1, the disclosure of which is incorporated herein by reference). In addition, lipoteichoic acid produced by *S. epidermidis* benefits human skin by suppressing skin inflammation during wound repair. The present disclosure provides the use of live *S. epidermidis* and/or *S. hominis* cells or cultures to restore or enhance the normal cutaneous flora to support wound healing and prevent infection and restore skin barrier function.

A limitation of DNA sequencing is that it is unable to distinguish between viable and dead organisms, in the methods of the disclosure microbial abundance was directly evaluated in atopic and non-atopic subjects by both culture and DNA quantification techniques. Surprisingly, the relative capacity to culture live bacteria compared to measurements of DNA differed greatly between non-atopic and atopic dermatitis patients. Approximately 10 times more bacterial DNA relative to CFUs of cultured bacteria was detected in non-atopic skin compared to atopic lesional skin. These observations suggested a lower survival rate of bacteria on non-atopic skin than atopic lesional skin.

One explanation for the lower survival rate of bacteria on non-atopic skin is a more effective surface antimicrobial activity. AMPs such as LL-37 and hBDs-2 and -3 have lower levels of expression in inflamed skin of atopic patients than inflamed skin of normal subjects, but these AMP expressions are low in non-inflamed skin. Therefore, the increased capacity of the non-inflamed normal skin to kill bacteria is not likely due to the expression of these host AMPs. The high frequency of antimicrobial CoNS observed on non-atopic skin suggests that these resident bacteria are important to resist colonization by pathogens. Supporting this, S. aureus colonization was only detected in subjects with a low frequency of CoNS strains with antimicrobial activity. CoNS that could inhibit biofilm formation have also been observed in the nasal mucosa and inhibited nasal colonization by S. aureus. The observation of the lack of direct antimicrobial activity derived from the community of bacteria residing on the skin of patients with atopic dermatitis defines a previously unknown defect in the innate defense system of these individuals.

A high-throughput screen for antimicrobial activity on over 7500 individual isolates of coagulase-negative Staphylococcus (CoNS) cultured from the skin swabs of 30 healthy control subjects and 50 lesional and nonlesional sites of Atopic Dermatitis (AD) patients identified several CoNS isolates with antimicrobial activity. Healthy subjects had a high frequency of CoNS isolates with antimicrobial activity against Staphylococcus aureus (75.26±6.59%) whereas the bacteria isolated from AD nonlesional and lesional skin had significantly less activity [22.83±5.10%, 15.76±4.10%, respectively (p<0.0001)]. Notably, subjects with a low frequency of antimicrobial CoNS isolates were also colonized by SA. 16S rRNA sequencing revealed that antimicrobial activity was detected in diverse strains of CoNS, such as S. epidermidis, S. hominis, S. warneri, and S. capitis. Two prokaryotic AMPs with molecular weights of 3152.2 Da and 3550.7 Da were identified using HPLC, protein sequencing by MALDI-TOF-MS2 and genome sequencing. Additionally, as shown in Nakatsuji, T. et al. (2016), Nature Medicine Submitted Manuscript No. NMED-A78395A, submitted Mar. 29, 2016, which is incorporated herein by reference in its entirety, by applying functional CoNS isolates to ex vivo model systems, animal models, and through autologous transplants in human subjects, it was shown that the application of CoNS strains produce reductions in S. aureus levels in infected skin. For example, application of this antimicrobial CoNS isolate to mouse skin colonized by SA was effective in reducing SA survival by >90% above that seen when AD CoNS strains were applied. These findings suggest that the microbiome is the first line of defense against SA and that dysbiosis in AD has a major functional association to SA colonization.

Several CoNS species were identified that produced antimicrobial activity against S. aureus. Some laboratory strains of S. epidermidis and S. warneri were previously described to produce lantibiotics that could inhibit growth of other bacteria, but these were not detected in the subject population. Furthermore, several of the CoNS species isolated based on their antimicrobial activity were not previously suspected to have antimicrobial function. To better understand these, two previously unknown lantibiotics were identified that had potent activity against S. aureus and were highly synergistic with the host AMPs LL-37. The gene encoding these lantibiotics was prevalent in non-atopic individuals. This discovery illustrates the potential in further analysis of the host-defense function of the healthy human skin microbiome and may provide a genetic approach to predicting the activity of the microbiome. Metagenomic sequencing and correlation with functional screening of the microbiome could be of great benefit in the treatment of patients with atopic dermatitis and other skin diseases.

The disclosure provides evidence that the community of bacteria residing on normal human skin provides an important shield against S. aureus. Again, without intending to be bound by any particular theory, dysfunction in this microbiome-mediated antimicrobial defense system may enable colonization of the skin by S. aureus in atopic dermatitis and further exacerbation of the disease. This observation suggests that strategies of bacteriotherapy of the skin may be useful as a method to suppress S. aureus without use of pharmaceutically derived antibiotics. Given the complex nature of this disease, the ideal therapeutic approach to atopic dermatitis should include targeting both repair of the intrinsic epidermal barrier and optimizing the immune defense functions provided by the microbiome.

The disclosure also describes novel antimicrobial peptides (AMPs) from culture supernatant of a clinical isolate of S. hominis. These AMPs are referred to herein as Hogocidin-α and Hogocidin-β. Hogocidins exert antimicrobial and bactericidal activity against Staphylococcus aureus (S. aureus), but do not inhibit the growth of commensal bacteria on the skin such as S. epidermidis. Therefore, the disclosure represents provides antibiotics with potent but selective activity against pathogens, and high safety profile as they are found normally in the human skin microbiome, as well as probiotic approaches to treating these conditions.

The term "antimicrobial" as used herein means that the peptide destroys, or inhibits or prevents the growth or proliferation of, a microbe (e.g., a bacterium, fungus, and/or virus). Likewise, the term "antiviral" as used herein means that a peptide destroys, or inhibits or prevents the growth or proliferation of a virus or a virus-infected cell. The term "anti-tumor" as used herein means that a peptide prevents, inhibits the growth of, or destroys, a tumor cell(s). Similarly, the term "antifungal" means that a peptide prevents, destroys, or inhibits the growth of a fungus.

As used herein, "probiotic" refers to the process of providing live or attenuated microbial cultures, or lysates, lyophiles or extracts of such cultures, in order to supplement or replace elements of a healthy cutaneous or mucosal flora. An attenuated vector for delivery to the skin can be include a virus or bacteria that has been genetically modified to (a) make the vector non-pathogenic, (b) have reduced pathogenicity, (c) be replication defective, or (d) to be non-antigenic. Other attenuation are known in the art. The attenuation is typically performed by knocking out a gene or disrupting a gene coding sequence or expression control element such that the attention of (a)-(c) or (d) is accomplished. Such techniques are known in the art and numerous such attenuated bacterial and viral vectors are known.

The "hogocidins" are composed of two distinct domains: an N-terminal "prosequence" domain and the C-terminal domain of the mature hogocidin. The mature hogocidin-α comprises a sequence of SEQ ID NO:2 from about amino acid 32 to about amino acid 61 (e.g., beginning at about amino acid 30, 31, 32 or 33 of SEQ ID NO:2 and extending to about amino acid 59, 60 or 61 of SEQ ID NO:2). It will be readily apparent to one of skill in the art that the pre-pro form of hogocidin-α is about 61 amino acids in length and is post-translationally process to provide the mature form. Based upon the expression system and organism, the mature form may be processed slightly differently depending upon the proteases present. Moreover, it will also be readily apparent that the pre-pro form of hogocidin-α can be used in the methods, compositions and kits of the disclosure, wherein prior to or after administration the pre-pro form can be processed in vitro or in vivo.

Similarly, the mature form of hogocidin-β comprises a sequence of SEQ ID NO:4 from about amino acid 29 to about amino acid 66 (e.g., beginning at about amino acid 27, 28, 29 or 30 of SEQ ID NO:4 and extending to about amino acid 64, 65, or 66 of SEQ ID NO:4). It will be readily apparent to one of skill in the art that the pre-pro form of hogocidin-β is about 66 amino acids in length and is post-translationally process to provide the mature form. Based upon the expression system and organism, the mature form may be processed slightly differently depending upon the proteases present. Moreover, it will also be readily apparent that the pre-pro form of hogocidin-β can be used in the methods, compositions and kits of the disclosure, wherein prior to or after administration the pre-pro form can be processed in vitro or in vivo.

The polypeptide comprising SEQ ID NO:2 is typically cleaved following amino acid number 31 of SEQ ID NO:2, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 31 of SEQ ID NO:2.

The polypeptide comprising SEQ ID NO:4 is typically cleaved following amino acid number 28 of SEQ ID NO:4, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 31 of SEQ ID NO:4.

Although the genetic code is well understood by one of skill in the art and it is routine in generating polynucleotides encoding a desired polypeptides sequence; the disclosure also provides polynucleotides encoding the polypeptides of the disclosure. For example, the disclosure provides SEQ ID NO:1 and 3, which encode the polypeptides of SEQ ID NO:2 and 4.

As used herein, the term "hogocidin peptide" refers to the mature form of hogocidins comprising a chain of amino acids that is about 30 to about 50 amino acids in length and comprises a sequence as set forth in SEQ ID NO:2 or 4 or post-translationally modified versions thereof:

SEQ ID NO: 56
KCSWWNASCHLGNNGKICTVSHECAAGCNL
SEQ ID NO: 57
ATPTITTSSATCGGIIVAASAAQCPT-LACSSRCGKRKK.

In one embodiment, the method provides hogocidin derivatives comprising (a) peptides that are at least 90% identical to a hogocidin peptide of SEQ ID NO:2 or 4 and having antimicrobial activity; (b) mature forms of (a) that have been post-translationally processed; (c) fragments of hogocidin peptides that are about 15-40 amino acids in length and have antimicrobial activity; (d) fusion proteins comprising (a)-(c) above and having antimicrobial activity; (e) peptides comprising any of (a), (b), (c) or (d) wherein one or more amino acids comprise a D-amino acid and the peptide has antimicrobial activity; and (f) retroinverso peptides of any of the foregoing and having antimicrobial peptides. In some further embodiments, the method provides hogocidin derivatives comprising lanthionine or methyllanthionine residues, or hogocidin derivatives modified such that they contain lanthionine or methyllanthionine residues.

It is not necessary that the analog, derivative, variation, or variant have activity identical to the activity of the hogocidin peptide from which the analog, derivative, conservative variation, or variant is derived so long as it has some antimicrobial activity. In another embodiment, the disclosure provides a hogocidin polypeptide comprising at least one conservative amino acid difference compared to polypeptide of SEQ ID NO:2 or 4.

The disclosure also provides a polypeptide comprising a sequence of SEQ ID NO:55 at the N-terminal end and wherein the polypeptide has antimicrobial activity and observed molecular weight was 3484.90 (m/z). In a further embodiment, the polypeptide is produced by S. epidermidis A11.

The disclosure also provides compositions comprising a pharmaceutically acceptable excipient and comprising a substantially pure hogocidin peptide or derivative. The disclosure also provides compositions comprising a probiotic formulation which includes one or more hogocidin- or firmocidin-producing bacterial strains.

The term "purified" as used herein refers to a peptide that is substantially free of other proteins, lipids, and polynucleotides (e.g., cellular components with which an in vivo produced peptide would naturally be associated). Typically, the peptide is at least 70%, 80%, or most commonly 90% pure by weight. As described more fully below, the composition can further comprise a cathelicidin peptide or derivative thereof.

A "variant" is an antimicrobial peptide (e.g., a hogocidin peptide of the disclosure) that is an altered form of a referenced antimicrobial peptide. For example, the term "variant" includes an antimicrobial peptide produced by the method disclosed herein in which at least one amino acid (e.g., from about 1 to 10 amino acids) of a reference peptide is substituted with another amino acid. The term "reference" peptide means any of the antimicrobial peptides of the disclosure (e.g., a polypeptide consisting of SEQ ID NO:2 and 4 or a mature form thereof), from which a variant, derivative, analog, or conservative variation is derived. Included within the term "derivative" is a hybrid peptide that includes at least a portion of each of two antimicrobial hogocidin peptides. Derivatives can be produced by adding one or a few (e.g., 1 to 5) amino acids to an antimicrobial peptide without completely inhibiting the antimicrobial activity of the peptide. In addition, C-terminal derivatives, e.g., C-terminal methyl esters, can be produced and are encompassed by the disclosure.

The disclosure also includes peptides that are conservative variations of those peptides as exemplified herein. The term "conservative variation" as used herein denotes a polypeptide in which at least one amino acid is replaced by another, biologically, chemically, or structurally similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. Structurally conservative variations include the substitution of alanine for serine (and vice versa), isoleucine for threonine (and vice versa), arginine for lysine (and vice versa), and the replacement of any of tyrosine, phenylalanine, tryptophan, and histidine for any other member of that group. The term "conservative variation" also encompasses a peptide having a substituted amino acid in place of an unsubstituted parent amino acid; typically, antibodies raised to the substituted polypeptide also specifically bind the unsubstituted polypeptide.

As used herein, a "SH-lantibiotic" refers to a compound comprising a post-translationally modified peptide produced by *S. hominis* which optionally contains one or more lanthionine or methyllanthionine moieties, and shows antimicrobial activity against one or more non-*S. hominis* species.

As used herein, a "SH-antimicrobial" refers to a compound comprising a non-lantibiotic compound produced or secreted by *S. hominis*, which may optionally comprise a non-lantibiotic peptide, and which shows antimicrobial activity against one or more non-*S. hominis* species.

As used herein, a "SE-lantibiotic" refers to a compound comprising a post-translationally modified peptide produced by *S. epidermidis* which optionally contains one or more lanthionine or methyllanthionine moieties, and shows antimicrobial activity against one or more non-*S. epidermidis* species. In one embodiment, the peptide comprises a sequence of SEQ ID NO:55.

As used herein, a "SE-antimicrobial" refers to a compound comprising a non-lantibiotic compound produced or secreted by *S. epidermidis*, which may optionally comprise a non-lantibiotic peptide, and which shows antimicrobial activity against one or more non-*S. epidermidis* species.

Hogocidin peptide variants of the disclosure can be identified by screening a large collection, or library, of random peptides or peptides of interest using, for example, one of a number of animal models such as CRAMP knockout mice that display increased susceptibility to skin infections. Hogocidin peptide variants can be, for example, a population of peptides related in amino acid sequence to SEQ ID NO:2 and 4 by having various substitutions based upon such sequences.

Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid, which encodes it. Methods for the production of phage display libraries, including vectors and methods of diversifying the population of peptides, which are expressed, are known in the art (see, for example, Smith and Scott, Methods Enzymol. 217:228 257 (1993); Scott and Smith, Science 249:386 390 (1990); and Huse, WO 91/07141 and WO 91/07149). These or other known methods can be used to produce a phage display library, from which the displayed peptides can be cleaved and assayed for antibacterial activity. If desired, a population of peptides can be assayed for activity, and an active population can be subdivided and the assay repeated in order to isolate an active peptide from the population. Other methods for producing peptides useful in the disclosure include, for example, rational design and mutagenesis based on the amino acid sequences of a hogocidin peptide as set forth in SEQ ID NO:2 or 4, for example.

A hogocidin peptide variant can be a peptide mimetic, which is a non-amino acid chemical structure that mimics the structure of, for example, a hogocidin peptide of SEQ ID NO:2 or 4 (or a mature form thereof) yet retains antimicrobial/antibacterial activity. Such a mimetic generally is characterized as exhibiting similar physical characteristics such as size, charge or hydrophobicity in the same spatial arrangement found in the hogocidin peptide counterpart. A specific example of a peptide mimetic is a compound in which the amide bond between one or more of the amino acids is replaced, for example, by a carbon-carbon bond or other bond well known in the art (see, for example, Sawyer, Peptide Based Drug Design, ACS, Washington (1995)).

The amino acids of a hogocidin peptide, variant or peptidomimetic of the disclosure are selected from the twenty naturally occurring amino acids, including, unless stated otherwise, L-amino acids and D-amino acids. The use of D-amino acids are particularly useful for increasing the life of a protein or peptide. Polypeptides incorporating D-amino acids are resistant to proteolytic digestion. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment of a hogocidin peptide, variant and the like such that it retains its antimicrobial/antibacterial activity. Other examples of amino acids and amino acids analogs are listed in Gross and Meienhofer, The Peptides: Analysis, Synthesis, Biology, Academic Press, Inc., New York (1983). An amino acid also can be an amino acid mimetic, which is a structure that exhibits substantially the same spatial arrangement of functional groups as an amino acid but does not necessarily have both the "-amino" and "-carboxyl" groups characteristic of an amino acid.

Polypeptides and peptides of the disclosure can be synthesized by commonly used methods such as those that include t-BOC or FMOC protection of alpha-amino groups. Both methods involve stepwise synthesis in which a single amino acid is added at each step starting from the C terminus of the polypeptide or peptide (See, Coligan, et al., Current Protocols in Immunology, Wiley Interscience, 1991, Unit 9). Polypeptide and peptides of the disclosure can also be synthesized by the well-known solid phase peptide synthesis methods such as those described by Merrifield, J. Am. Chem. Soc., 85:2149, 1962) and Stewart and Young, Solid Phase Peptides Synthesis, Freeman, San Francisco, 1969, pp. 27 62). If desired, the peptides can be quantitated by the solid phase Edman degradation.

Using a synthesizer a hogocidin peptide (i.e., the mature form of SEQ ID NO:2 or 4 can be generated specifically without the need for post-translational processing.

The disclosure also includes isolated polynucleotides (e.g., DNA, cDNA, or RNA) encoding the polypeptide and peptides of the disclosure. Included are polynucleotides that encode analogs, mutants, conservative variations, and variants of the polypeptides and peptides described herein. The term "isolated" as used herein refers to a polynucleotide that is substantially free of proteins, lipids, and other polynucleotides with which an in vivo-produced polynucleotides naturally associated. Typically, the polynucleotide is at least 70%, 80%, or 90% isolated from other matter, and conventional methods for synthesizing polynucleotides in vitro can be used in lieu of in vivo methods.

As used herein, "polynucleotide" refers to a polymer of deoxyribonucleotides or ribonucleotides, in the form of a separate fragment or as a component of a larger genetic construct (e.g., by operably linking a promoter to a polynucleotide encoding a peptide of the disclosure). Numerous genetic constructs (e.g., plasmids and other expression vectors) are known in the art and can be used to produce the peptides of the disclosure in cell-free systems or prokaryotic or eukaryotic (e.g., yeast, insect, or mammalian) cells. By taking into account the degeneracy of the genetic code, one of ordinary skill in the art can readily synthesize polynucleotides encoding the peptides of the disclosure. The polynucleotides of the disclosure can readily be used in conventional molecular biology methods to produce the peptides of the disclosure.

DNA encoding the hogocidin peptides, derivatives of variants thereof of the disclosure can be inserted into an "expression vector." The term "expression vector" refers to a genetic construct such as a plasmid, virus or other vehicle known in the art that can be engineered to contain a polynucleotide encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide of the disclosure can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used to express the hogocidin peptides, derivatives or variants of the disclosure. The term also includes any progeny of a host cell. Host cells, which are useful, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein. In one embodiment, a host cell can comprise a bacterial cell present in a normal bacterial flora of the skin that has been engineered to express or over express a hogocidin peptide or other antimicrobial peptide of the disclosure. These engineered bacterial cells can then be used as a probiotic such that they are applied to skin.

Host cells can be eukaryotic host cells (e.g., mammalian cells). In one embodiment, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g. cytokines, clotting factors, and antibodies (Brasel et al., Blood 88:2004 2012 (1996); Kaufman et al., J. Biol Chem 263: 6352 6362 (1988); McKinnon et al., J Mol Endocrinol 6:231 239 (1991); Wood et al., J. Immunol 145:3011 3016 (1990)). The dihydrofolate reductase (DHFR)-deficient mutant cell lines (Urlaub et al., Proc Natl Acad Sci USA 77:4216 4220 (1980)) are the CHO host cell lines commonly used because the efficient DHFR selectable and amplifiable gene expression system allows high level recombinant protein expression in these cells (Kaufman, Meth Enzymol 185:527 566 (1990)). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Polynucleotides encoding the polypeptide and peptides of the disclosure can be isolated from a cell (e.g., a cultured cell), or they can be produced in vitro. A DNA sequence encoding a hogocidin peptide of interest can be obtained by: 1) isolation of a double-stranded DNA sequence from genomic DNA; 2) chemical manufacture of a polynucleotide such that it encodes the hogocidin peptide of interest; or 3) in vitro synthesis of a double-stranded DNA sequence by reverse transcription of mRNA isolated from a donor cell (i.e., to produce cDNA). Among the standard procedures for isolating cDNA sequences of interest is the formation of plasmid or phage containing cDNA libraries that are derived from reverse transcription of mRNA in donor cells that have a high level of genetic expression. When used in combination with polymerase chain reaction technology, even rare gene products can be cloned.

Any of various art-known methods for protein purification can be used to isolate the peptides of the disclosure. For example, preparative chromatographic separations and immunological separations (such as those employing monoclonal or polyclonal antibodies) can be used. Carrier peptides can facilitate isolation of fusion proteins that include the peptides of the disclosure. Purification tags can be operably linked to a hogocidin peptide of the disclosure. For example, glutathione-S-transferase (GST) allows purification with a glutathione agarose affinity column. When either Protein A or the ZZ domain from *Staphylococcus aureus* is used as the tag, purification can be accomplished in a single step using an IgG-sepharose affinity column. The pOprF-peptide, which is the N-terminal half of the *P. aeruginosa* outer membrane protein F, can readily be purified because it is the prominent protein species in outer membrane preparations. If desired, the fusion peptides can be purified using reagents that are specifically reactive with (e.g., specifically bind) the hogocidin peptide of the fusion peptide. For example, monoclonal or polyclonal antibodies that specifically bind the hogocidin peptide can be used in conventional purification methods. Techniques for producing such antibodies are well known in the art.

A fusion construct comprising a polypeptide linked to a hogocidin peptide of the disclosure can be linked at either the amino or carboxy terminus of the peptide. Typically, the polypeptide that is linked to the hogocidin peptide is sufficiently anionic such that the hogocidin peptide has a net charge that is neutral or negative. The anionic polypeptide can correspond in sequence to a naturally occurring protein or can be entirely artificial in design. Functionally, the polypeptide linked to a hogocidin peptide (the "carrier polypeptide") may help stabilize the hogocidin peptide and protect it from proteases, although the carrier polypeptide need not be shown to serve such a purpose. Similarly, the carrier polypeptide may facilitate transport of the fusion peptide. Examples of carrier polypeptides that can be utilized include anionic pre-pro peptides and anionic outer membrane peptides. Examples of carrier polypeptides include glutathione-S-transferase (GST), protein A of *Staphylococcus aureus*, two synthetic IgG-binding domains (ZZ) of protein A, outer membrane protein F of *Pseudomonas aeruginosa*, protein transduction domains and the like. The disclosure is not limited to the use of these polypeptides; others suitable carrier polypeptides are known to those skilled in the art. In another aspect, a linker moiety comprising a protease cleavage site may be operably linked to a hogocidin peptide or variant of the disclosure. For example, the linker may be operable between to domains of a fusion protein (e.g., a fusion protein comprising a hogocidin peptide and a carrier polypeptide). Because protease cleavage recognition sequences generally are only a few amino acids in length, the linker moiety can include the recognition sequence within flexible spacer amino acid sequences, such as GGGGS (SEQ ID NO: 6). For example, a linker moiety including a cleavage recognition sequence for Adenovirus endopeptidase could have the sequence GGGGGGSMFG-GAKKRSGGGGG (SEQ ID NO: 7). If desired, the spacer DNA sequence can encode a protein recognition site for cleavage of the carrier polypeptide from the hogocidin peptide. Examples of such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at methionine or related residues. In addition, the fused product can be cleaved by insertion of a codon for tryptophan (cleavable by o-iodosobenzoic acid) or glutamic acid (cleavable by *Staphylococcus* protease). Insertion of such spacer DNA sequences is not a requirement for the production of functional hogocidin peptides, such sequences can enhance the stability of the fusion peptide. The pre-pro defensin sequence is negatively charged, so accordingly, it is envisioned within the disclosure that other DNA sequences encoding negatively charged peptides also can be used as spacer DNA sequences to stabilize the fusion peptide.

The disclosure also provides a method for inhibiting the growth of a bacterium by contacting the bacterium with an inhibiting effective amount of a peptide of the disclosure. The term "contacting" refers to exposing the bacterium to the peptide so that the peptide can inhibit, kill, or lyse bacteria. The disclosure also provides a method for inhibiting skin disease or disorder and/or bacterial infection comprising placing on or within a subject a probiotic formulation comprising bacteria which secrete a peptide or antimicrobial molecule such that the growth of the pathogen or undesirable microbe is inhibited or prevented. Contacting of an organism with a hogocidin peptide of the disclosure can occur in vitro, for example, by adding the peptide to a bacterial culture to test for susceptibility of the bacteria to the peptide, or contacting a bacterially contaminated surface with the peptide. Alternatively, contacting can occur in vivo, for example by administering the peptide to a subject afflicted with a bacterial infection or susceptible to infection. Further, contacting can occur by exposing the bacterium to a probiotic formulation comprising bacterial strains that produce the hogocidin peptide, or other peptide or non-peptide inhibitors of bacterial growth. In vivo contacting includes both parenteral as well as topical. "Inhibiting" or "inhibiting effective amount" refers to the amount of peptide that is sufficient to cause, for example, a bacteriostatic or bactericidal effect. Bacteria that can be affected by the peptides of the disclosure include both gram-negative and gram-positive bacteria. For example, bacteria that can be affected include *Staphylococcus aureus*, *Streptococcus pyogenes* (group A), *Streptococcus* sp. (*viridans* group), *Streptococcus agalactiae* (group B), *S. bovis*, *Streptococcus* (anaerobic species), *Streptococcus pneumoniae*, and *Enterococcus* sp.; Gram-negative cocci such as, for example, *Neisseria gonorrhoeae*, *Neisseria meningitidis*, and *Branhamella catarrhalis*; Gram-positive bacilli such as *Bacillus anthracis*, *Bacillus subtilis*, *P. acne Corynebacterium diphtheriae* and *Corynebacterium* species which are diptheroids (aerobic and anerobic), *Listeria monocytogenes*, *Clostridium tetani*, *Clostridium difficile*, *Escherichia coli*, *Enterobacter species*, *Proteus mirablis* and other sp., *Pseudomonas aeruginosa*, *Klebsiella pneumoniae*, *Salmonella*, *Shigella*, *Serratia* sp., and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections. Fungal organisms may also be affected by the hogocidin peptides of the disclosure and include dermatophytes (e.g., *Microsporum canis* and other *Microsporum* sp.; and *Trichophyton* sp. such as *T. rubrum*, and *T. mentagrophytes*), yeasts (e.g., *Candida albicans*, *C. Tropicalis*, or other *Candida* species), *Saccharomyces cerevisiae*, *Torulopsis glabrata*, *Epidermophyton floccosum*, *Malassezia furfur* (*Pityropsporon orbiculare*, or *P. ovale*), *Cryptococcus neoformans*, *Aspergillus fumigatus*, *Aspergillus nidulans*, and other *Aspergillus* sp., *Zygomycetes* (e.g., *Rhizopus*, *Mucor*), *Paracoccidioides brasiliensis*, *Blastomyces dermatitides*, *Histoplasma capsulatum*, *Coccidioides immitis*, and *Sporothrix schenckii*. The method for inhibiting the growth of bacteria can also include contacting the bacterium with the peptide in combination with one or more antibiotics.

A peptide(s) of the disclosure can be administered to any host, including a human or non-human animal, in an amount effective to inhibit growth of a bacterium, virus, or fungus. Thus, the peptides are useful as antimicrobial agents, antiviral agents, and/or antifungal agents. The bacterial strains that produce the peptides are useful as probiotic agents.

Any of a variety of art-known methods can be used to administer the peptide to a subject. For example, the peptide of the disclosure can be administered parenterally by injection or by gradual infusion over time. The peptide can be administered intravenously, intraperitoneally, intramuscularly, subcutaneously, intracavity, topically or transdermally. In another embodiment, a hogocidin peptide of the disclosure may be formulated for topical administration (e.g., as a lotion, cream, spray, gel, oil suspension, or ointment). Examples of formulations in the market place include topical lotions, creams, soaps, wipes, powders, devices like gauze pads to cover wounds, and the like. It may be formulated into liposomes to reduce toxicity or increase bioavailability or stability. Other methods for delivery of the peptide include oral methods that entail encapsulation of the peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a peptide of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, chelating agents, inert gases and the like also can be included.

The disclosure provides a method for inhibiting a topical bacterial or fungal-associated disorder by contacting or administering a therapeutically effective amount of a peptide or skin-probiotic of the disclosure to a subject who has, or is at risk of having, such a disorder. The term "inhibiting" means preventing or ameliorating a sign or symptoms of a disorder (e.g., a rash, sore, and the like). Examples of disease signs that can be ameliorated include an increase in a subject's blood level of TNF, fever, hypotension, neutropenia, leukopenia, thrombocytopenia, disseminated intravascular coagulation, adult respiratory distress syndrome, shock, and organ failure. Examples of subjects who can be treated in the disclosure include human or animal subjects at risk for, or those suffering from, a toxemia, such as endotoxemia resulting from a gram-negative bacterial infection, venom poisoning, or hepatic failure. Other examples include subjects having a dermatitis as well as those having skin infections such as mastitis and especially bovine mastits, or injuries subject to infection with gram-positive or gram-negative bacteria or a fungus. Examples of candidate patients include those suffering from infection by *E. coli, Hemophilus influenza* B, *Neisseria meningitides*, staphylococci, or pneumococci. Other patients include those suffering from gunshot wounds, renal or hepatic failure, trauma, burns, immunocompromising infections (e.g., HIV/SIV/FIV infections), hematopoietic neoplasias, multiple myeloma, Castleman's disease or cardiac myxoma. Those skilled in the art of medicine can readily employ conventional criteria to identify appropriate subjects for treatment in accordance with the disclosure.

The term "therapeutically effective amount" as used herein for treatment of a subject afflicted with a disease or disorder means an amount of hogocidin peptide sufficient to ameliorate a sign or symptom of the disease or disorder. For example, a therapeutically effective amount can be measured as the amount sufficient to decrease a subject's symptoms of dermatitis or rash by measuring the frequency of severity of skin sores. Typically, the subject is treated with an amount of hogocidin peptide sufficient to reduce a symptom of a disease or disorder by at least 50%, 90% or 100%. Generally, the optimal dosage of the peptide will depend upon the disorder and factors such as the weight of the patient, the type of bacterial or fungal infection, the weight, sex, and degree of symptoms. Nonetheless, suitable dosages can readily be determined by one skilled in the art. Typically, a suitable dosage is 0.5 to 40 mg peptide/kg body weight, e.g., 1 to 8 mg peptide/kg body weight.

If desired, a suitable therapy regime can combine administration of a peptide(s) or probiotic composition of the disclosure with one or more additional therapeutic agents (e.g., an inhibitor of TNF, an antibiotic, and the like). The peptide(s), other therapeutic agents, and/or antibiotic(s) can be administered, simultaneously, but may also be administered sequentially. Suitable antibiotics include aminoglycosides (e.g., gentamicin), beta-lactams (e.g., penicillins and cephalosporins), quinolones (e.g., ciprofloxacin), and novobiocin. Generally, the antibiotic is administered in a bactericidal amount. However, the peptide provides for a method of increasing antibiotic activity. Typically, the hogocidin peptide and antibiotic are administered within 48 hours of each other (e.g., 2 to 8 hours, or may be administered simultaneously). A "bactericidal amount" is an amount sufficient to achieve a bacteria-killing blood concentration in the subject receiving the treatment. In accordance with its conventional definition, an "antibiotic," as used herein, is a chemical substance that, in dilute solutions, inhibits the growth of, or kills microorganisms. Also encompassed by this term are synthetic antibiotics (e.g., analogs) known in the art.

The peptides of the disclosure can be used, for example, as preservatives or sterilants of materials susceptible to microbial or viral contamination. For example, the peptides can be used as preservatives in processed foods (e.g., to inhibit organisms such as *Salmonella, Yersinia, Listeria* and *Shigella*). If desired, the peptides can be used in combination with antibacterial food additives, such as lysozymes. The peptides and/or probiotics of the disclosure also can be used as a topical agent, for example, to inhibit *Pseudomonas* or *Streptococcus* or kill odor-producing microbes (e.g., Micrococci). The optimal amount of a hogocidin peptide of the disclosure for any given application can be readily determined by one of skill in the art.

The hogocidins and/or probiotics of the disclosure are also useful in promoting wound repair and tissue regeneration. Matrix metalloproteinases (MMPS) are inflammatory enzymes that degrade proteins in various tissues. Recent scientific research has shown elevated levels of proteases (e.g., MMPs) in chronic wound exudate, the fluid that bathes the wound bed. These excess proteases cause degradation of important extracellular matrix proteins and inactivation of vital growth factors that are essential in the wound healing process. This may contribute to a sub-optimal healing environment resulting in delayed wound healing.

Compositions provided herein can be used concurrently with other antibacterial agents including sulfa drugs such as sulfamethizole, sulfisoxazole, sulfamonomethoxine, sulfamethizole, salazosulfapyridine, silver sulfadiazine and the like; quinoline antibacterial agents such as nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like; antiphthisics such as isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like; antiacidfast bacterium drugs such as diaphenylsulfone, rifampicin and the like; antiviral drugs such as idoxuridine, acyclovir, vidarabine, ganciclovir and the like; anti-HIV agents such as zidovudine, didanosine, zalcitabine, indinavir sulfate ethanolate, ritonavir and the like; antispirocheteles; antibiotics such as tetracycline hydrochloride, ampicillin, piperacillin, gentamicin, dibekacin, kanendomycin, lividomycin, tobramycin, amikacin, fradiomycin, sisomycin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group and the like.

In humans, there are several classes of known antimicrobial peptides (AMPS) including α-defensins, β-defensins, and cathelicidins. Cathelicidins are found in several mammalian species. Production of cathelicidins is induced in response to epithelial wounding or infectious challenge, or suppressed by the virulence mechanisms of certain bacterial pathogens, e.g., Shigella dysenteriae. Cathelicidin expression is also differentially effected in certain chronic inflammatory disorders. In psoriasis, cathelicidin levels are elevated and secondary infection is rare, whereas in atopic dermatitis cathelicidin expression is deficient and bacterial or viral superinfection is common. Therapeutic benefits of cathelicidin have been demonstrated experimentally, including decreased bacterial colonization of skin wounds following topical administration and improved pulmonary bacterial clearance with cathelicidin overexpression through viral gene transfer. The hogocidin peptides of the disclosure show a synergistic effect with cathelicidins. Thus, in some embodiments a formulation, composition and method comprise both a hogocidin and cathelicidin. In some embodiments, a topical formulation (e.g., a lotion, ointment or aerosol spray) can comprise both a cathelicidin and hogocidin peptide (or derivatives thereof).

Cathelicidin proteins are composed of two distinct domains: an N-terminal "cathelin-like" or "prosequence" domain and the C-terminal domain of the mature AMP. The C-terminal domains of cathelicidins were among the earliest mammalian AMPs to show potent, rapid, and broad-spectrum killing activity. The term "cathelin-like" derives from the similarity of the N-terminal sequence with that of cathelin, a 12 kDa protein isolated from porcine neutrophils that shares similarity with the cystatin superfamily of cysteine protease inhibitors.

Cathelicidins are expressed in neutrophils and myeloid bone marrow cells and most epithelial sources, and were the first AMPs discovered in mammalian skin due to their presence in wound fluid. In the neutrophil, cathelicidins are synthesized as full length precursor and targeted to the secondary granules where they are stored. Upon stimulation, the full-length cathelicidin protein is proteolytically processed to unleash the microbiocidal activity of the C-terminal peptide from the cathelin-like domain.

The C-terminal 37 amino acids of human cathelicidin (LL-37) has been characterized. LL-37 was originally referred to as FALL39, named for the first 4 N-terminal amino acids of this domain and the total number of residues (i.e., 39). LL-37 is a peptide predicted to contain an amphipathic alpha helix and lacks cysteine, making it different from all other previously isolated human peptide antibiotics of the defensin family, each of which contain 3 disulfide bridges. Full length human cathelicidin (sometimes referred to as full length LL-37) comprises the cathelin-like precursor protein and the C-terminal LL-37 peptide, thus comprising 170 amino acids (SEQ ID NO:5).

The polypeptide comprising SEQ ID NO:5 has a number of distinct domains. For example, a signal domain comprising a sequence as set forth from about 1 to about 29-31 of SEQ ID NO:5 is present. The signal domain is typically cleaved following amino acid number 30 of SEQ ID NO:5, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 30 of SEQ ID NO:5. Another domain comprises the N-terminal domain, referred to as the cathelin-like domain. The cathelin-like domain comprises from about amino acid 29 (e.g., 29-31) to about amino acid 128 (e.g., 128-131) of SEQ ID NO:5. Yet another domain of SEQ ID NO:5 comprises the C-terminal domain referred to as LL-37. The LL-37 domain comprises from about amino acid 128 (e.g., 128-134) to amino acid 170 of SEQ ID NO:5. LL-37 comprises the amino acid sequence set forth in SEQ ID NO:5.

```
                                            (SEQ ID NO: 5)
MKTQRNGHSLGRWSLVLLLLGLVMPLAIIAQVLSYKEAVLRAIDGINQRS

SDANLYRLLDLDPRPTMDGDPDTPKPVSFTVKETVCPRTTQQSPEDCDFK

KDGLVKRCMGTVTLNQARGSFDISCDKDNKRFALLGDFFRKSKEKIGKEF

KRIVQRIDDFLRNLVPRTES
```

The mechanisms by which cationic human antimicrobial peptides kill bacteria and fungi are generally through binding of the peptide to the microbial cell membrane, after which the membrane's proton gradient and integrity are lost.

Vitamin D3 (or its analogs) with hogocidin (and in some embodiments in combination with a cathelicidin) can be administered systemically to treat systemic infections, in particular pneumonia, sepsis and TB. It may also be applied topically to treat infectious skin disorders. It may be used in combination therapy with antibiotics or to treat immunocompromised patients such as HIV positive individuals. In combination with immune stimulating approaches, it may therapeutically address cancer.

The compositions and methods of the disclosure may also comprise treating disorders of skin dysbiosis by administration of an antimicrobial compound or an organism secreting an antimicrobial compound, or administration of a probiotic composition comprising organisms that support skin health. In some embodiments, the composition includes a second active agent (e.g., an antibiotic, vitamin D3, cathelicidin etc.).

In some embodiments, the compositions described herein comprise a probiotic organism. In further embodiments, the probiotic organism is a bacterium. In further embodiments, the bacterium comprises a component of the normal skin flora. In further embodiments, the bacterium comprises a strain of Staphylococcus hominis. In other embodiments, the bacterium comprises a strain of Staphylococcus epidermidis. In other embodiments, the probiotic organism comprises a mixture of strains. In some embodiments, the mixture of strains comprises multiple strains of S. hominis. In other embodiments, the mixture of strains comprises multiple strains of S. epidermidis. In other embodiments, the mixture of strains comprises one or more strains of S. hominis and one or more strains of S. epidermidis. In some embodiments, the composition comprises one or more strains in addition to S. hominis and/or S. epidermidis. In some further embodiments, the additional strain or strains comprise one or more strains from the genus Staphylococcus, Lactobacillus or Lactococcus. For example, specific formulations may comprise Staphylococcus hominis or Staphylococcus epidermidis, in particular, Staphylococcus hominis strain A9, Staphylococcus hominis strain C2, Staphylococcus hominis strain AMT2, Staphylococcus hominis strain AMT3, Staphylococcus hominis strain AMT4-C2, *Staphylococcus hominis* strain AMT4-G1, *Staphylococcus hominis* strain AMT4-D12, *Staphylococcus epidermidis* strain AMT1, *Staphylococcus epidermidis* strain SE-A11, *Staphylococcus epidermidis* strain AMT5-C5, and/or *Staphylococcus epidermidis* strain AMT5-G6. Such formulations typically comprise sufficient quantities of bacterial cells as to provide a final density of $10^3$-$10^6$ CFU/cm$^2$ when applied to the skin of a subject. Such formulations may comprise concentrations of from about $10^4$ to about $10^7$ CFU/g, or alternatively, from 10 to about $10^5$ CFU/g, or alternatively, from about $10^5$ to about $10^9$ CFU/g. Such formulations may comprise multiple strains of *S. hominis* and/or *S. epidermidis*, and may further comprise *Lactococcus lactis, Lactobacillus plantarum, Lactobacillus rhamnosus, Lactobacillus acidophilus*, and/or other such species or strains as are known in the art to form a part of the normal healthy cutaneous or mucosal flora. In some embodiments, *S. hominis* strains as described above comprise 100% of the bacterial cells in a formulation. In some further embodiments, *S. hominis* comprises 90-100%, 85-95%, 70-80%, 75-85%, 60-70%, 65-75%, 50-60%, 55-65%, 40-50%, 45-55%, 30-40%, 35-45%, 20-30%, 25-35%, 10-20%, 15-20%, 1-10%, 5-15%, or less than 1% of the bacterial cells in a given formulation, wherein the remainder of the colony forming units are provided by *S. epidermidis, Lactococcus lactis, Lactobacillus plantarum, Lactobacillus rhamnosus, Lactobacillus acidophilus*, and/or other such strains as are known in the art to form a part of the normal healthy cutaneous or mucosal flora. In some embodiments, *S. epidermidis* strains as described above comprise 100% of the bacterial cells in a formulation. In some further embodiments, *S. epidermidis* comprises 90-100%, 85-95%, 70-80%, 75-85%, 60-70%, 65-75%, 50-60%, 55-65%, 40-50%, 45-55%, 30-40%, 35-45%, 20-30%, 25-35%, 10-20%, 15-20%, 1-10%, 5-15%, or less than 1% of the bacterial cells in a given formulation, wherein the remainder of the colony forming units are provided by *S. hominis, Lactococcus lactis, Lactobacillus plantarum, Lactobacillus rhamnosus, Lactobacillus acidophilus*, and/or other such strains as are known in the art to form a part of the normal healthy cutaneous or mucosal flora. In some embodiments, bacteria other than *S. hominis* or *S. epidermidis* comprise about 50% or less of the bacterial cells in the formulation. In some embodiments said bacteria comprise less than 50%, less than 40%, less than 30%, less than 20%, less than 10%, less than 5%, or less than 1% of the bacterial cells within a given formulation. In some embodiments, bacteria other than *S. hominis* or *S. epidermidis* may comprise *Lactococcus lactis, Lactobacillus plantarum, Lactobacillus rhamnosus, Lactobacillus acidophilus*, and/or other such species or strains as are known in the art to form a part of the normal healthy cutaneous or mucosal flora. In some embodiments, the formulations comprise about 60% *S. hominis* of the strains listed above and about 40% *S. epidermidis* of the strains listed above. In some embodiments, the formulations comprise about 50% *S. hominis* of the strains listed above and about 50% *S. epidermidis* of the strains listed above. In some embodiments, the formulations comprise about 40% *S. hominis* of the strains listed above and about 60% *S. epidermidis* of the strains listed above. In some embodiments, the formulations comprise about 70% *S. hominis* of the strains listed above and about 30% *S. epidermidis*. In some embodiments, the formulations comprise about 30% *S. hominis* of the strains listed above and about 70% *S. epidermidis* of the strains listed above. In some embodiments, the formulations comprise about 80% *S. hominis* of the strains listed above and about 20% *S. epidermidis* of the strains listed above. In some embodiments, the formulations comprise about 20% *S. hominis* of the strains listed above and about 80% *S. epidermidis* of the strains listed above. In some embodiments, the formulations comprise about 90% *S. hominis* of the strains listed above and about 10% *S. epidermidis* of the strains listed above. In some embodiments, the formulations comprise greater than about 90% *S. hominis* of the strains listed above and less than about 10% *S. epidermidis* of the strains listed above. In some embodiments, the formulations comprise less than about 10% *S. hominis* of the strains listed above and greater than about 90% *S. epidermidis* of the strains listed above.

As used herein, an autologous transplant refers to the transplantation of bacterial strains from one site to another on the same subject or to the same site, regardless of whether the strains are cultured prior to administration or not. In some embodiments, the bacterial strains obtained from the subject are expanded in culture and then transplanted back to the subject.

As used herein, an allogeneic transplant refers to the transplantation of bacterial strains from one subject to another subject, or to the administration to a subject of a composition comprising bacterial strains that were not collected from upon or within their own body.

Such collection can be carried out by swabbing, scraping, wiping, or cutting and removing tissue on which resides one of the bacterial strains as described herein; optionally growing and isolating single colonies from agar plates or otherwise using methods known in the art; optionally growing expanded cultures of the isolated bacteria or crude swabs, wipes, scrapes, tissue, or other isolate in liquid or solid culture according to methods known in the art; optionally harvesting bacteria from said expanded culture by centrifugation, filtration, gravity settling, scraping, or by other means known in the art; formulating the bacteria or the crude isolate with a thickener, carrier, or excipient; and contacting the subject in an area determined to be in need of the transplant, with said formulation.

As used herein, a prebiotic compound comprises a polysaccharide, hydrolysate, salt, herbal extract, or any other compound sufficient to foster the growth of an associated probiotic strain when used in combination with that strain, such as yeast hydrolysate in concentrations of less than about 40% (w/w), microcrystalline cellulose in concentrations of less than about 10% (w/w), and/or sucrose in concentrations of less than about 10% (w/w). Other examples of prebiotics that may be adapted for use with cutaneous bacteria include inulin, glucooligosaccharides, isomaltooligosaccharides, lactosucrose, polydextrose, soybean oligosaccharides, and xylooligosaccharides, and those disclosed in Gibson, G. R. and Roberfroid, M, (Eds.) *Handbook of Prebiotics*, CRC press (2008); Roberfroid, M., J. Nutr. 137(3):830S-837 (2007) and Slavin, J. Nutrients 5(4): 1417-1435 (2013), each of which is incorporated herein by reference in its entirety.

In some embodiments the method comprises contacting a subject with a probiotic and/or prebiotic composition as described herein. In some embodiments, such contact comprises an autologous transplant. In some embodiments such contact comprises an allogeneic transplant, wherein elements of the cutaneous or mucosal flora are transplanted to a first subject in need thereof from a second subject (the donor). For example, in some embodiments, bacterial strains as disclosed above are identified and isolated from a second subject, amplified in an appropriate culture medium under such conditions as are known in the art to be conducive to bacterial growth, followed by harvest of the bacterial cells, mixing of the harvested cells at a predetermined concentration according to the disclosure with a predetermined formulation, and application of the mixture to the affected area of the first subject. In some embodiments such composition comprises a standardized formulation, such as a formulation in which the concentrations of ingredients are fixed and are not varied from subject to subject. In some embodiments, the formulation is developed individually for each subject, based on criteria including but not limited to: the composition of the subject's own cutaneous or mucosal flora; the subject's disease state and treatment history; the nature and severity of the subject's condition; the nature and severity of concurrent cutaneous or mucosal infections; the presence of other antimicrobial compounds including systemic antibiotics within the subject's body; and other criteria such as are known to or would readily be apparent to those of skill in the art.

In some embodiments, the composition comprises a cream, ointment, oil suspension or unguent wherein the probiotic bacteria as described above are incorporated within a moisturizer or emulsion such as those described below and in Nakatsuji, T. et al. (2016), Nature Medicine Submitted Manuscript No. NMED-A78395A, submitted Mar. 29, 2016. In some embodiments, the composition comprises a patch or poultice wherein the bacteria are combined with a suitable excipient and are incorporated within a fabric, gel matrix, or polymer sheet. Suitable excipients and carriers for topical administration are known in the art and include thickeners, emulsifiers, fatty acids, polysaccharides, polyols, and polymers and copolymers, including, without limitation, alginate, microcrystalline cellulose, polylactic acid, polylactic-co-glycolic acid, petrolatum, and numerous others known in the art.

In some embodiments, the composition comprises a bacterial culture medium, a conditioned bacterial culture medium, and/or a bacterial culture. In some embodiments, the composition comprises a filtrate or supernatant of a bacterial culture medium. In some embodiments, the composition comprises a lyophilized culture medium. In some embodiments, the composition comprises a lyophilized conditioned culture medium produced from a filtrate or supernatant of a bacterial culture medium.

In some embodiments, the method as described herein comprises supporting the health of the skin of a subject. In further embodiments, the method comprises providing a treatment for skin dysbiosis and disorders derived therefrom. In some embodiments the method comprises providing a treatment for bacterial infection of the skin. In some embodiments, the treatment comprises the steps of: identifying a subject with skin dysbiosis, bacterial infection, mastitis, burn or other wound, atopic dermatitis, psoriasis, or other chronic skin condition; and administering to the site of the condition in need of treatment the probiotic compositions as disclosed herein. Determination of the appropriate mode of administration of a given formulation (ointment, gel, patch, etc.) can be done by one of ordinary skill in the art of treating skin infections. In some further embodiments, the probiotic compositions are re-applied at regularly timed intervals. In some embodiments, the probiotic compositions are reapplied every three days. In some embodiments, the probiotic compositions are reapplied every two days. In some embodiments, the probiotic compositions are reapplied every two days. In some embodiments, the probiotic compositions are reapplied daily. In some embodiments, the probiotic compositions are reapplied more than once per day. In some embodiments, the probiotic compositions are reapplied weekly. In some embodiments, the probiotic compositions are only applied a single time.

In some embodiments, the method comprises providing a treatment for *Staphylococcus aureus*, including methicillin or oxacillin resistant *S. aureus*, infections. In some further embodiments, the method comprises the steps of: diagnosing an *S. aureus* infection; and applying to the site of the infection the probiotic and/or prebiotic compositions as disclosed herein, wherein such compositions are capable of killing or inhibiting the growth of *S. aureus*, either by production of antimicrobial compounds, by competition for resources within the cutaneous or mucosal biota, or by other means. Determination of the appropriate mode of administration of a given formulation (ointment, gel, patch, etc.) can be done by one of ordinary skill in the art of treating skin infections. In some further embodiments, the probiotic compositions are re-applied at regularly timed intervals (e.g., daily, every two days, every three days, weekly, etc.). It will be apparent to one of ordinary skill in the art that in other embodiments, similar or identical steps can be applied to provide a treatment for *Pseudomonas aeruginosa* infections or infections derived from bacteria of the genus *Pseudomonas, Staphylococcus, Propionibacterium, Streptococcus,* or *Vibrio*, or uncharacterized pathogens. In some embodiments, the method comprises providing a treatment for infections with unknown or uncharacterized pathogens. In some embodiments, the method comprises providing a treatment for polymicrobial infections. In some embodiments, the method comprises administering such treatment to a burn or wound. In some embodiments, the method comprises providing a treatment for a chronic skin condition. In some embodiments, the condition is atopic dermatitis, psoriasis, or other chronic skin condition.

The following examples are intended to illustrate but not limit the disclosure. While they are typical of those that might be used, other procedures known to those skilled in the art may alternatively be used.

EXAMPLES

Example 1

Isolation of CoNS Strains and Antimicrobial Peptides. Adult patients with atopic dermatitis and age-matched non-atopic subjects were recruited. Demographic data are shown in Table 1. All experiments involving human subjects were carried out according to the IRB protocols approved by the facility.

TABLE 1

Clinical characteristics of atopic dermatitis and nonatopic subjects.

|  |  | Atopic subjects (N = 50)* | Non-atopic subjects (N = 30) |
|---|---|---|---|
| Facility (%) | 1 | 54.00 | 63.33 |
|  | 2 | 46.00 | 36.67 |
| Age | Mean ± SD | 33.80 ± 2.02 | 33.87 ± 1.49 |
| BMI | Mean ± SD | 25.10 ± 1.55 | 23.40 ± 1.15 |
|  | Not recorded (%) | 30.00 | 63.33 |
| Gender(%) | Male | 42.00 | 56.67 |
|  | Female | 58.00 | 43.33 |
| Race(%) | Caucasian | 50.00 | 60.00 |
|  | Asian | 32.00 | 33.33 |
|  | Hispanic | 6.00 | 6.67 |
|  | African-American | 8.00 | 0.00 |
|  | Other | 4.00 | 0.00 |

TABLE 1-continued

Clinical characteristics of atopic dermatitis and nonatopic subjects.

|  |  | Atopic subjects (N = 50)* | Non-atopic subjects (N = 30) |
|---|---|---|---|
| EASI Score(%) | <=6 | 26.00 | N/A |
|  | >6 | 48.00 | N/A |
|  | Not recorded | 26.00 | N/A |

*No live Staphylococcus and Staphylococcus DNA were detected in 1 subject with atopic dermatitis out of 50 patients recruited. Therefore the data are reported for 49 atopic subjects.
BMI, body mass index; EASI, eczema area and severity index; NJH, National Jewish Health; SD, standard deviation Measurements of bacterial abundance. Collection of live surface bacteria and bacterial DNA was done from a pre-measured area (~3×10 cm) of lesional skin on the antecubital fossa, and nonlesional skin of the upper arm at least 2 cm separated from the lesional site. Similar collections were obtained from non-atopic subjects at identical skin sites. Skin was rubbed with swabs pre-moistened with tryptic soy broth (TSB) for collecting live bacteria or with Tris-EDTA buffer for collecting bacterial DNA. Live bacteria samples were inoculated on a mannitol salt agar with egg yolk to distinguish coagulase negative staphylococcus (CoNS). Total genomic DNA was extracted with QIAamp DNA micro kit (Qiagen) and DNA abundance determined by quantitative real-time PCR (qPCR) with species- or genus-specific primers. No live Staphylococcus and Staphylococcus DNA were detected in 1 subject with atopic dermatitis out of 50 patients recruited. Therefore data are reported for 49 AD subjects.

Quantification of Bacterial DNA. To collect bacterial DNA, pre-measured areas similar to those used for bacterial culture were rubbed with a swab pre-moistened with Tris-EDTA buffer containing 0.1% TritonX-100 and 0.05% Tween-20 (w/v). Bacterial cells were lysed by proteinase K, followed by purified achromopeptidase (Wako Chemical) and Ready-Lyse® (epicenter Inc.). Total genomic DNA was purified with QIAamp DNA micro kit (Qiagen) and eluted with 50 µL of elution buffer. The abundance of bacterial DNA was determined by quantitative real-time PCR (qPCR) with species- or genus-specific primers (Table 2). To determine relative CFU (rCFU) of Staphylococcus spp. DNA, a standard curve was generated with genomic DNA extracted from standards derived from known CFU of S. epidermidis (ATCC12228). The specificity of all primer pairs was confirmed by melting curve analysis and comparison with standard curves.

TABLE 2

Sequences of PCR primers

| Primer name | Sequence (5' - 3') | Target gene | References or accession# |
|---|---|---|---|
| S. aureus-femA-2F | AACTGTTGGCCACTATGAGT (SEQ ID NO: 8) | S. aureus-specific sequence |  |
| S. aureus-femA-2R | CCAGCATTACCTGTAATCTCG (SEQ ID NO: 9) |  |  |
| S. epidermidis-sodA-F | TCAGCAGTTGAAGGACAGAT (SEQ ID NO: 10) | S. epidermidis-specific sequence |  |
| S. epidermidis-sodA-R | CCAGAACAATGAATGGTTAAGG (SEQ ID NO: 11) |  |  |
| g-Staph-F | TTTGGGCTACACACGTGCTACAATGGACAA (SEQ ID NO: 12) | Staphylococcus-genus specific 16S sequence |  |
| g-Staph-R | AACAACTTTATGGGATTTGCWTGA (SEQ ID NO: 13) |  |  |
| Univ16S-27-F | AGAGTTTGGATCMTGGCTCAG (SEQ ID NO: 14) | Universal sequence of bacterial 16S rRNA |  |
| Univ16S-1525-R | AAGGAGGTGWTCCARCC (SEQ ID NO: 15) |  |  |
| S. epidermidis-epiA-F | GATTCAGGAGCTGAACCAAGA (SEQ ID NO: 16) | S. epidermidis epidermin | X07840 |
| S. epidermidis-epiA-R | TTGAAGCCCTGCCAATCTAA (SEQ ID NO: 17) |  |  |
| S. epidermidis-pepA-F | CTGATGAACTTGAACCTCAAACTG (SEQ ID NO: 18) | S. epidermidis pep5 | L23967 |
| S. epidermidis-pepA-R | GACACTGTAAATAAACGCGTAGC (SEQ ID NO: 19) |  |  |
| S. epidermidis-eciA-F | GCAACTAGACAGGTATGTCCTAAA (SEQ ID NO: 20) | S. epidermidis epicidin280 | Y14023 |
| S. epidermidis-eciA-R | CATCTAAGATTAAATGAGGGTGGTT (SEQ ID NO: 21) |  |  |
| S. epidermidis-elkA-F | TAAGTCCGCAATCTGCTAGTG (SEQ ID NO: 22) | S. epidermidis epilancin K7 | U20348 |
| S. epidermidis-elkA-R | CAGTAATATTGCAACCGCATGT (SEQ ID NO: 23) |  |  |

TABLE 2-continued

Sequences of PCR primers

| Primer name | Sequence (5' - 3') | Target gene | References or accession# |
| --- | --- | --- | --- |
| Hogocidin-α-F | ATGAGTAAATTAGAACTACTTAATG (SEQ ID NO: 24) | S. hominis Hogocidin-α | This study |
| Hogocidin-α-R | TTATAAATTACATCCTGCTGCACAC (SEQ ID NO: 25) | | |

Screening for antimicrobial activity. Up to 84 individual colonies of CoNS isolates from each skin site were randomly picked and transferred to a 96-well cluster tube containing TSB. Each plate also received a non-antimicrobial strain of *S. epidermidis* (ATCC1457) as negative control, a known antimicrobial strain of *Staphylococcus hominis* (see below) as positive control, and blank wells without bacteria. CoNS were cultured at 37° C. overnight with shaking. Growth was evaluated by $OD_{600}$. Bacteria were removed by centrifugation followed by sterile filtration with a 0.22 μm membrane. The antimicrobial activity released from each colony was evaluated by mixing with $1 \times 10^4$ colony-forming units (CFU) of *S. aureus* (ATCC35556). Antimicrobial strains were defined as those that suppressed *S. aureus* growth after 22 hrs to less than 50% ($I_{50}$) of growth seen in negative controls. Insufficient CoNS colonies were grown from some of the subjects recruited. Therefore data are reported for 29 non-atopic subjects and 41 nonlesional and 40 lesional sites of atopic subjects. All CoNS isolates were stored frozen for species identification. Full-length 16S rRNA genes were amplified from 48 representative colonies with universal 16S primers, 27-F and 1525-R. Amplicons were sequenced from both ends by Sanger method.

Purification of AMPs produced by *S. hominis*. Sterile conditioned media from a representative antimicrobial *S. hominis* strain isolated from a healthy subject was used to further identify molecules with antimicrobial activity on normal skin that were in low abundance on atopics. Activity was precipitated by ammonium sulfate (70% saturation), dissolved in $H_2O$ and applied on a Sep-Pak cartridge (Waters Co). Active fractions were eluted with 30% acetonitrile in $H_2O$ and subjected to HiTrap® SP (GE Healthcare Life Sciences) separation and activity eluted at 125 mM NaCl. Third step HPLC purification was done with CapCel Pak C8 (5 μm, 300 Å, 4.6×250 mm) (Shiseido Co.) with a linier gradient of acetonitrile from 5% to 50% in 0.1% (v/v) TFA at 0.8 mL/min.

Identification of AMPs produced by *S. hominis*. Antimicrobial activity was purified from sterile conditioned media of a representative antimicrobial *S. hominis* strain isolated from a non-atopic subject. The secondary structure of the purified active molecules was determined by MALDI-TOF/TOF, Edman terminal sequencing, and genome sequencing.

Mass Spectrometry. Mass spectra of HPLC-purified AMPs from *S. hominis* were recorded using a MALDI-TOF/TOF Bruker Autoflex™ Speed instrument (Bruker Daltonics) controlled by the flexcontrol software (Bruker Daltonics). Mass spectrometric analyses were performed in positive ion reflectron mode using cyano-4-hydroxycinnamic acid as a matrix (CHCA) 10 mg/mL (Sigma-Aldrich) dissolved in 50% acetonitrile (ACN) and 0.1% trifluoroacetic acid (TFA). Full scan mass spectra were acquired in positive ion reflectron mode for mass range 1000-4000 m/z. Each mass spectrum is the result of 750 averaged laser shots with the laser intensity set around 65% of full laser intensity and a detector gain enhanced at 8×4 GS/s (as selected within the Bruker Flex Control software). MALDI-MS/MS spectra of manually selected ion m/z 3547, with a window range of 5 Da, were acquired using TOF/TOF collision-induced dissociation. Each MS/MS spectrum is the result of 1000 averaged laser shots with the laser intensity set around 60% selected within the software and a detector gain enhanced at 10×4 GS/s. Resulting mass spectra were analyzed using flex analysis software (Bruker Daltonics). Spectra were calibrated to PepMix internal standard solutions.

Figure 7A:
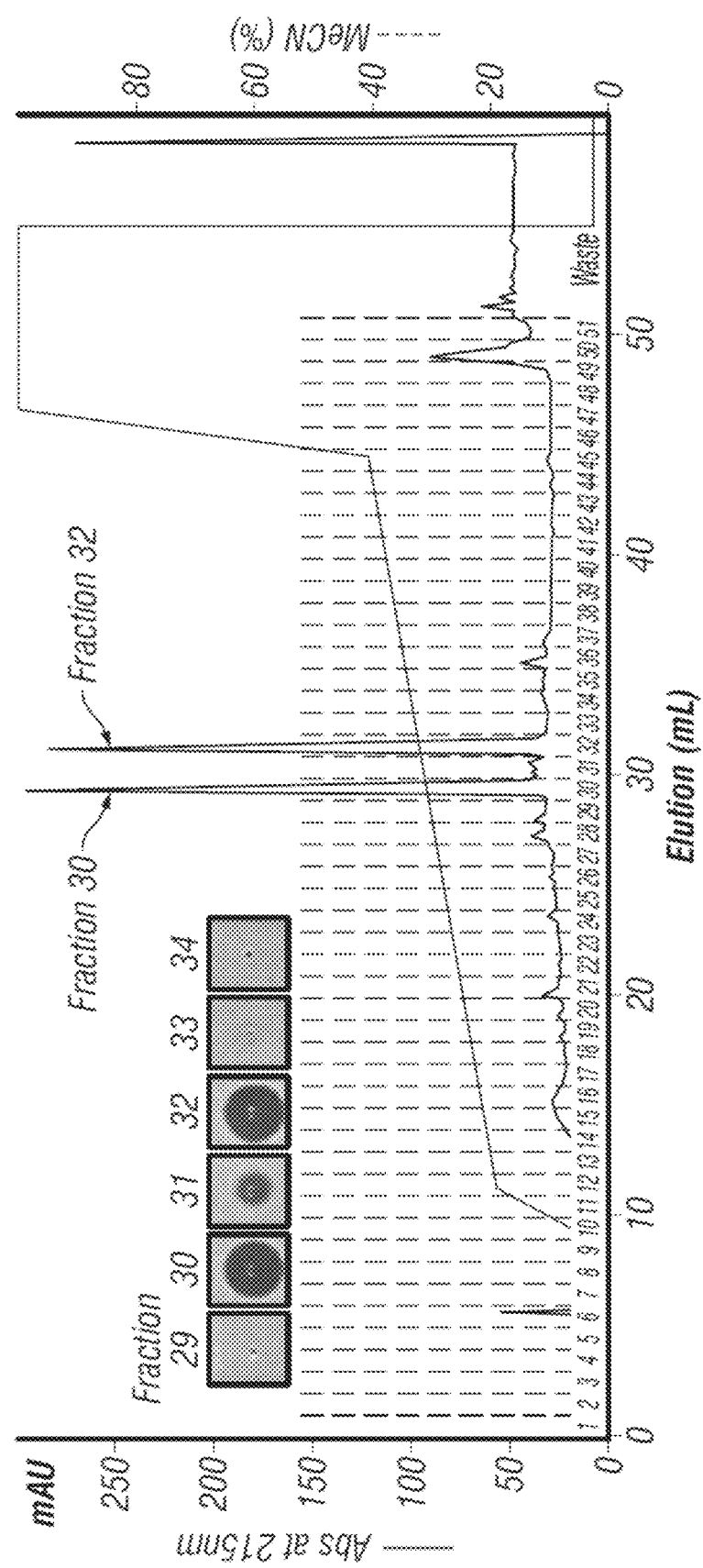
FIG. 7A-B. Purification and mass spectrometric analysis of AMPs produced by *S. hominis* isolated from non-atopic skin (SH-A9). AMPs were purified by HPLC using Capcel-Pac C8 column from culture supernatant of a representative antimicrobial isolate of *S. hominis* (FIG. 7A). The last step of 5 purification steps is shown. The insert panel represents antimicrobial activity of each fraction on radial diffusion assay against *S. aureus*. Fractions with antimicrobial activity were characterized by MALDI-TOF-MS (FIG. 7B).

N-terminal Protein Sequencing. The N-terminal amino acid sequence of purified Hogocidin-α (Fraction 30, FIG. 7A) was analyzed by 15 cycles of Edman degradation on Procise® 494HT Protein Sequence system (Applied Biosystems). A predicted mature form of Hogocidin-α is shown in FIG. 5A.

Figure 8:
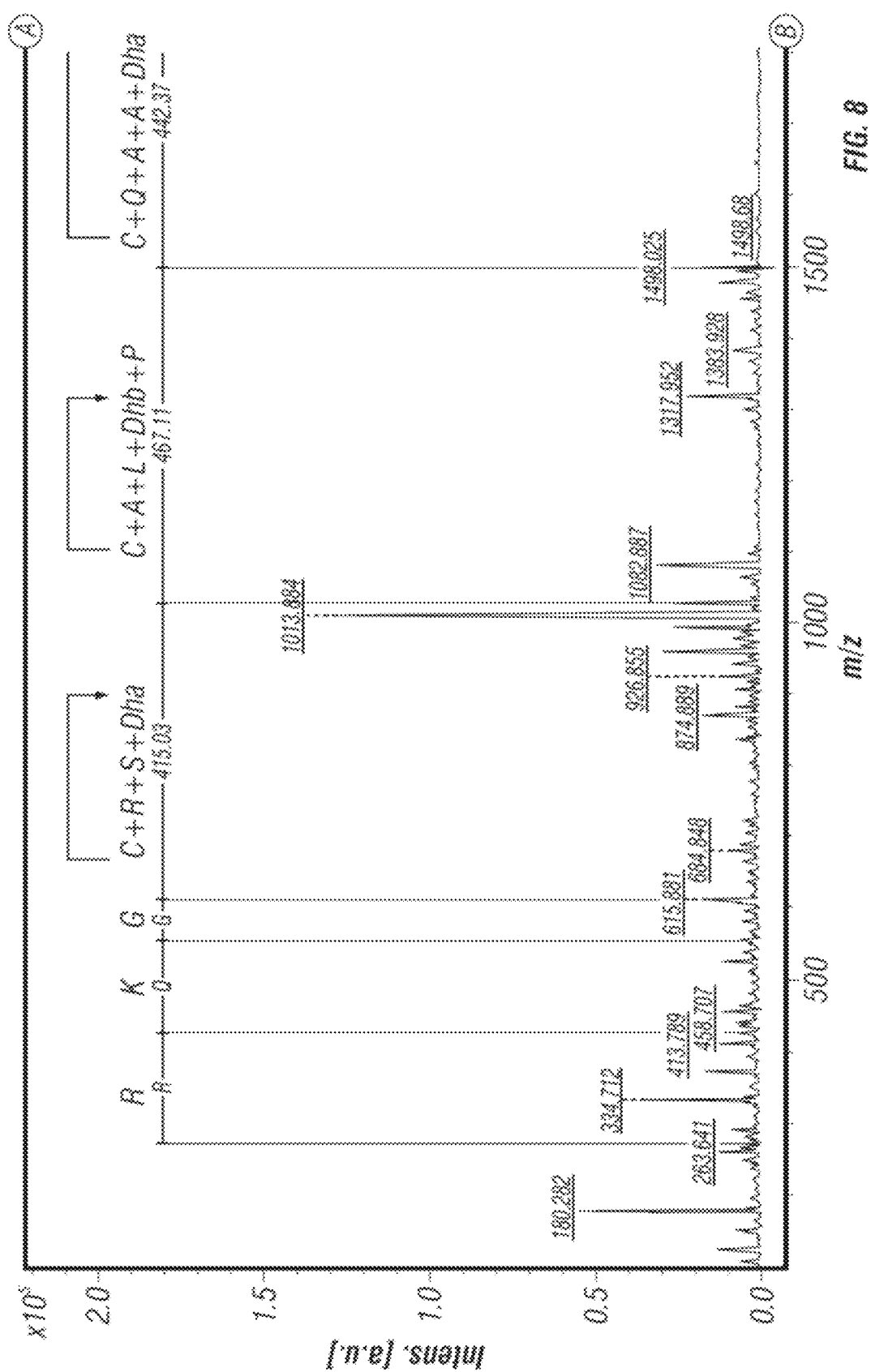
FIG. 8. Representation of amino acids losses in genome-guided MALDI-TOF/TOF analysis for Hogocidin-β (SH-lantibiotic-β). Amino acid sequence of purified Hogocidin-β was obtained from amino acids losses in MS/MS fragmentation spectrum of precursor mass 3547.7 m/z. Dha, 2,3-didehydroalanine; Dhb, (Z)-2,3-didehydrobutyrine.
Figure 8:
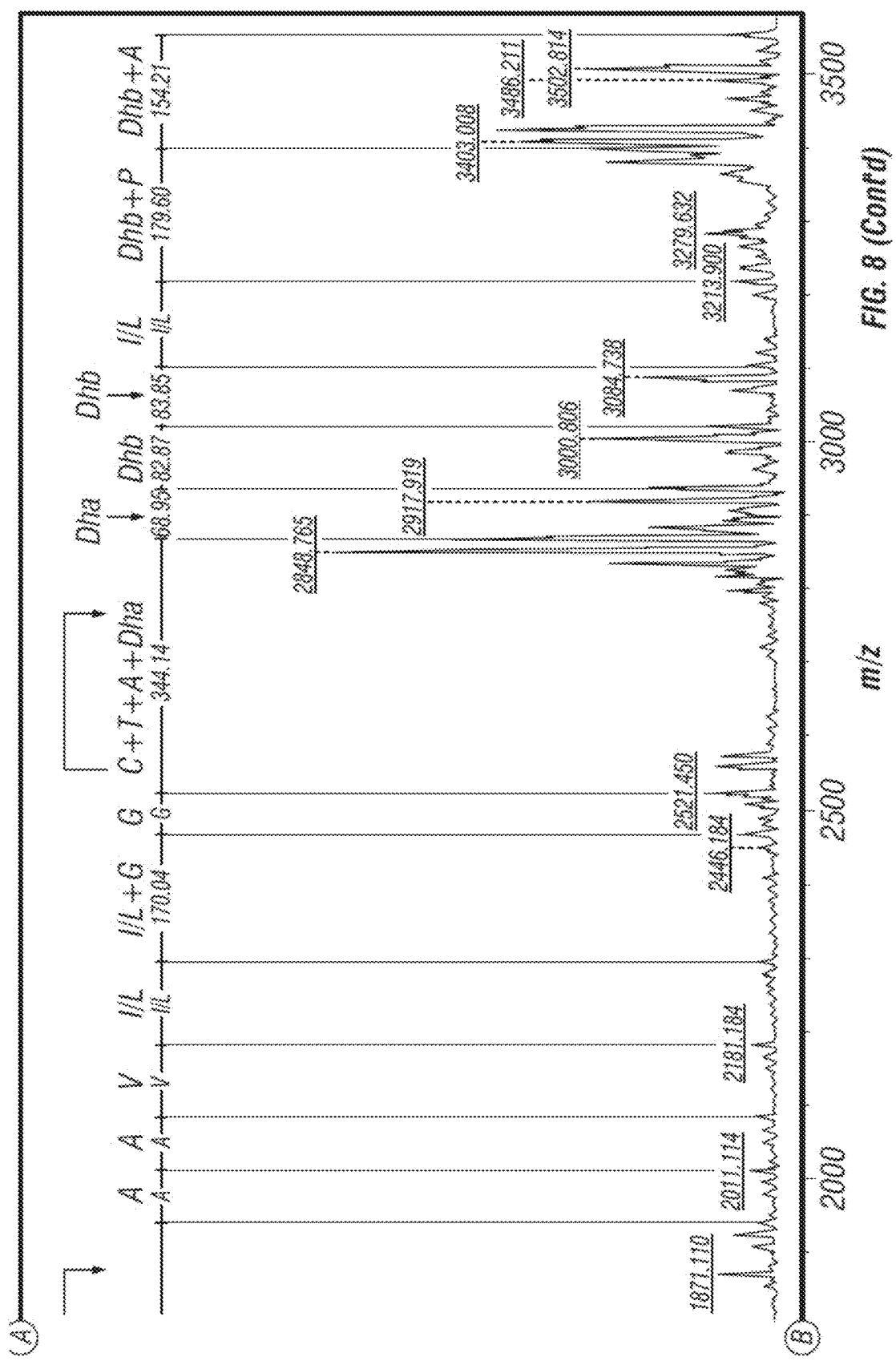
Figures 9A, 9B:
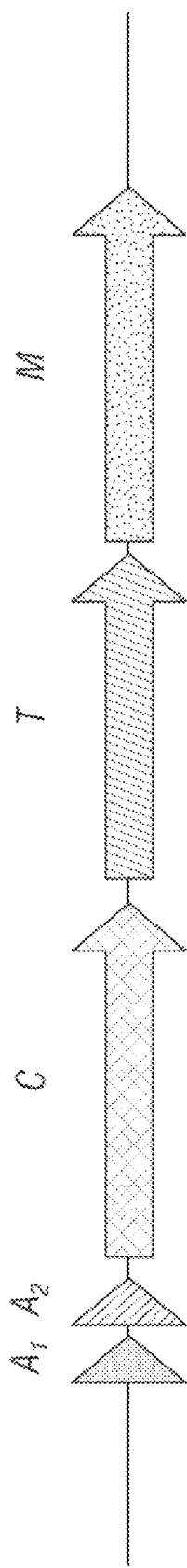
FIG. 9A-B. Organization of gene clusters encoding Hogocidin precursors and lantibiotic biosynthetic genes in a *S. hominis* strain isolated from non-atopic skin (SH-A9).
Figure 10:
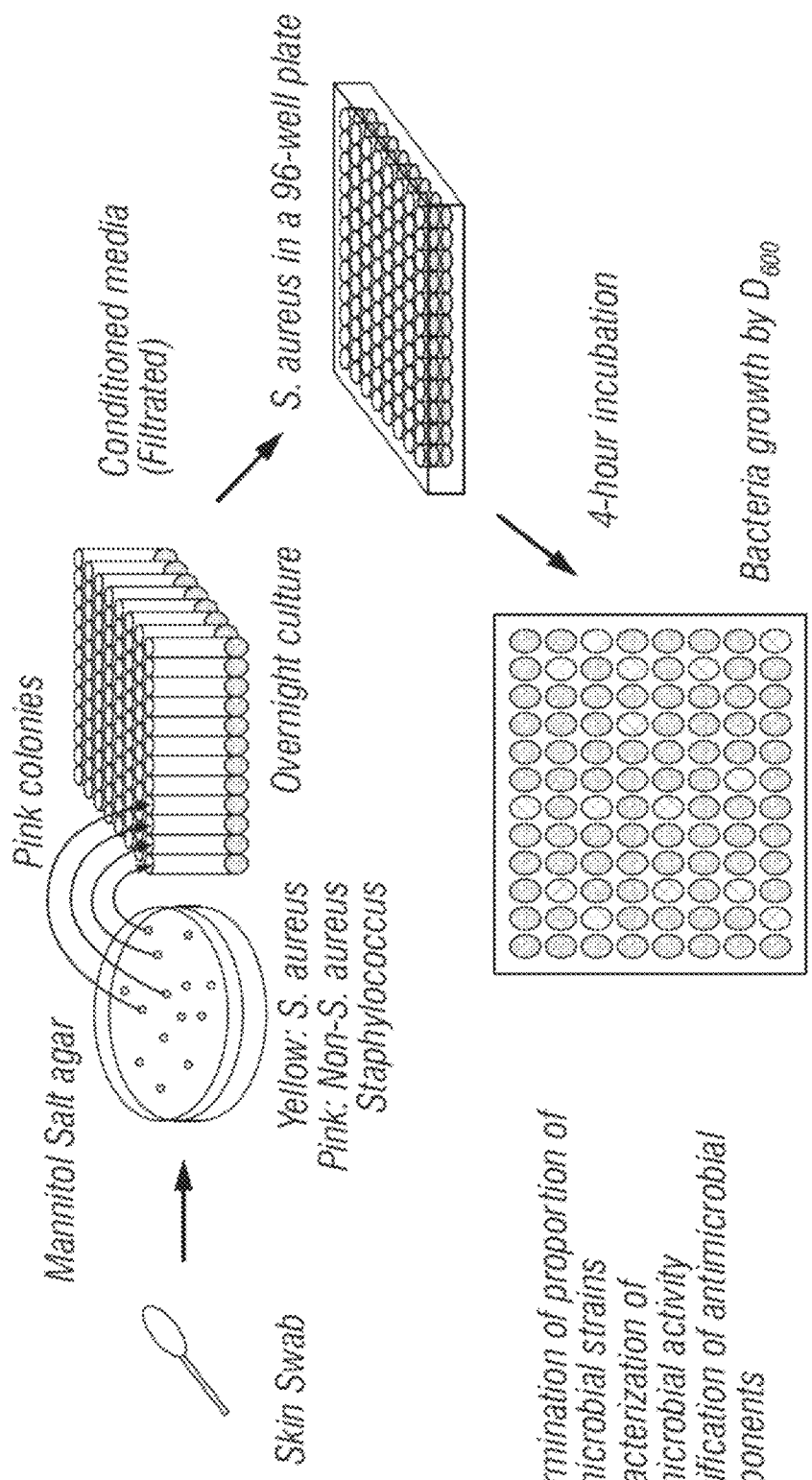
FIG. 10 shows the high-throughput methodology used in the disclosure.
Figure 11A:
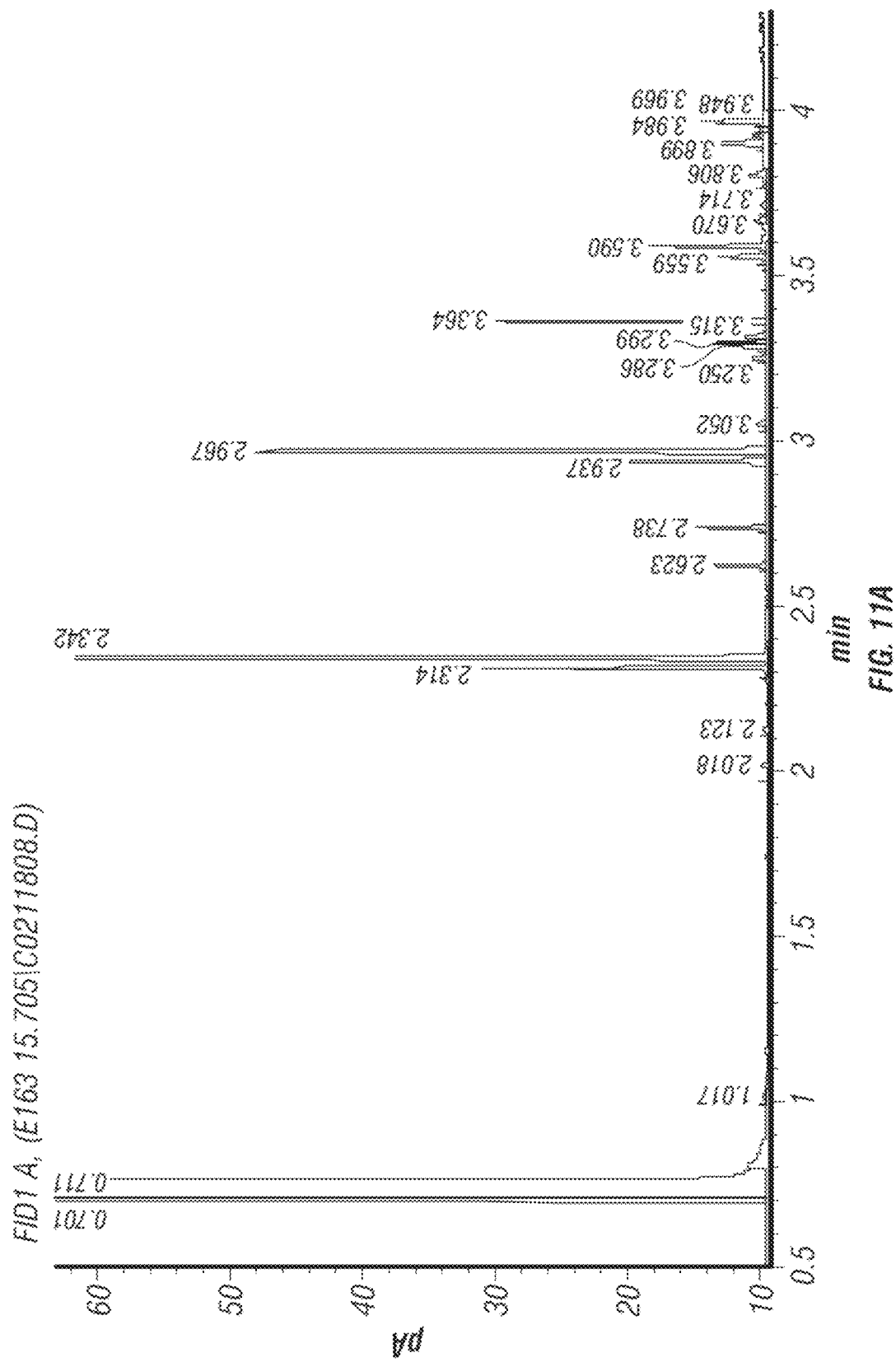
FIG. 11A-B. Chromatograms showing results of FAME analysis of *S. epidermidis* strains MO-34 and MO-38, which were identified by the methods given in the present disclosure.
Figure 11B:
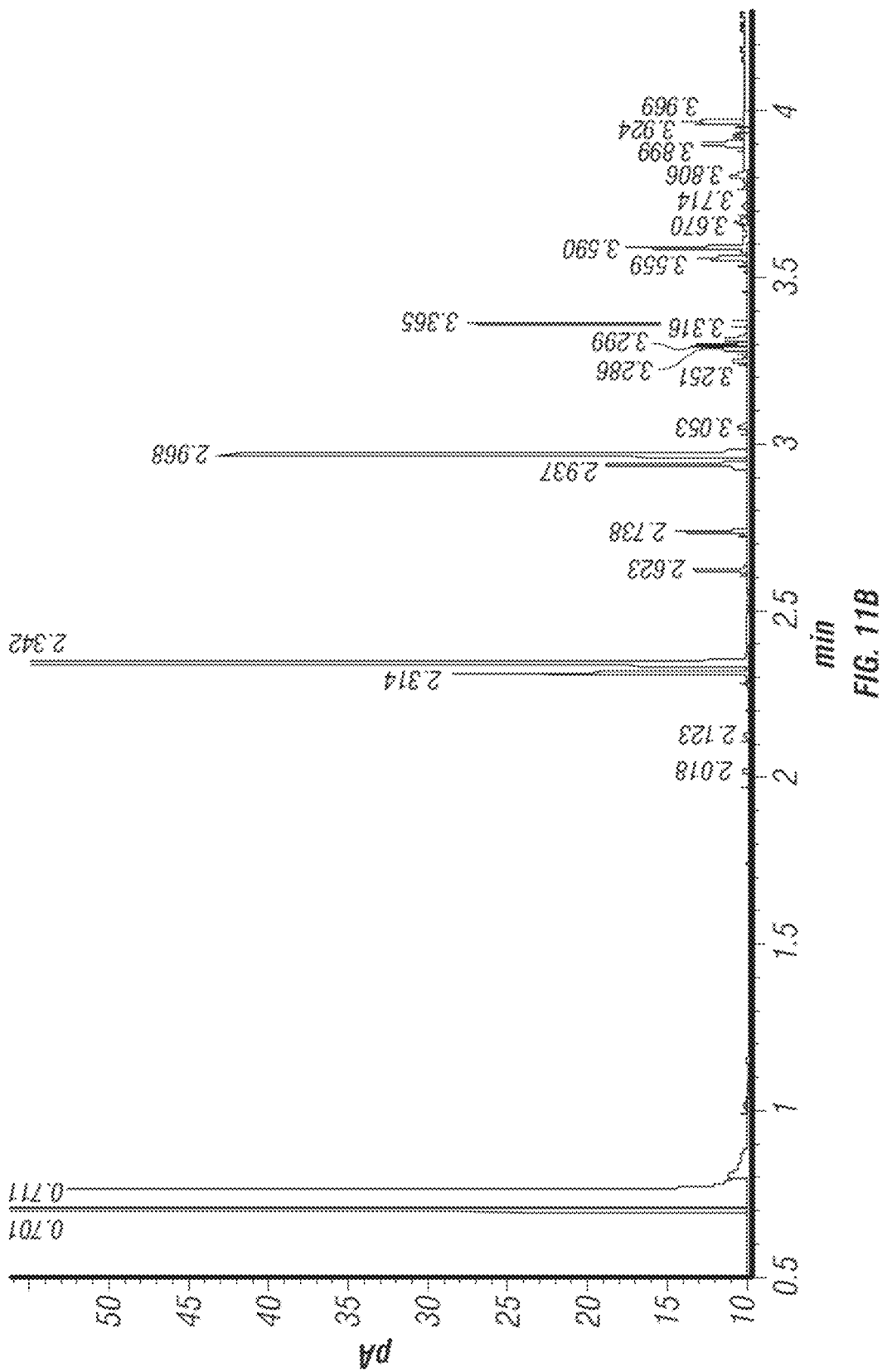
Figure 12A:
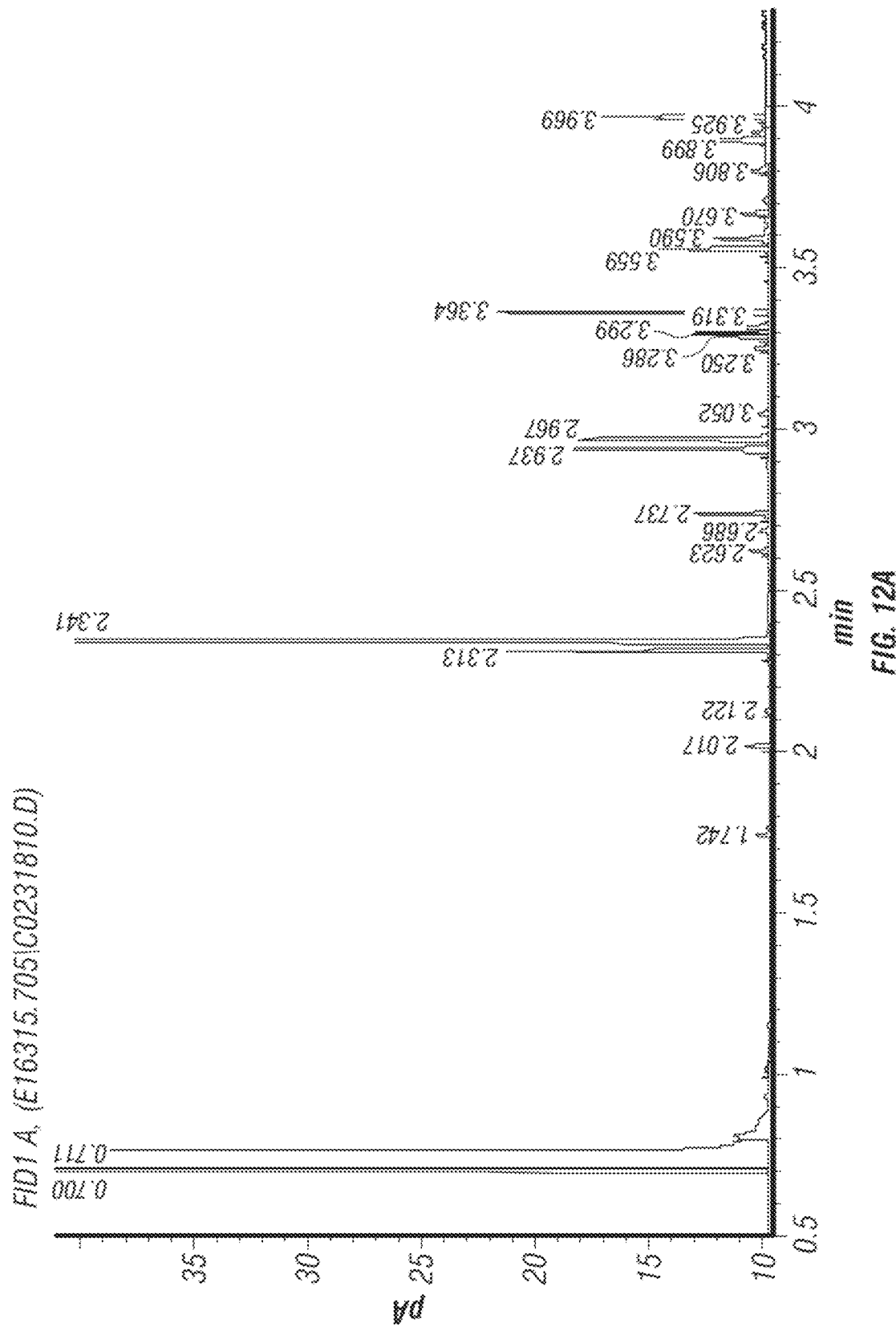
FIG. 12A-B. Chromatograms showing results of FAME analysis of *S. hominis* strains A9 and C2, which were identified by the methods given in the present disclosure.
Figure 12B:
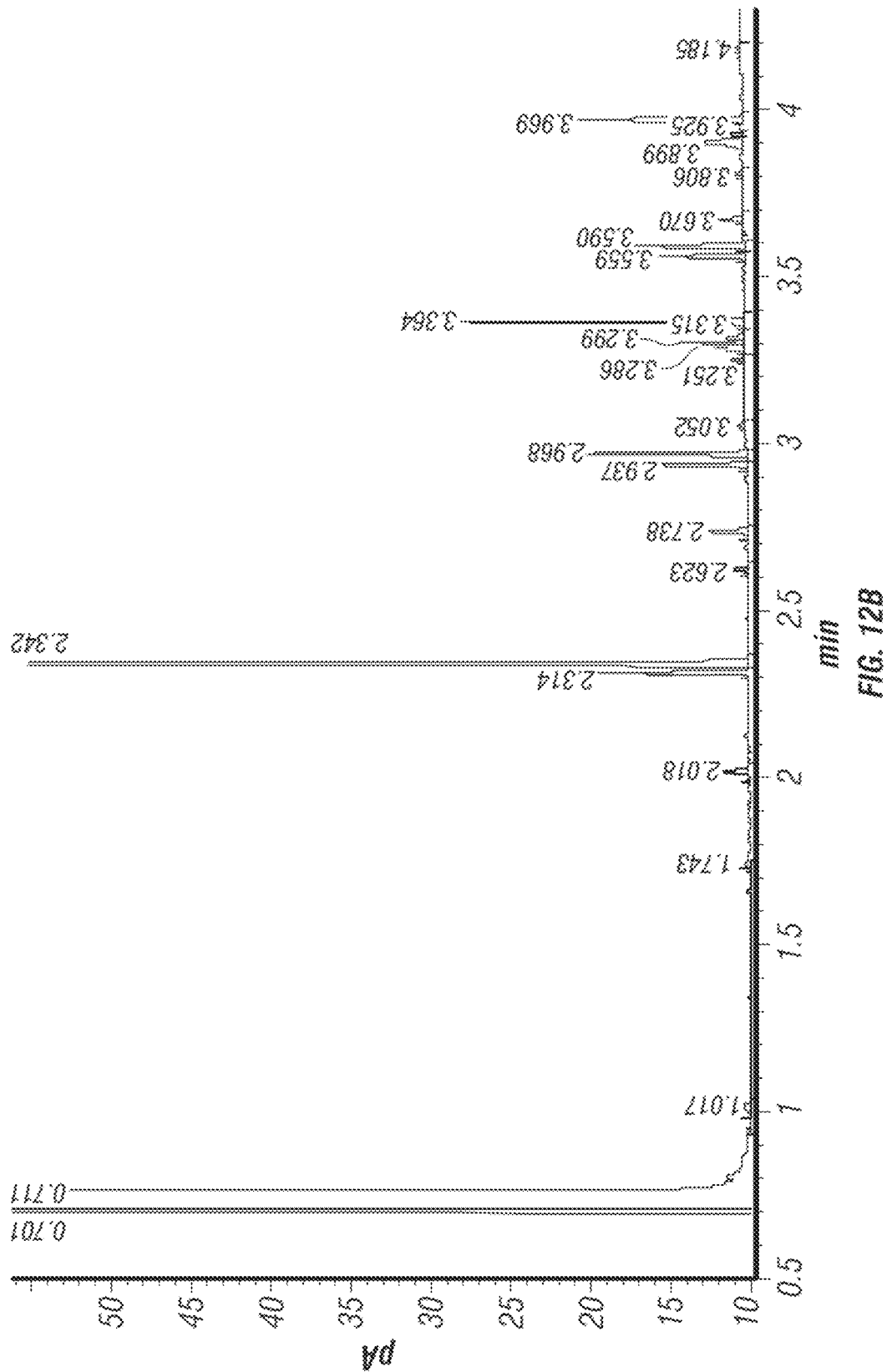
Figure 13A:
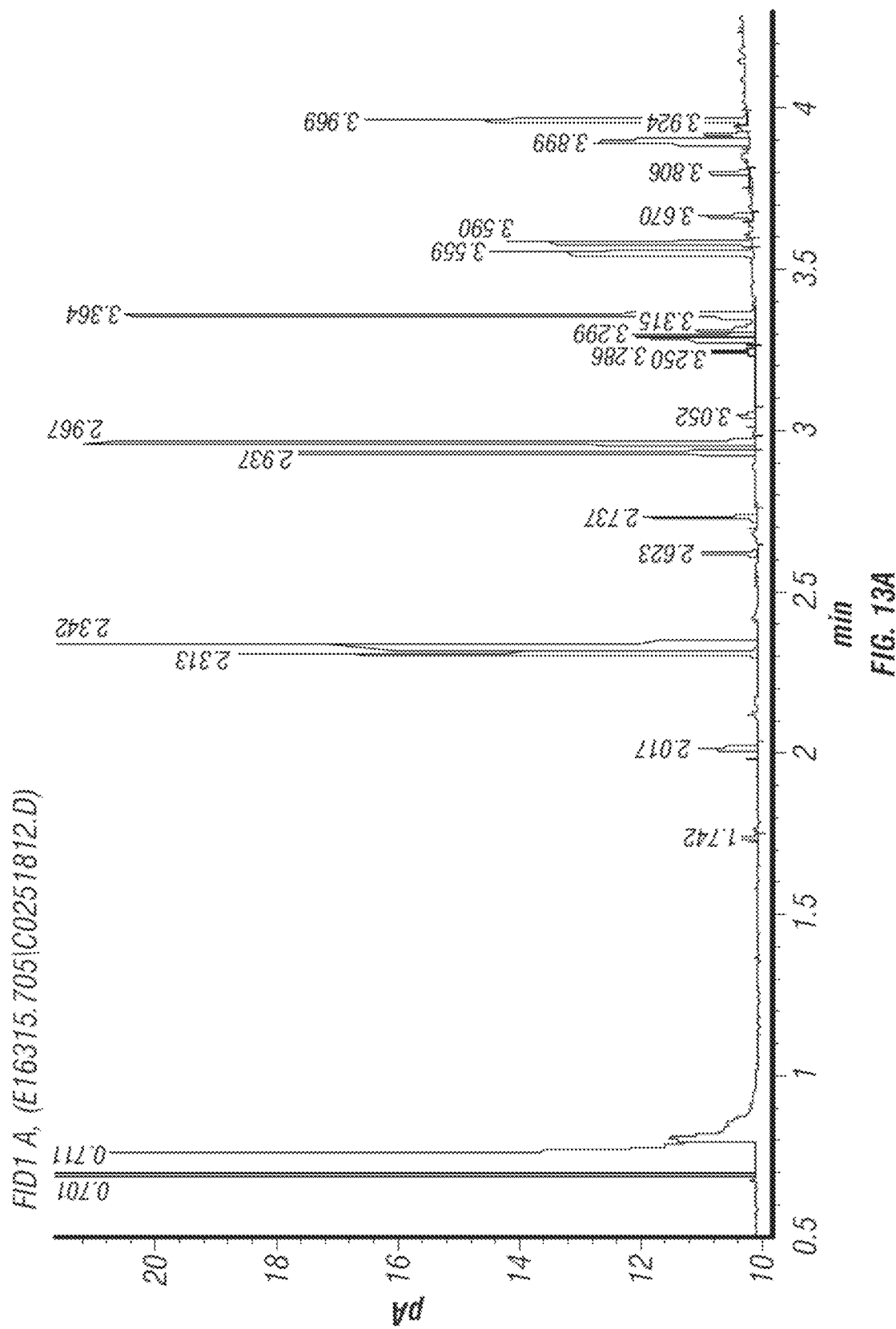
FIG. 13A-B. Chromatograms showing results of FAME analysis of *S. epidermidis* strains A11 and AMT1-A9, which were identified by the methods given in the present disclosure.
Figure 13B:
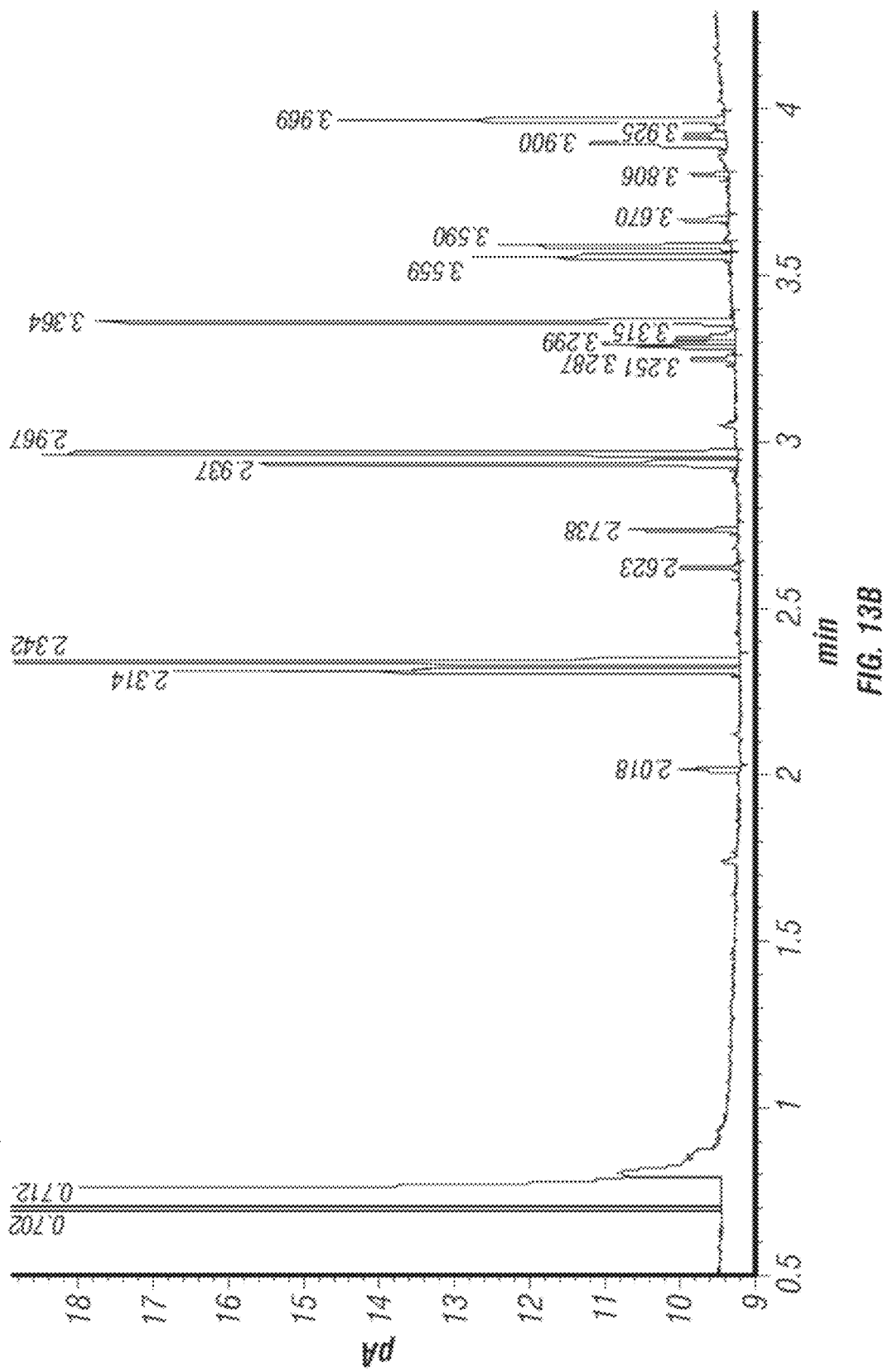
Figure 14A:
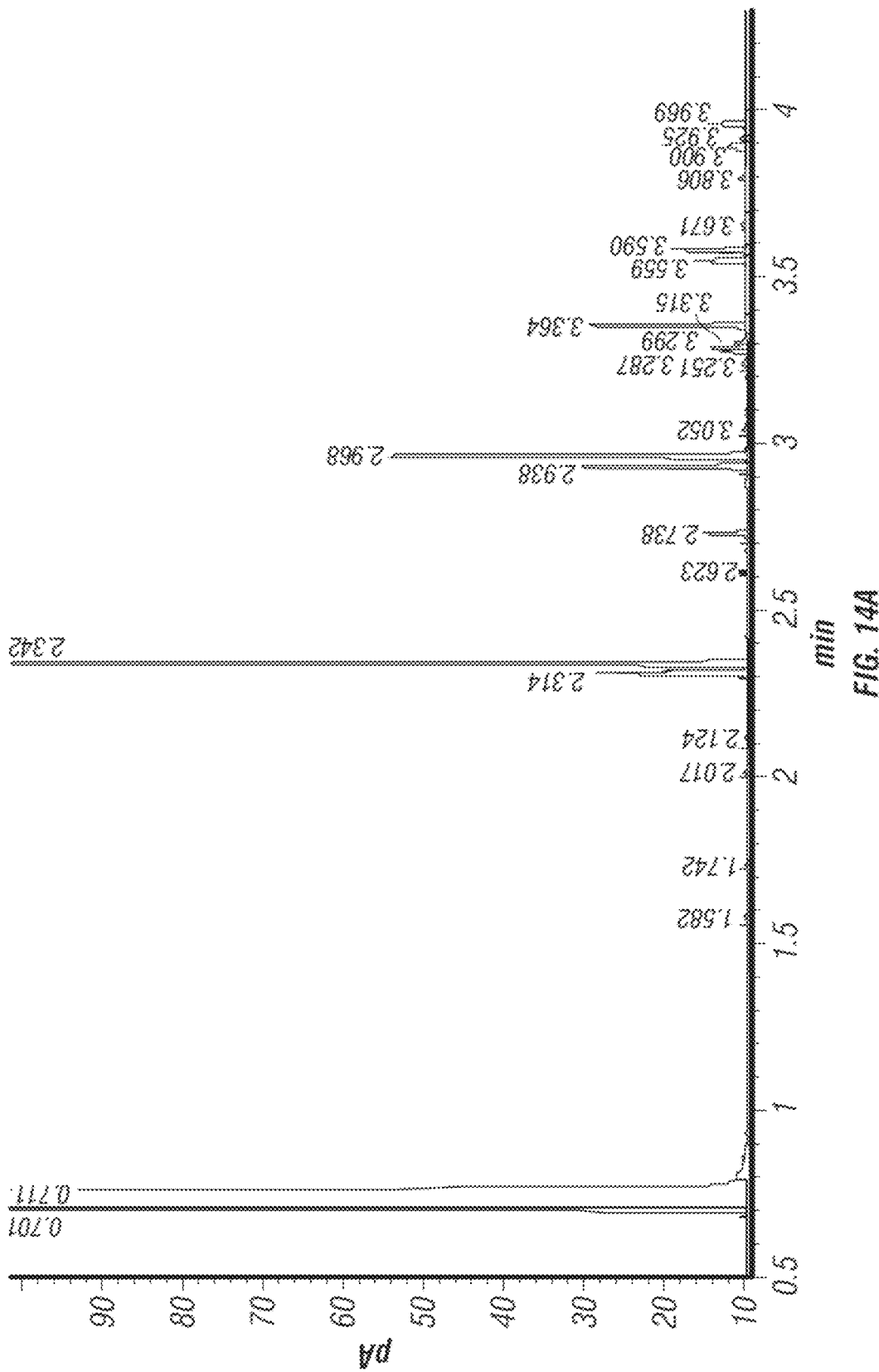
FIG. 14A-B. Chromatograms showing results of FAME analysis of *S. hominis* strains AMT2-A11 and AMT3-A12, which were identified by the methods given in the present disclosure.
Figure 14B:
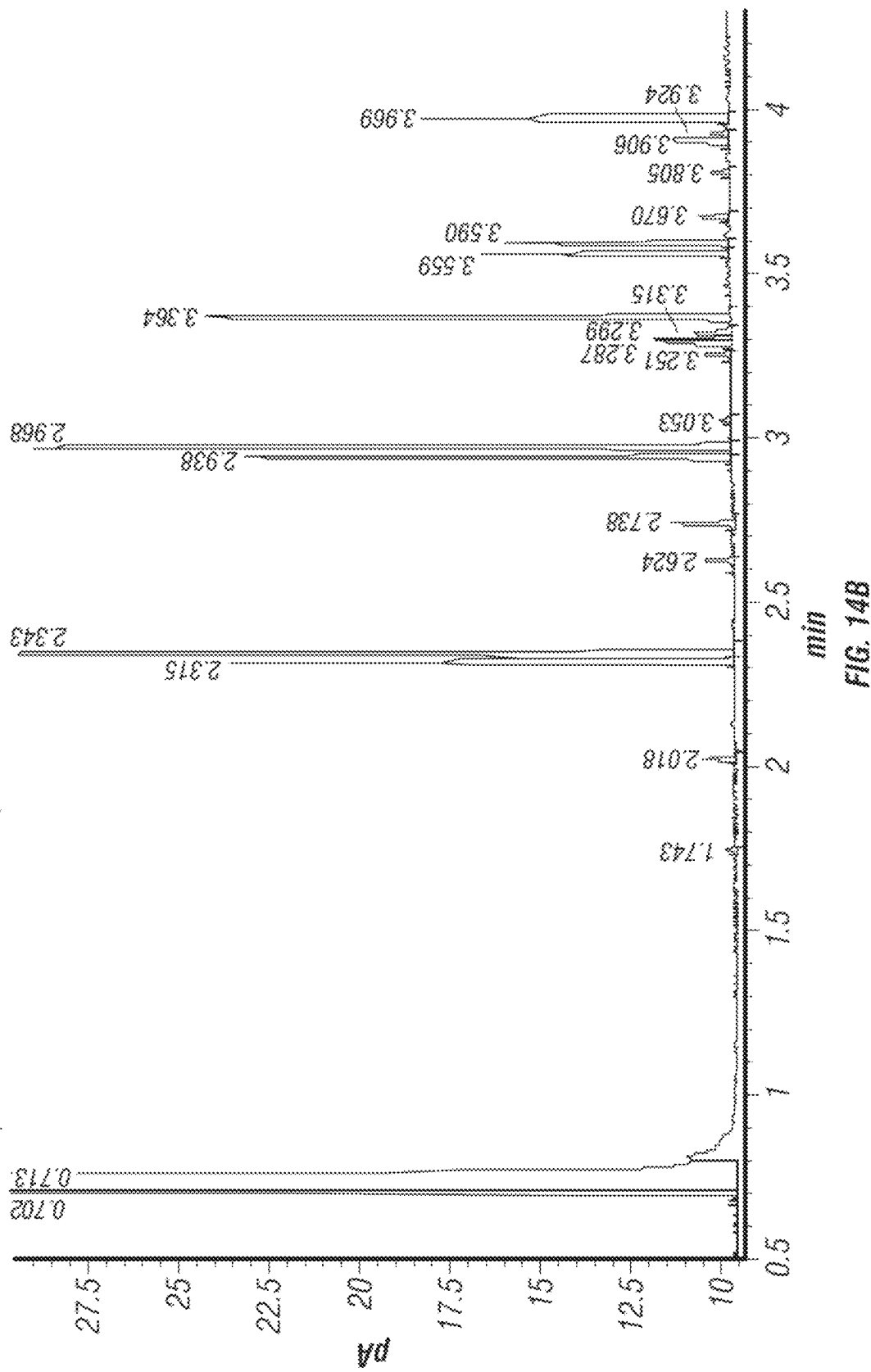
Figure 15A:
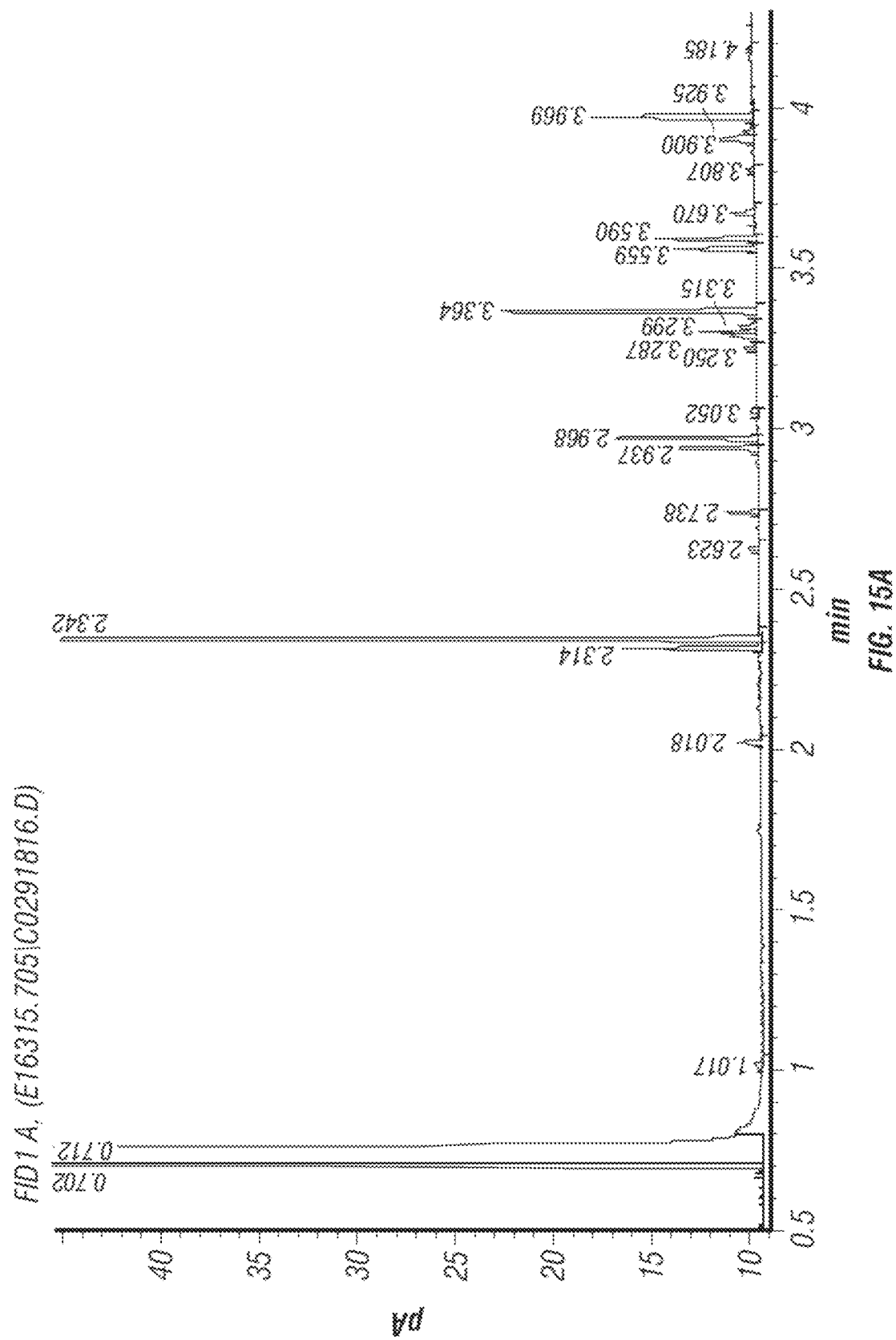
FIG. 15A-B. Chromatograms showing results of FAME analysis of *S. hominis* strains AMT4-C2 and AMT4-G1, which were identified by the methods given in the present disclosure.
Figure 15B:
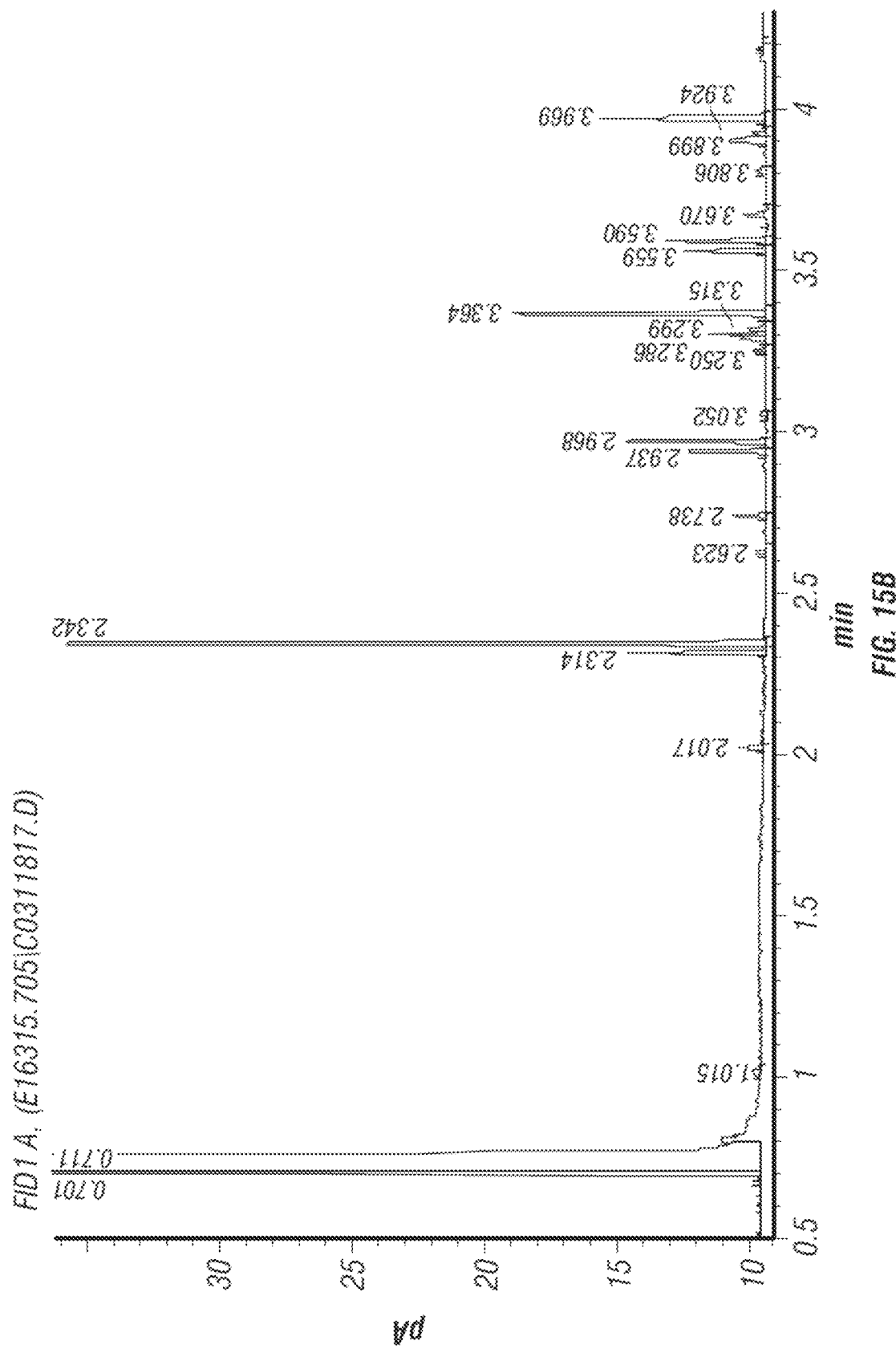
Figure 16A:
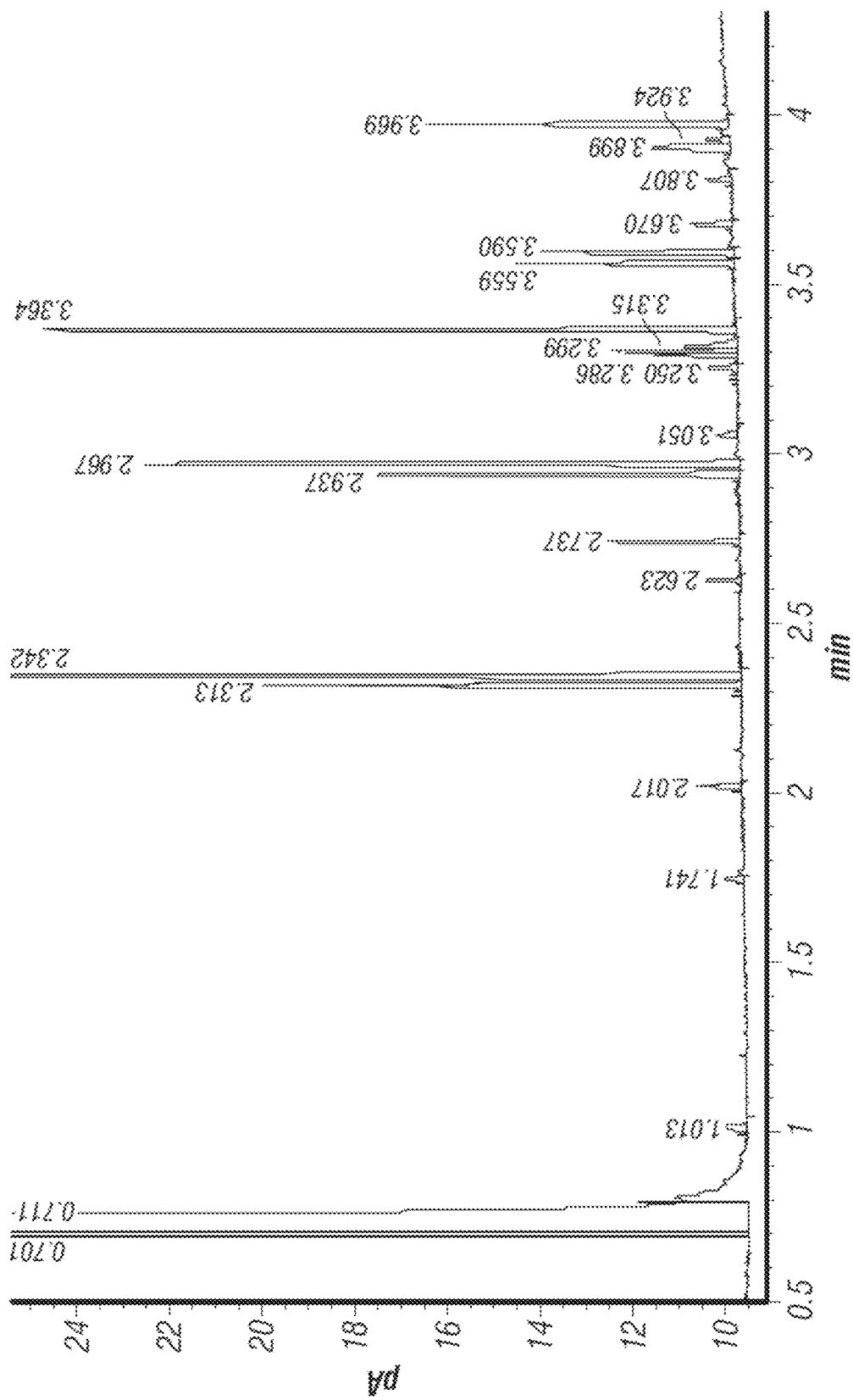
FIG. 16A-B. Chromatograms showing results of FAME analysis of *S. hominis* strains AMT4-D12 and *S. epidermidis* AMT5-C5, which were identified by the methods given in the present disclosure.
Figure 16B:
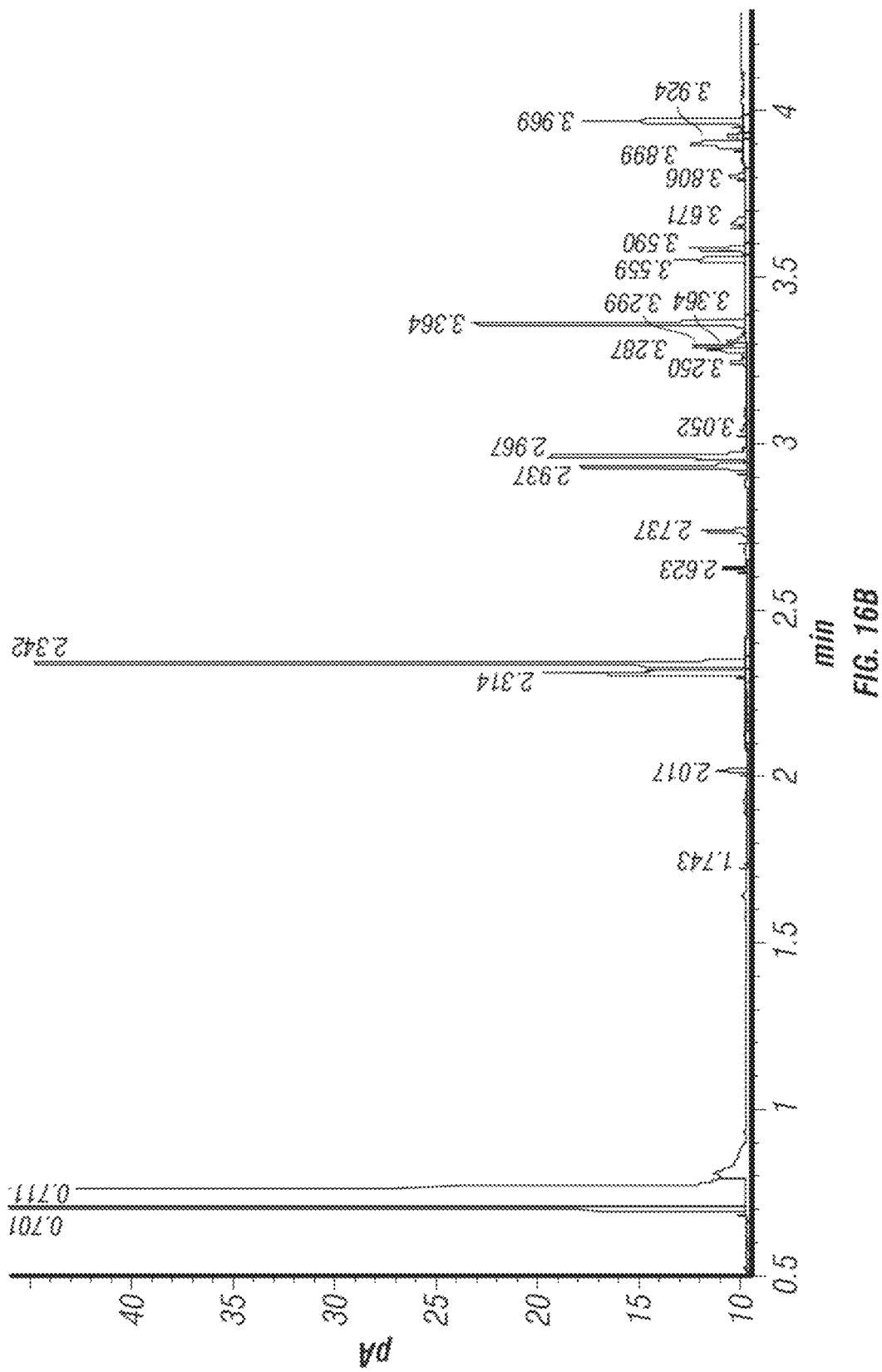
Figure 17A:
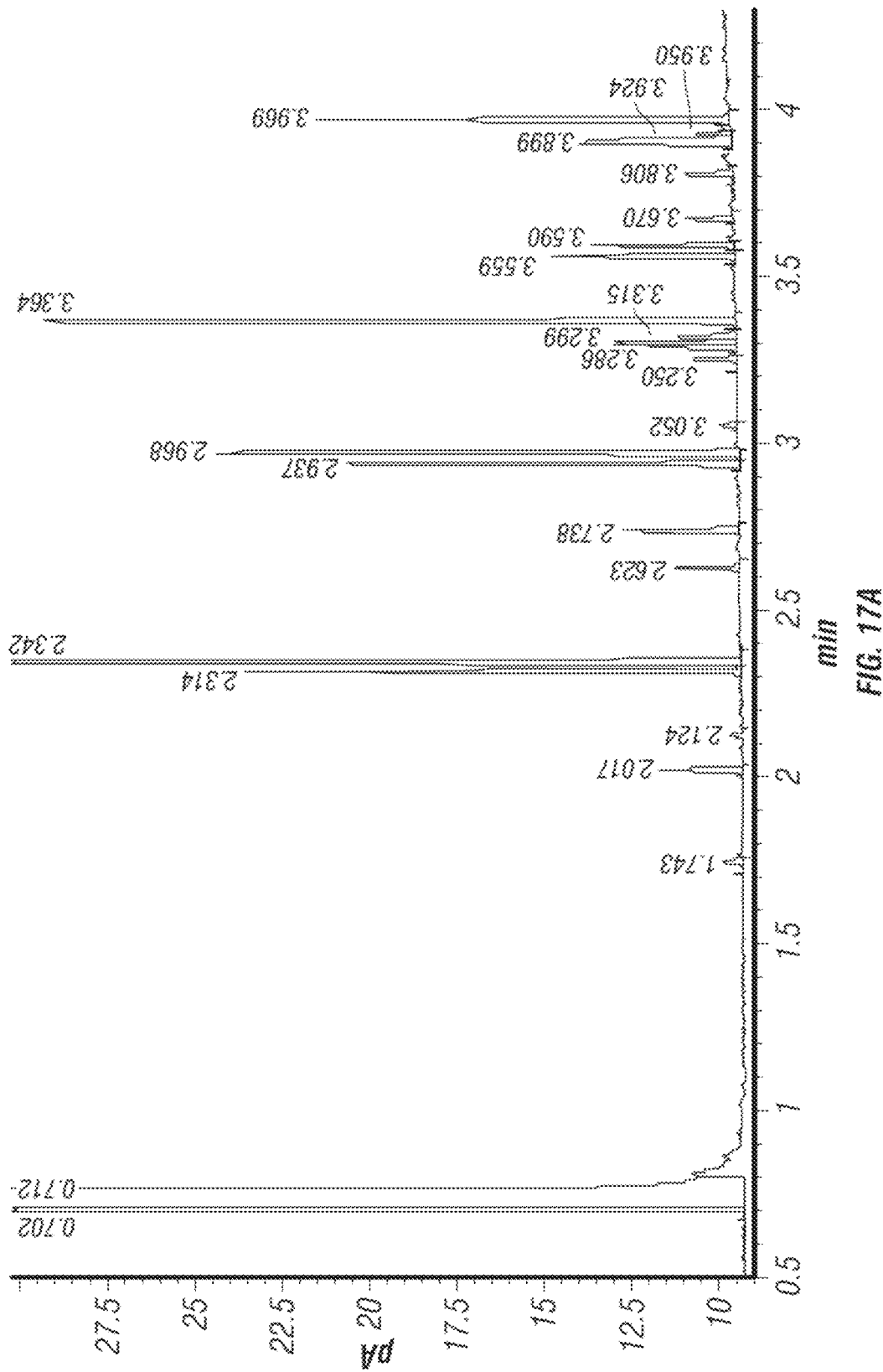
FIG. 17A-B. Chromatograms showing results of FAME analysis of *S. epidermidis* strain AMT5-G6, which was identified by the methods given in the present disclosure, and *S. hominis* strain C4, which does not produce hogocidin.
Figure 17B:
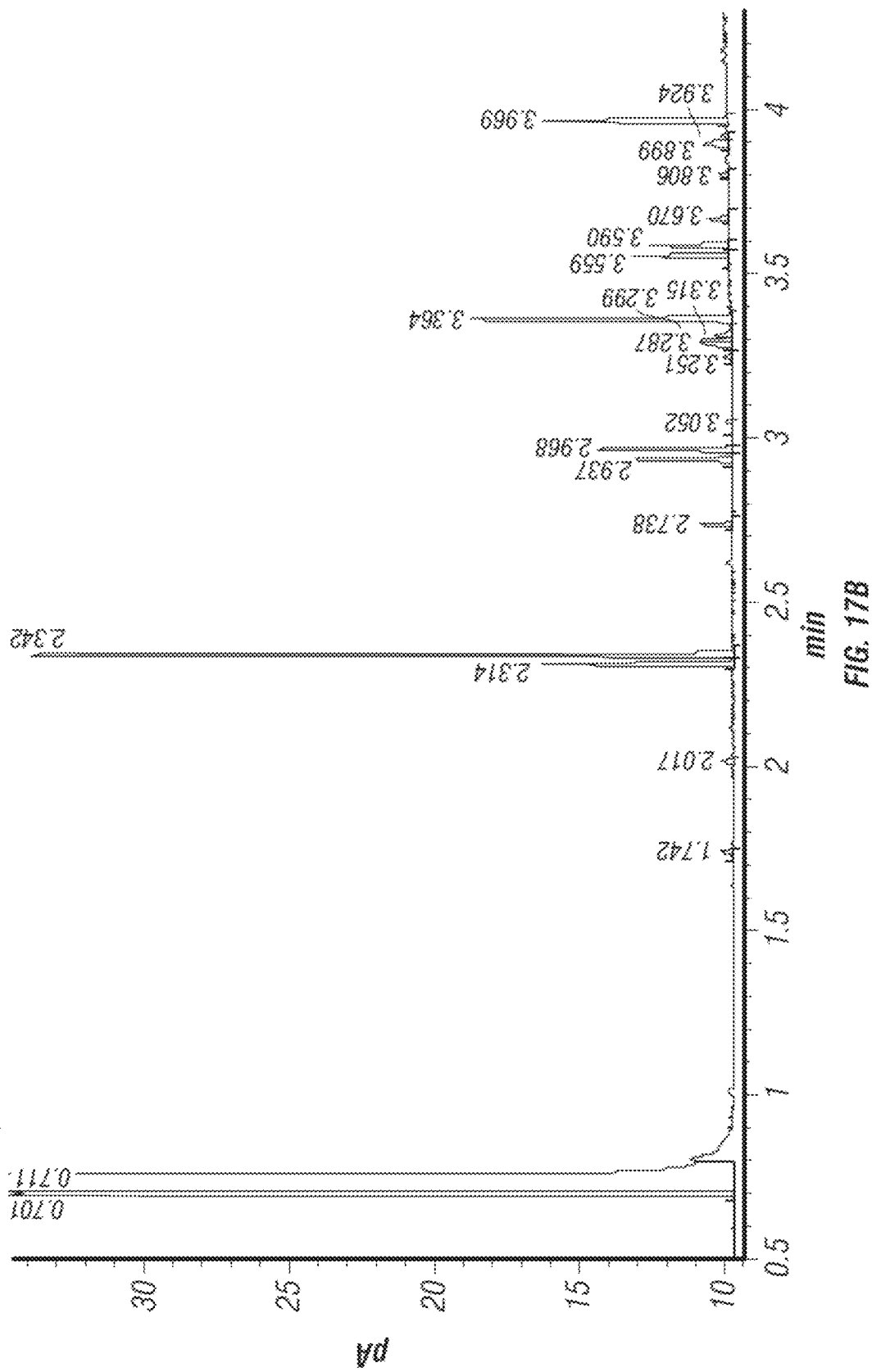
Figure 16A:
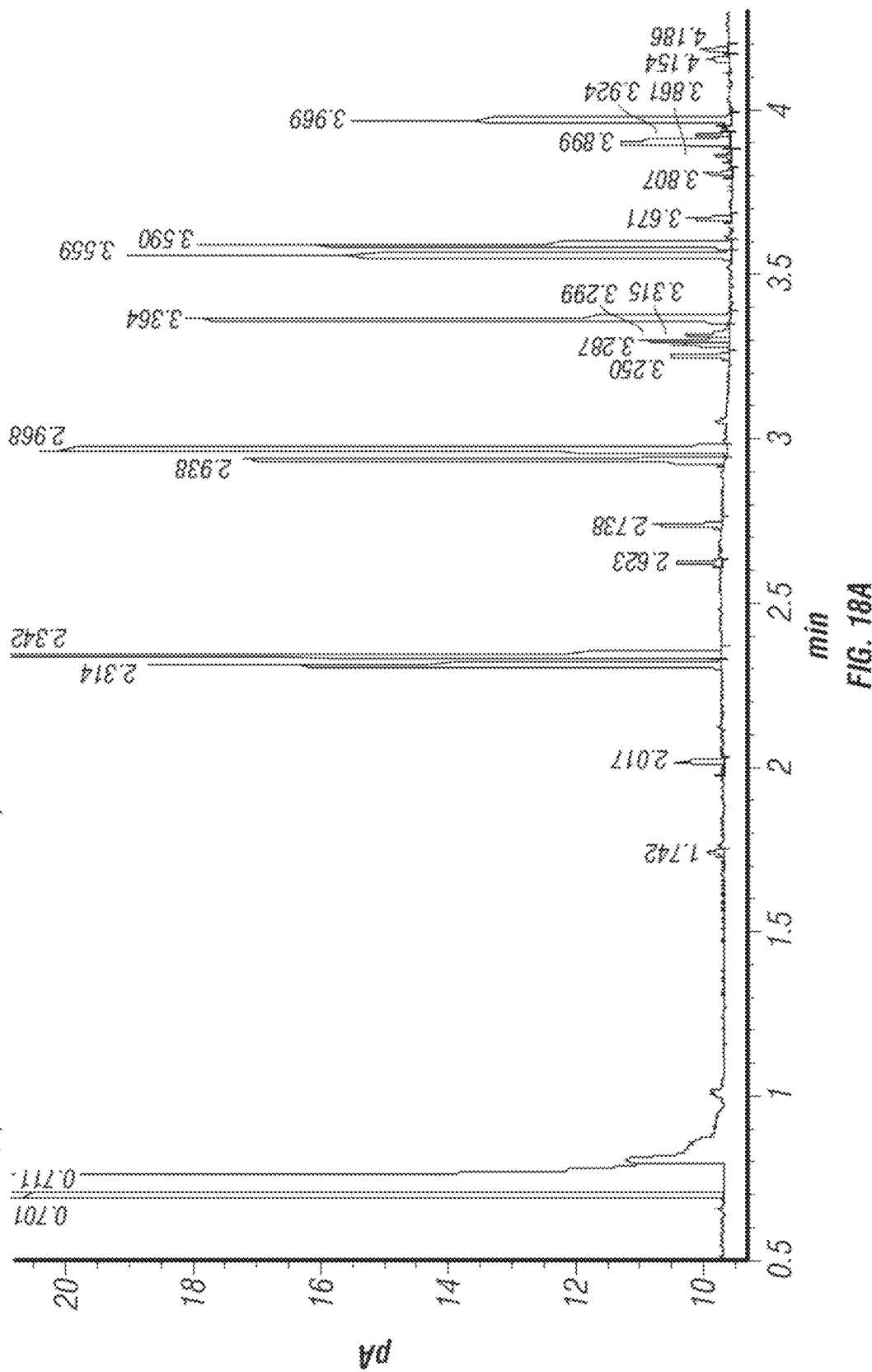
Figure 18B:
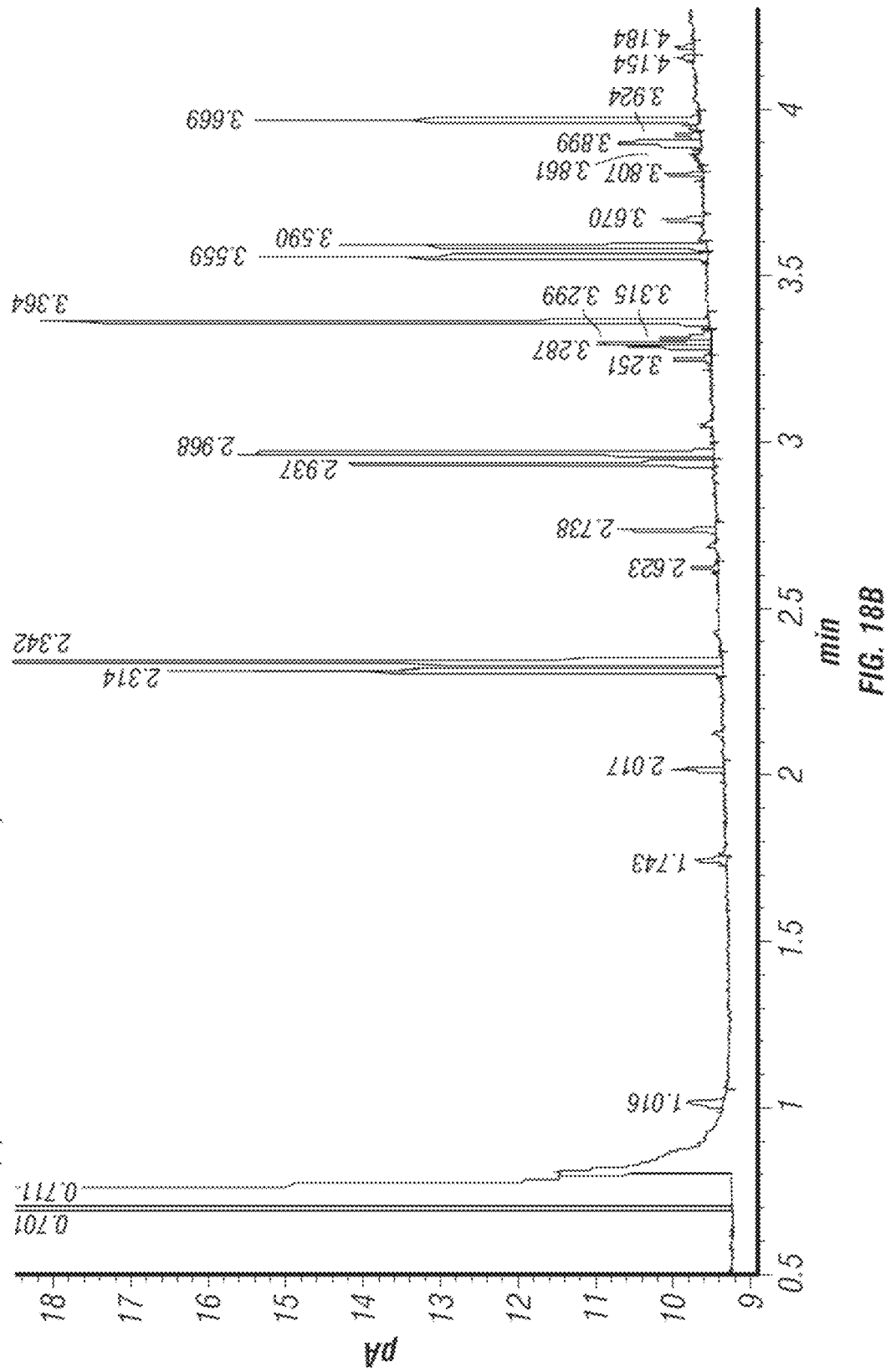
Figure 19:
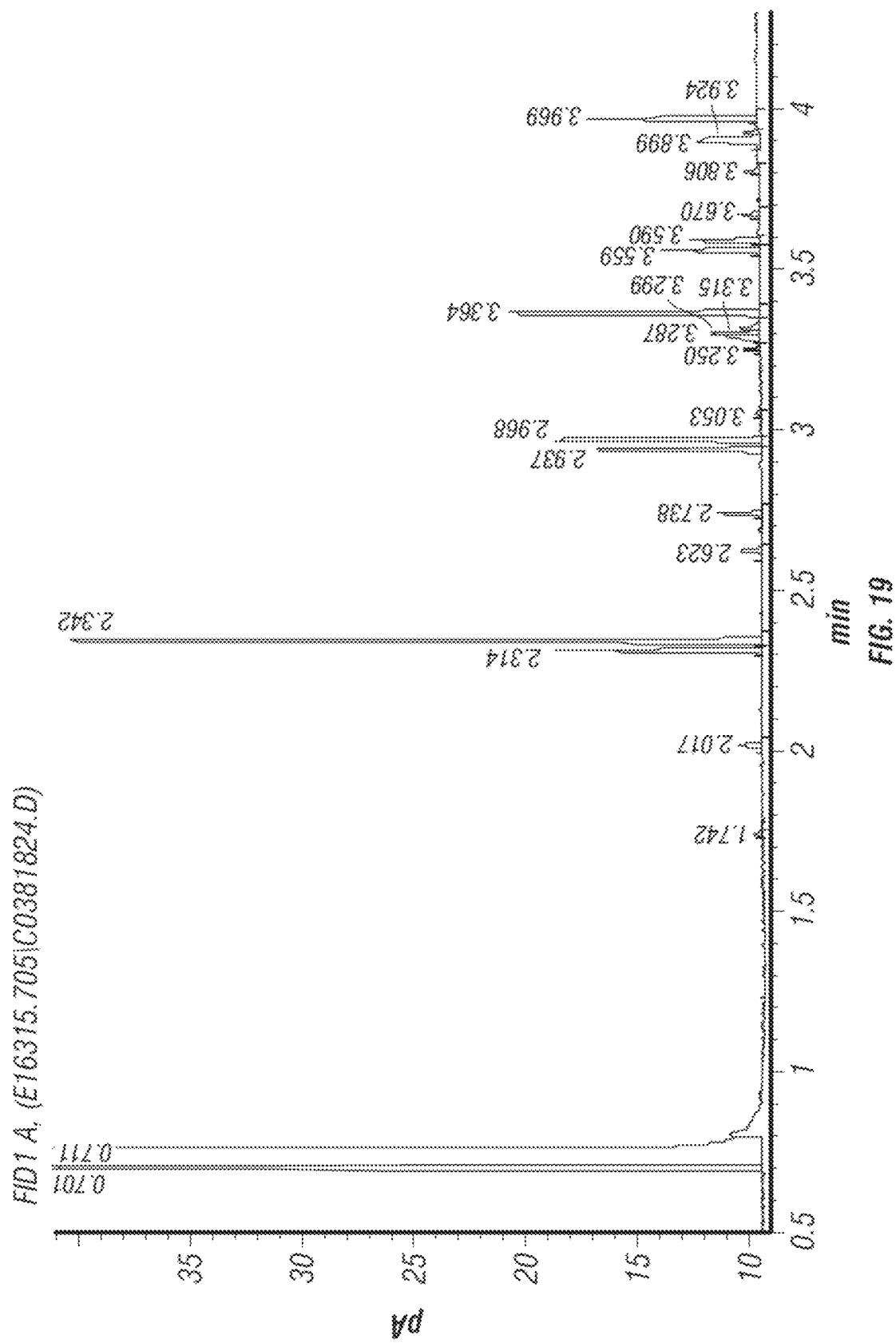
FIG. 19. Chromatogram showing results of FAME analysis of *S. epidermidis* strain MO1, which does not produce SE-lantibiotics or SE-antimicrobials.

Protein sequencing by MALDI-TOF/TOF analysis. Because the N-terminal region of Hogocidin-β from *S. hominis* (Fraction 32, FIG. 8) contains modified amino acids, sequence could not be obtained by Edman degradation. Therefore, whole protein sequence of this AMP was obtained based on genome guided MALDI-TOF/TOF analysis. The analysis of nucleotide sequence of *S. hominis* was performed on antibiotics and secondary metabolite analysis shell—AntiSMASH platform in order to identify secondary metabolites biosynthesis gene clusters. AntiSMASH results provided one gene cluster for lantipeptides with a potential candidate at locus 2050-2250 (FIG. 9A). NCBI BlastP analyses of genes involved in synthesis and modification show high homology to the class 2 lantipeptide. A core peptide with sequence ATPTITTSSATCG-GIIVAASAAQCPTLACSSRCGKRKK (SEQ ID NO:4 from aa 29 to 66) cleaved from leader peptide with a GG cleavage site, common for type 2 lantibiotics. Combining genome mining and MS/MS fragmentation predicted a mature form of Hogocidin-β (FIG. 5A).

Genome Sequencing. Because the protein sequences of AMPs from *S. hominis* did not match to any molecules found in the existing genome database, whole genome sequence of the antimicrobial strain of *S. hominis* was performed. Genomic DNA was purified using UltraClean® Microbial DNA Isolation kit (MO Bio). Whole genome DNA sequencing libraries were constructed using the Nextera-XT DNA Sample Prep Kit (Illumina) following the vendor's protocol. The final library was sequenced by paired end sequencing (300×300) on an Illumina MiSeq™. Sequenced reads were de novo assembled using SPAdes 2.5.1 with k-mers of lengths 21, 33, 55, 77, and 127 and the flag for "careful" turned on. On all of the produced scaffolds, a six-frame translation was performed using translate Whole Genome Multi Chromosome.pl (available at proteomics.ucsd.edu/Downloads/). This output was then queried for a match to the peptide fragment identified via mass spectrometry.

Antimicrobial assays. Radial diffusion assay was performed using S. aureus (ATCC35556) strain to test antimicrobial activity of purified fractions. Briefly, melted TSB agar (10 mL) was mixed with S. aureus ($1 \times 10^6$ CFU) and poured in a 10 cm petri dish. Two to four μL of test samples was applied in a small well punched on the agar plate. Plates were incubated at 37° C. overnight to allow visible growth of bacteria. Antibacterial activity was indicated by the clear zone (no bacterial growth) around the well. Antimicrobial activity of Hogocidins was evaluated by incubating S. aureus ($1 \times 10^5$ CFU/mL) with 2-fold serial dilutions of purified Hogocidins in half strength Muller-Hinton broth (MHB) in PBS at 37° C. for 24 hrs. After incubation, the number of viable bacteria was measured by counting CFU after spreading 10-fold serial dilutions of bacteria on TSB agar plates. MBC was determined as a 3-log reduction (99.9%) of viable bacteria after 24 hour incubation.

Statistical analysis. Paired t-tests were used to compare lesional to non-lesional samples within atopic subjects and independent t-tests were used to compare non-atopic to atopic samples. Longitudinal mixed models of frequency of antimicrobial CoNS and the ratio of live Staphylococcus to Staphylococcus DNA over time were also fit. Each model included lesion type, visit, and their interaction term as fixed effects, while a compound symmetry structure was used to account for correlation between samples obtained from the same subject at multiple time points. Frequency of antimicrobial CoNS used a cumulative log it link and multinomial distribution of categorized percentages (<=20, 21-79, >=80) to account for a bi-modal distribution. Statistical analyses were performed using SAS (version 9.3) software.

Figure 1B:
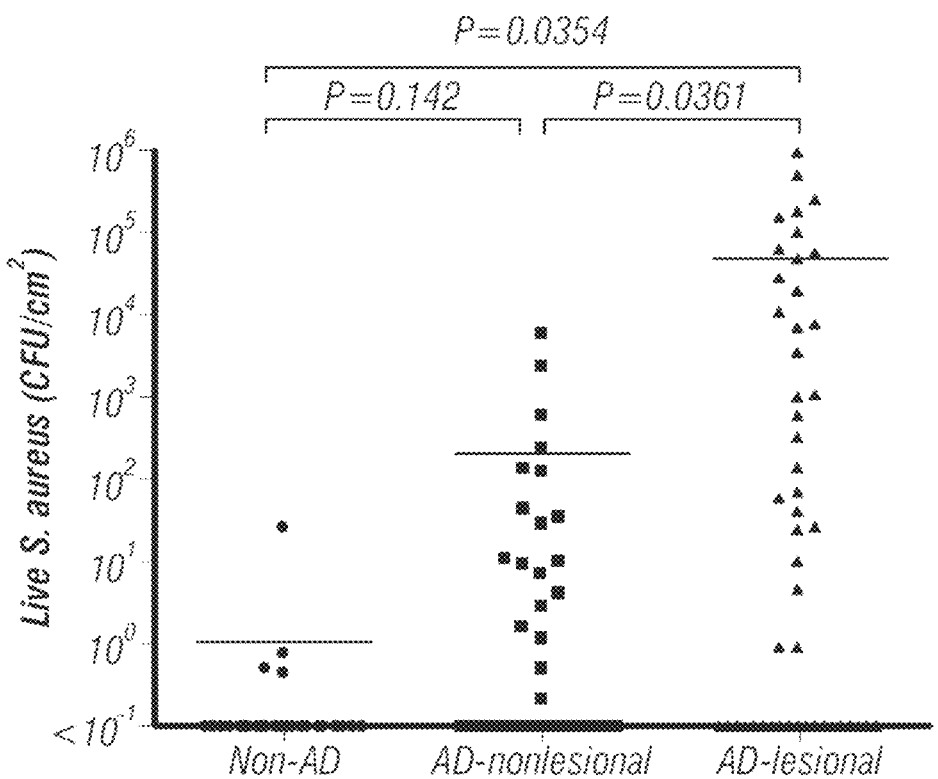
Figure 1C:
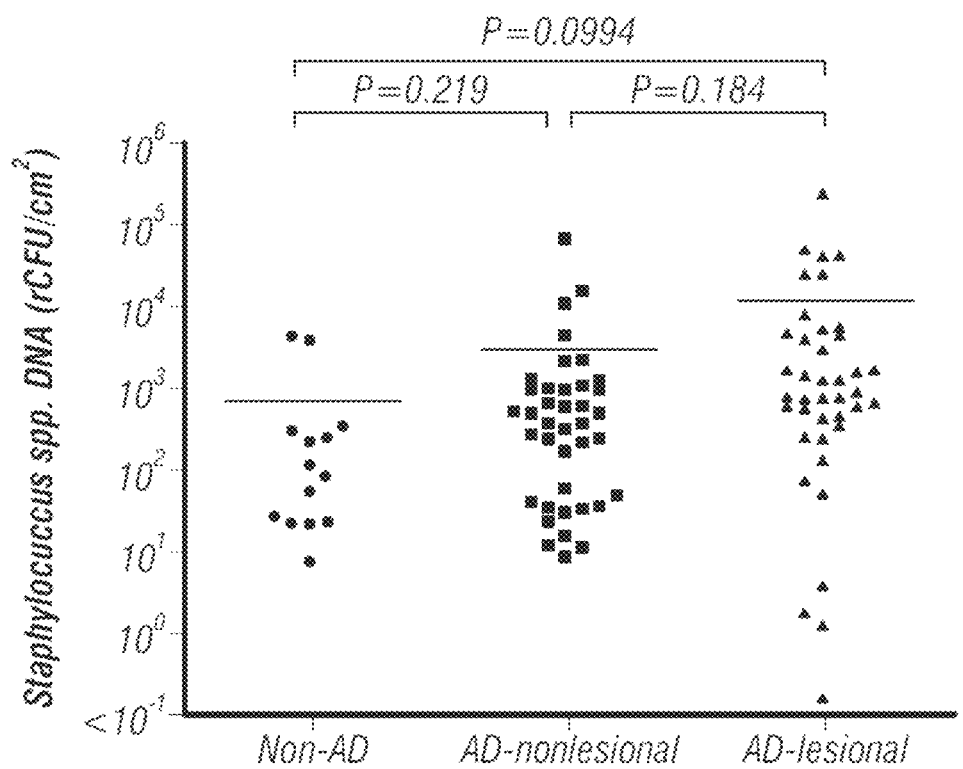
Figure 1D:
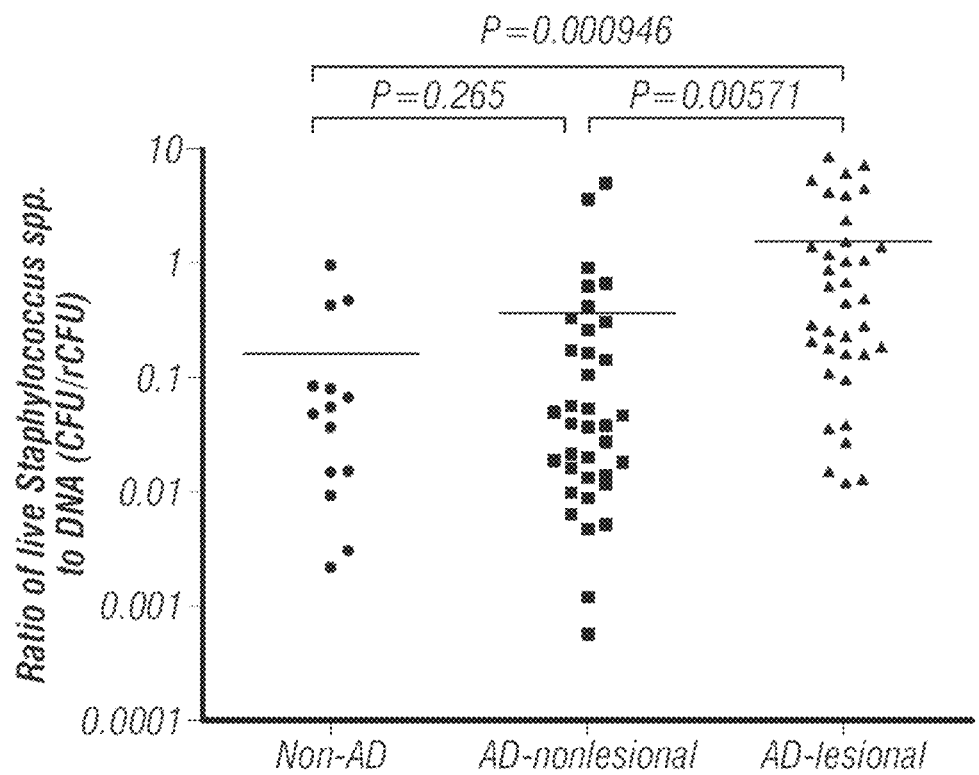
Figure 6:
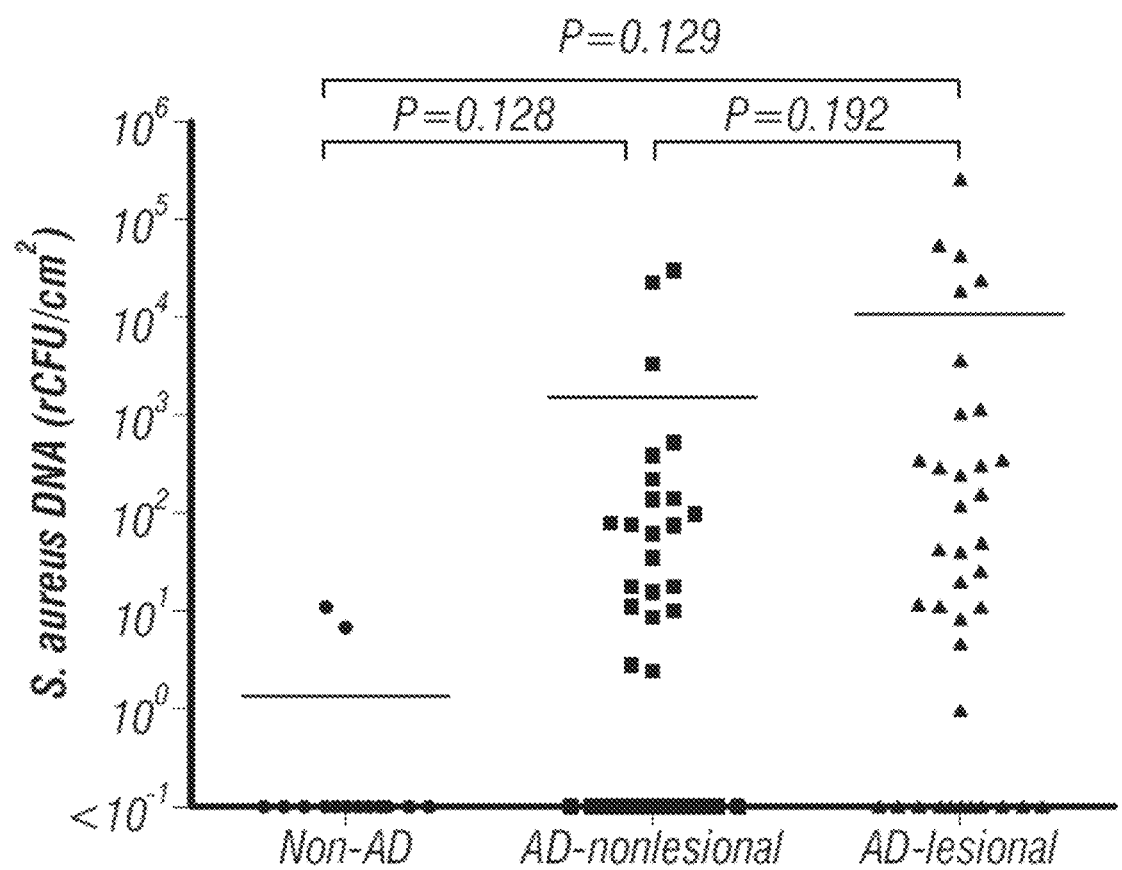
FIG. 6. Abundance of *S. aureus* DNA on non-atopic skin, nonlesional and lesional site of atopic skin. Fourteen and 37 DNA swabs were obtained from 30 normal and 50 atopic dermatitis patients recruited, respectively. The abundance of *S. aureus* DNA was determined by qPCR with species-specific primers targeting the *S. aureus*-specific femA gene. Relative CFU (rCFU) of *S. aureus* DNA was determined by comparison with known CFUs of *S. aureus* (ATCC35556). Density of live bacteria or bacterial DNA was normalized into the area swabbed. AD: atopic dermatitis.

Staphylococcus survival is increased in atopic dermatitis. To assess the relationship between the amount of culturable/live Staphylococcus spp. and unculturable/dead Staphylococcus spp. bacterial density was measured by both manual colony counting and qPCR for genus-specific 16S ribosomal DNA. Consistent with prior reports, more total Staphylococcus spp. and S. aureus could be cultured from lesional skin on the forearms of patients with atopic dermatitis than from nonlesional skin of these patients or non-atopic subjects (FIGS. 1A and 1B). Measurements of DNA abundance revealed a similar trend (FIGS. 1C and 6). However, the results of these two independent techniques differed significantly between atopic lesional skin and non-atopic skin. In lesional skin of subjects with atopic dermatitis, culture and DNA based results were similar (FIG. 1D). In contrast, in non-atopic skin the ratio of cultured CFU to relative CFU based on DNA abundance was approximately 0.1, suggesting a lower survival rate of bacteria on the skin of non-atopic subjects.

Antimicrobial activity of the skin microbiome. Live CoNS from 30 non-atopic (2029 colonies) and 50 atopic subjects (5695 colonies) were isolated to characterize their influence on S. aureus survival. A majority of CoNS clones isolated from nonatopic subjects (75.26±35.49%) were observed to inhibit S. aureus growth (FIG. 2A). In contrast, a minority of the CoNS found on atopic skin possessed this activity [22.83±32.64% (nonlesional) and 15.76±25.92% (lesional)]. This difference in the antimicrobial function of CoNS isolated from each population was stable and reproducible over time as seen following repeated swabs over a 2 week period (FIG. 2B). The increased ratio of culturable Staphylococcus to total Staphylococcus DNA was also stable in this cohort over a 2 week period (FIG. 2C). These data suggest that although the skin of patients with atopic dermatitis supports growth of CoNS bacteria, it enables survival of strains that differ in antimicrobial function from those found on non-atopic skin.

Figure 3A:
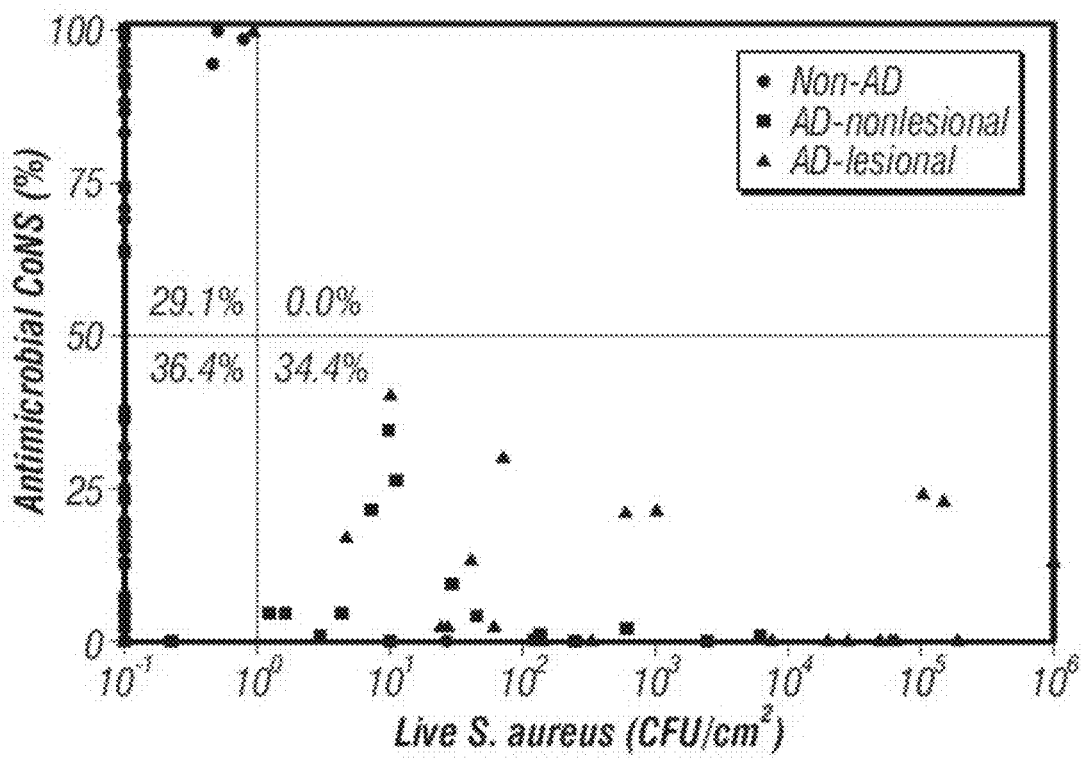
FIG. 3A-B. Antimicrobial coagulase-negative Staphylococcus correlate with the absence of S. aureus colonization.
Figure 3B:
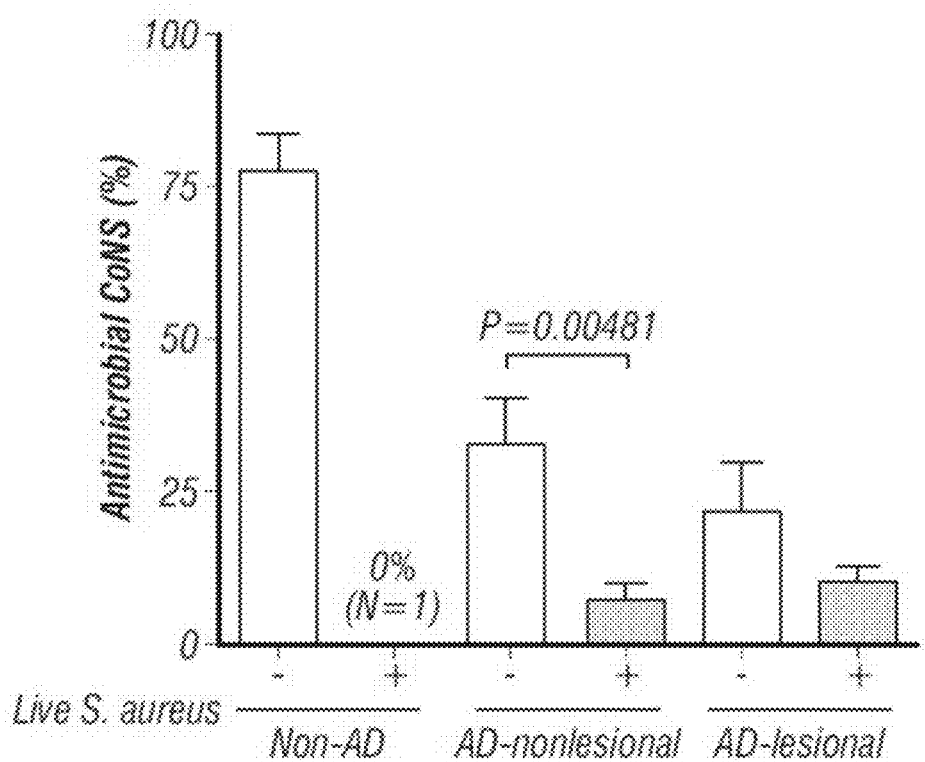

As shown in FIG. 1, only 3% of non-atopic subjects were S. aureus culture-positive (>1 CFU/$cm^2$), whereas 57% of atopic subjects cultured positive for S. aureus. To determine if the antimicrobial activity detected from CoNS was related to S. aureus survival the frequency of antimicrobial CoNS to measurements of live S. aureus was compared (FIG. 3A). Strikingly, all patients with live S. aureus had a low frequency of antimicrobial CoNS. In addition, the frequency was lower in S. aureus culture-positive group (>1 CFU/$cm^2$) than in S. aureus-negative group (FIG. 3B). These data suggest that antimicrobial CoNS were protective against S. aureus colonization.

Figures 4A, 4B:
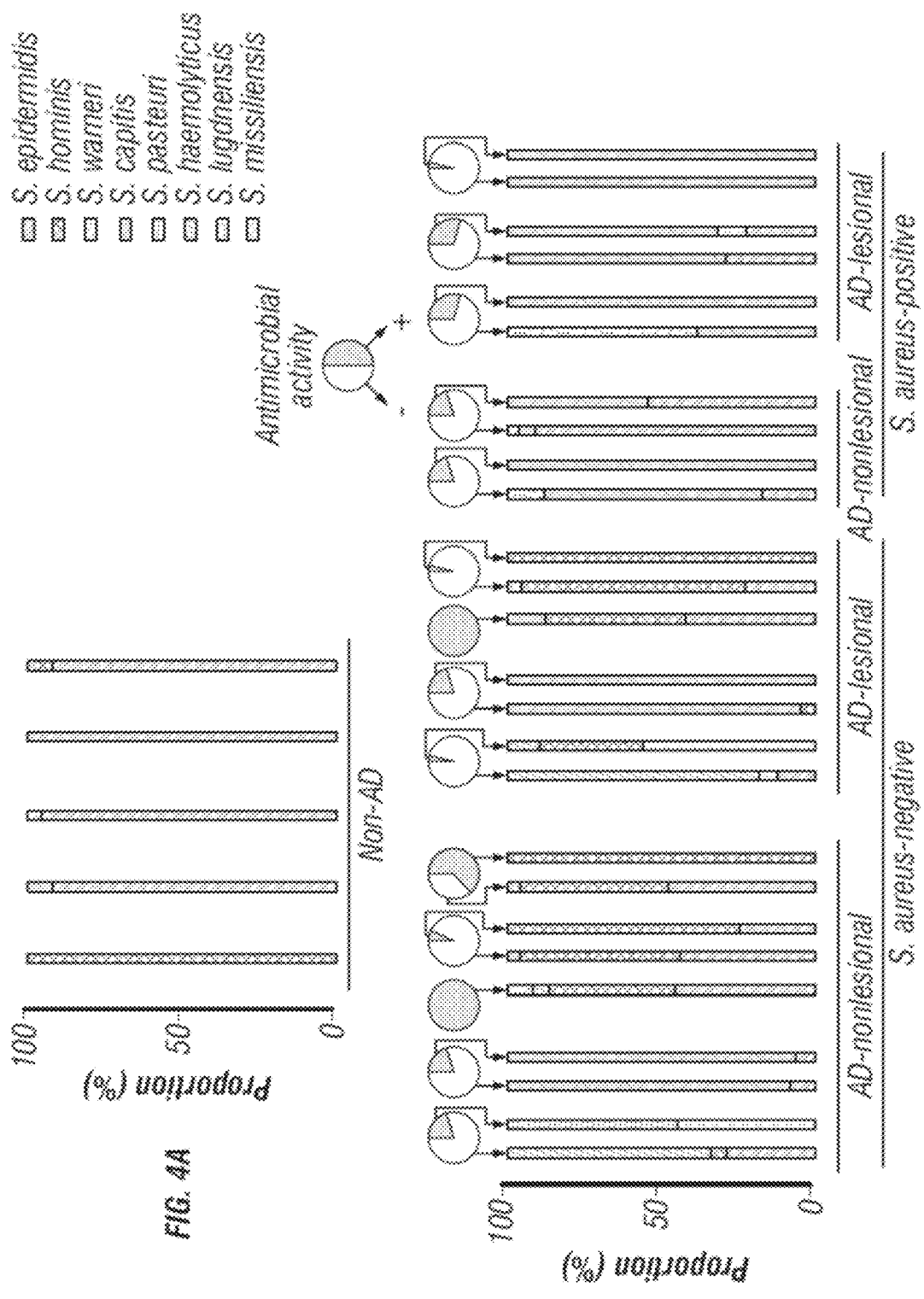
FIG. 4A-B. Diverse bacterial species have antimicrobial activity. Species of antimicrobial or non-antimicrobial CoNS were identified by DNA sequencing of full length 16S rRNA from randomly isolated colonies with and without antimicrobial activity.

Identification of antimicrobial bacterial species on the skin. To further identify the CoNS species with antimicrobial activity, a random subset of bacterial colonies were selected for full-length 16S rRNA gene sequencing. In non-atopic skin, the predominant species of antimicrobial CoNS were S. epidermidis or S. hominis (FIG. 4A). In the atopic subjects, antimicrobial CoNS members included Staphylococcus pasteuri, Staphylococcus warneri Staphylococcus capitis, S. epidermidis and S. hominis. However, in most subjects, similar species were identified within groups found to have antimicrobial and non-antimicrobial function (FIG. 4B). These observations show that antimicrobial activity is not predictable at the species level. Overgrowth of functionally inactive CoNS strains appears to occur in patients with atopic dermatitis.

Figure 7B:
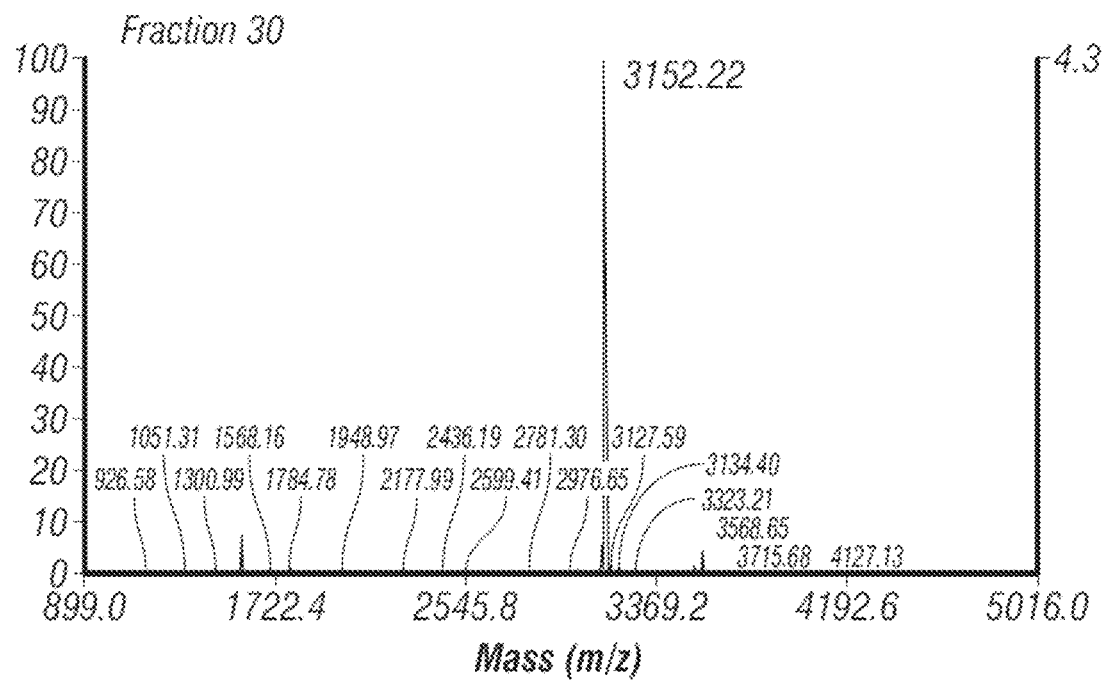
Figure 7B:
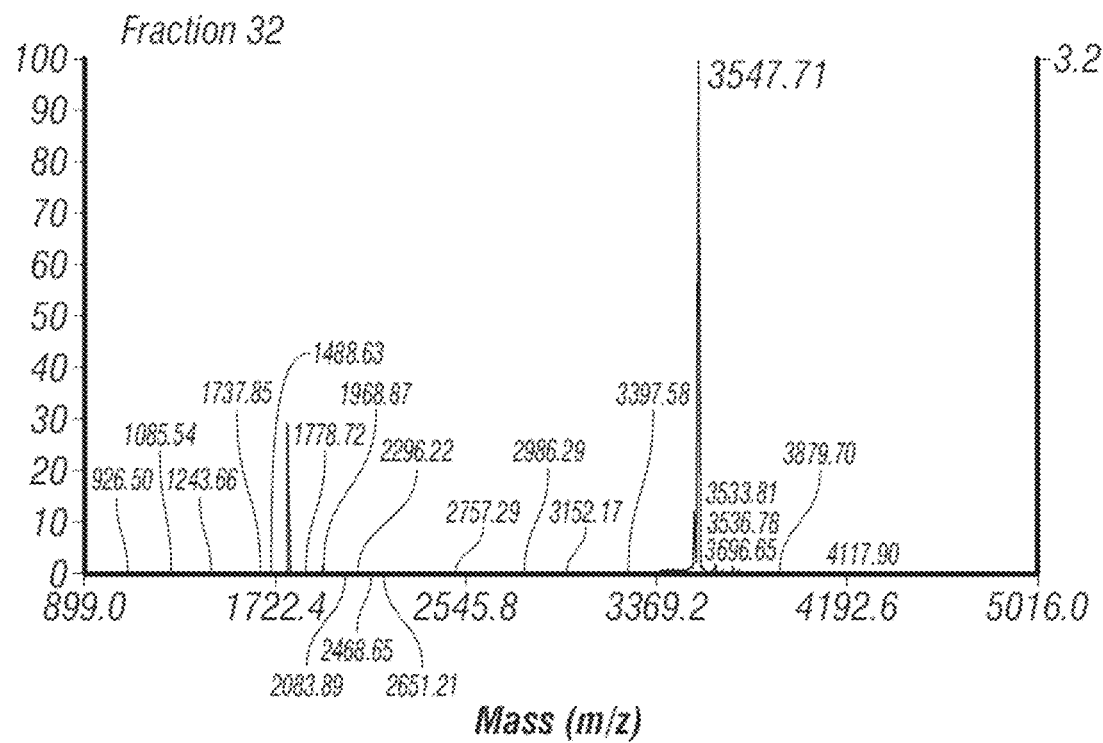

Peptides with antimicrobial activity produced by the microbiome. To determine what was responsible for the antimicrobial activity detected in CoNS strains genetic and biochemical approaches were used. Bacteriocins are a class of AMPs produced by some CoNS species. However, no DNA encoding the known bacteriocins epiA, pepA, eciA and elkA, was detected in non-atopic skin (n=14) by PCR (Table 2, primer sequences). Accordingly, experiments were performed to purify and identify the source of activity from a representative colony of antimicrobial S. hominis isolated from a non-atopic subject. Reverse-phase chromatography revealed two independent peaks (3152.2 and 3547.7 Da) associated with antimicrobial activity (FIG. 7). N-terminal amino acid sequencing of the 3152.2 Da peptide was KCSWWNAA. The full sequence of the 3547.7 Da peptide was obtained by genome-guided MALDI-TOF/TOF analysis (FIG. 8). Alignment of mass and amino acid sequence to the genome sequence of this S. hominis strain revealed that these novel AMPs were encoded within the gene cluster of lanM, lanC and lanT homologs (FIG. 9), and consistent with identities as lantibiotics. As these AMPs were previously unknown, they were named Hogocidin-α (3152.2 Da) and -β (3547.7 Da) from the Japanese "Hogo" meaning "Protect." These newly described AMPs were readily detectable by PCR in 50% of 14 non-atopic individuals. The predicted secondary structures of mature Hogocidin-α and Hogocidin-3 are shown in FIG. 5A. The minimal bactericidal concentration (>99.9% killing) of purified Hogocidin-α and -β against S. aureus was 0.625 μM and 1.25 μM, respectively (FIG. 5B), an activity more potent than conventional AMPs produced on human skin. Importantly, co-incubation of each Hogocidin peptide with the human skin cathelicidin AMP LL-37 showed strong synergistic antimicrobial activity against S. aureus (FIG. 5B), suggesting AMPs derived from microbiome enhance capacity of host innate immune defense to resist S. aureus.

Example 2

FAME analysis of bacterial strains. Because the lipid composition of whole bacterial cells (predominantly the cell membranes), which can be represented by the relative abundance of fatty acid methyl esters present in a saponified and methylated sample of bacterial cell extracts, is very nearly unique to each strain, the identified strains were subjected to Fatty Acid Methyl Ester (FAME) analysis. Bacterial strains were cultured and harvested according to standard techniques. Cells were subjected to saponification and methylation before being extracted into the mobile phase solvent for gas chromatography. Samples were loaded and run according to the instrument manufacturer's instructions. The resulting chromatograms are shown in FIGS. 11 through 19.

Example 3

Figure 20A:
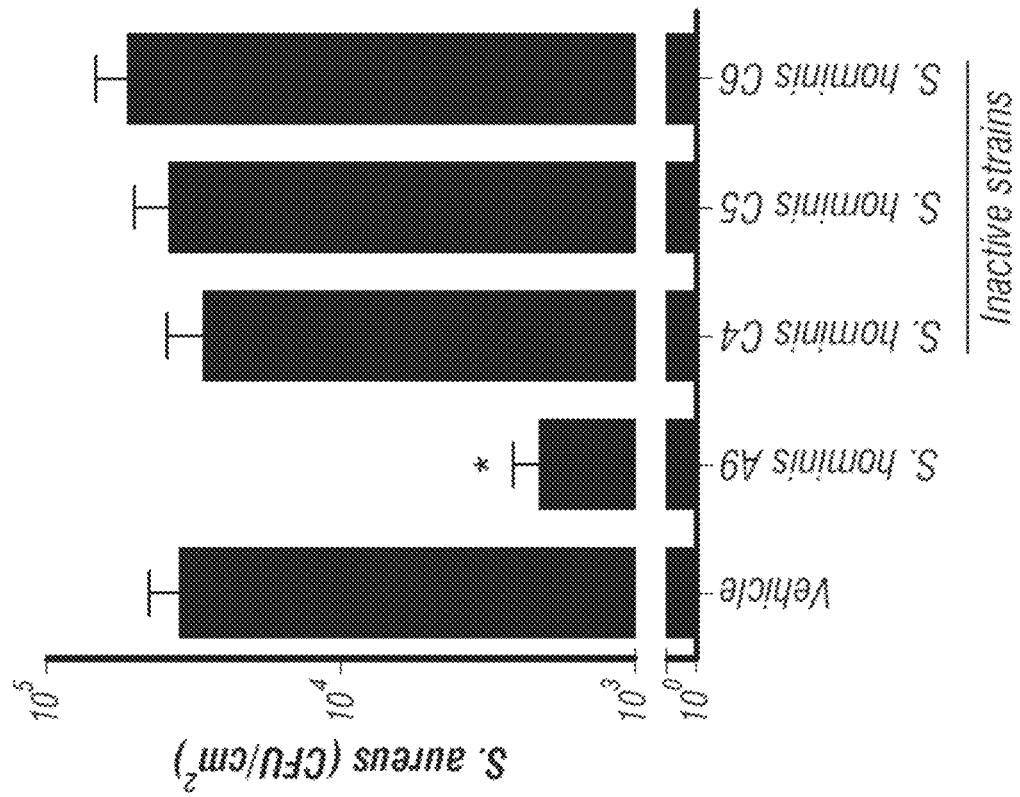
Figure 20B:
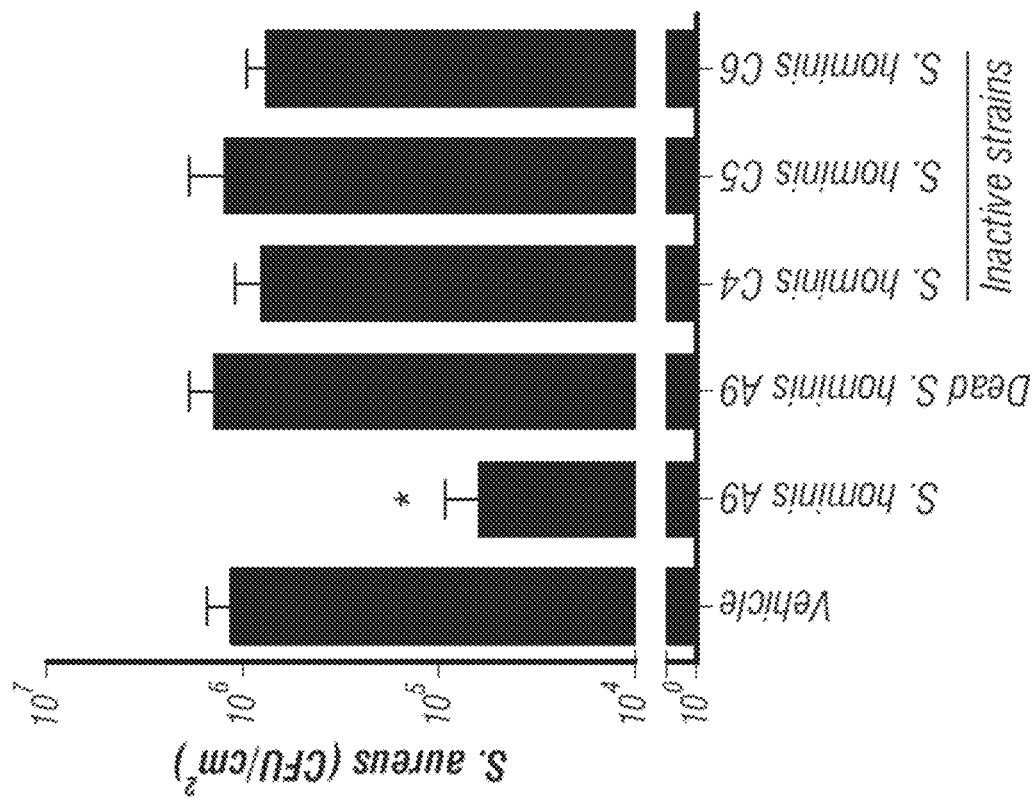

Commensal bacteria protect the skin from colonization by *S. aureus*. Having established an association between AMP-producing commensal CoNS and colonization with *S. aureus*, and having identified active peptides produced by these strains, experiments were performed to test if the presence of these bacteria will reduce colonization by *S. aureus*. Clinical CoNS isolates were applied to the surface of sanitized pigskin on which defined amounts of *S. aureus* had first been applied. A significant decrease in survival of *S. aureus* was seen after a single application of *S. hominis* A9 at a density consistent with estimates of the density of bacteria on normal human skin ($1 \times 10^5$ CFU/cm$^2$) (FIG. 20A) Application of *S. hominis* A9 that was killed and rinsed prior to application, or use of other *S. hominis* strains that did not show antimicrobial activity in culture did not affect *S. aureus* survival. Similarly, a single application of active *S. hominis* to the backs of mice on which defined amounts of *S. aureus* had been applied reduced the survival of *S. aureus* on the skin (FIG. 20B). In contrast, application of inactive strains at the similar density did not inhibit *S. aureus*.

Figure 20E:
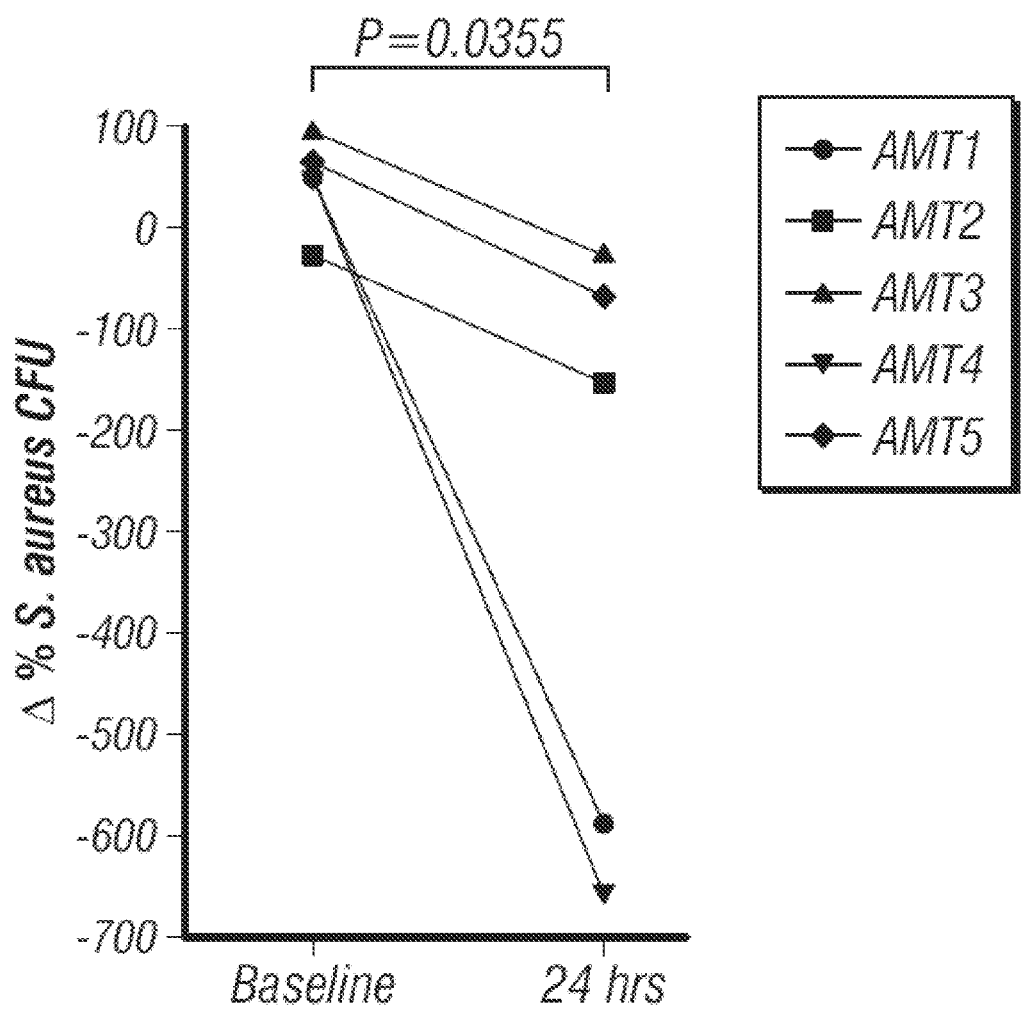
Figure 21A:
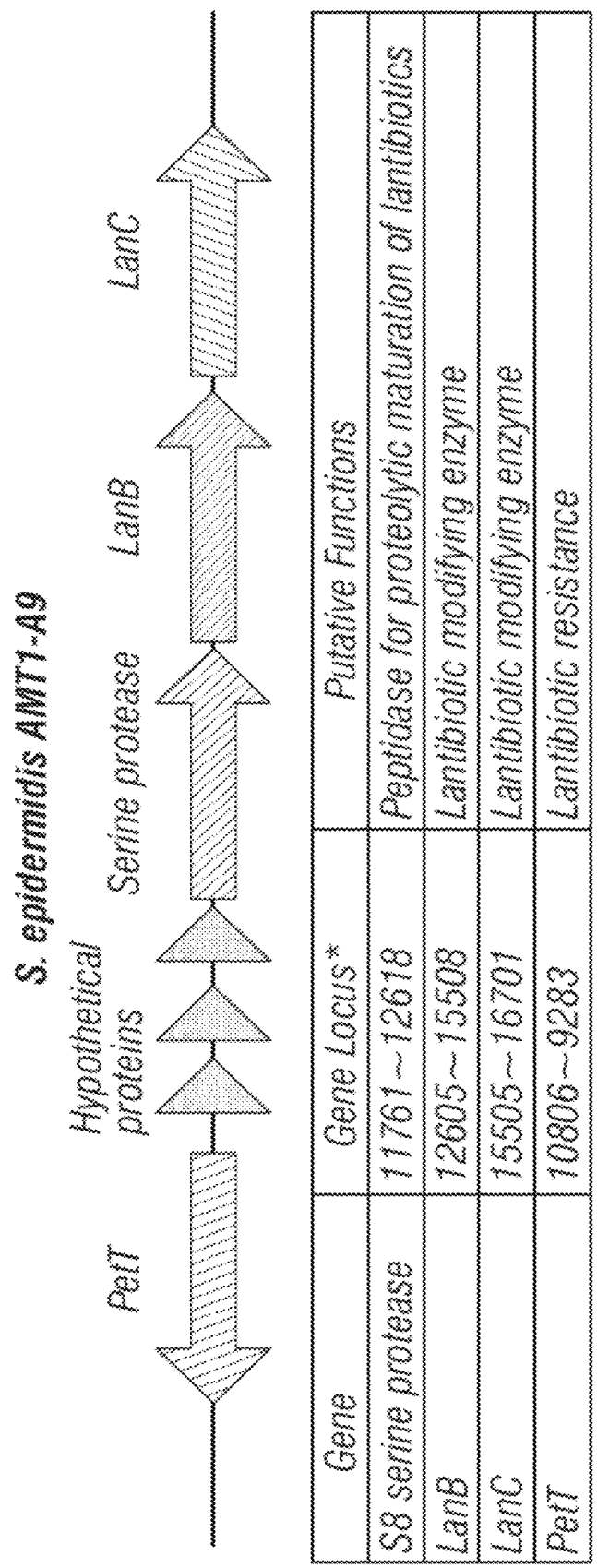
Figure 22A:
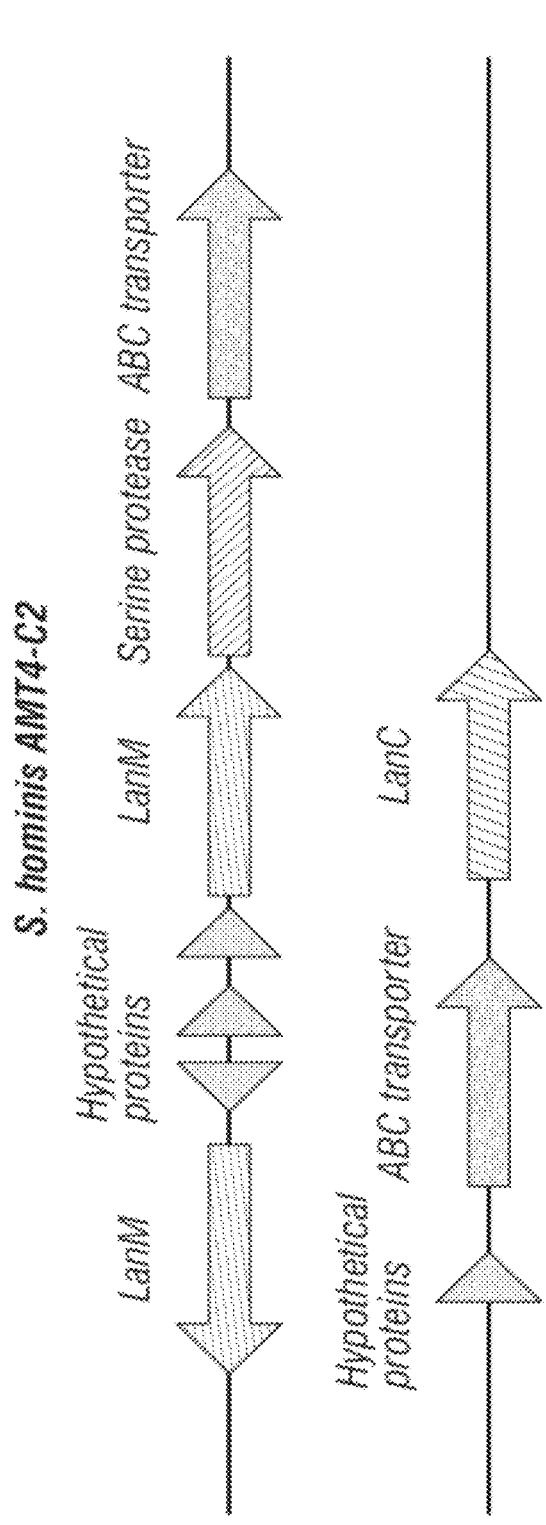
FIG. 22A-B: Hypothetical antimicrobial genes identified in anti-*S. aureus* strains AMT4-C2 (FIG. 22A) and AMT4-G1 (FIG. 22B) used for autologous microbiome transplant. Whole genome sequence of active CoNS clones were obtained by miSeq and analyzed on the RAST Server (rast.nmpdr.org) to identify antimicrobial class.
Figure 22B:
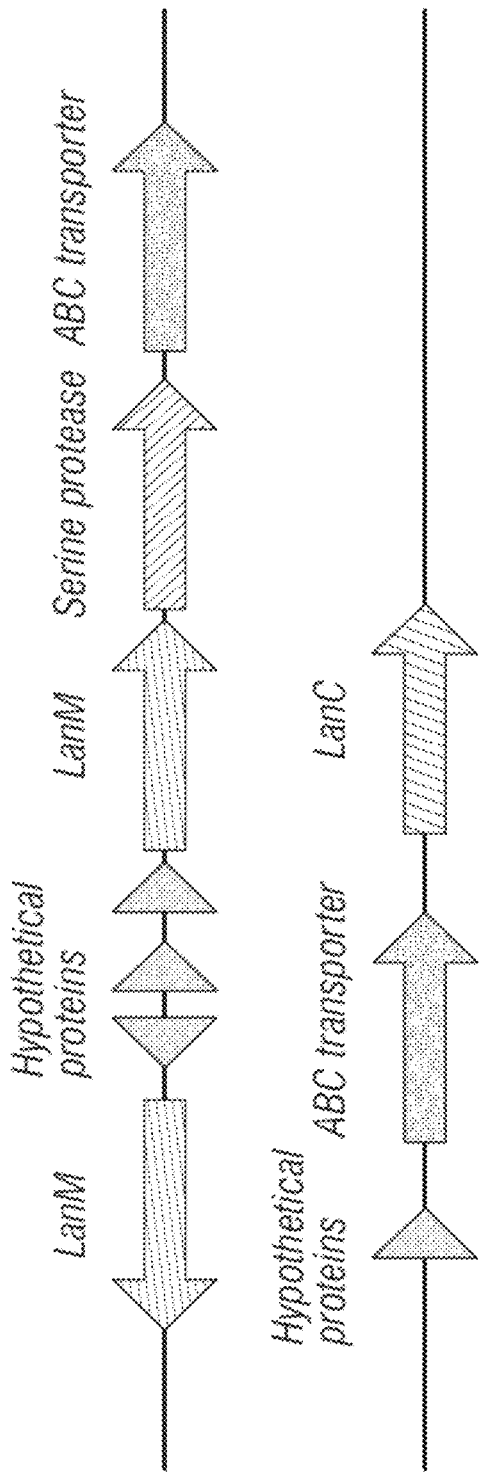
Figure 23A:
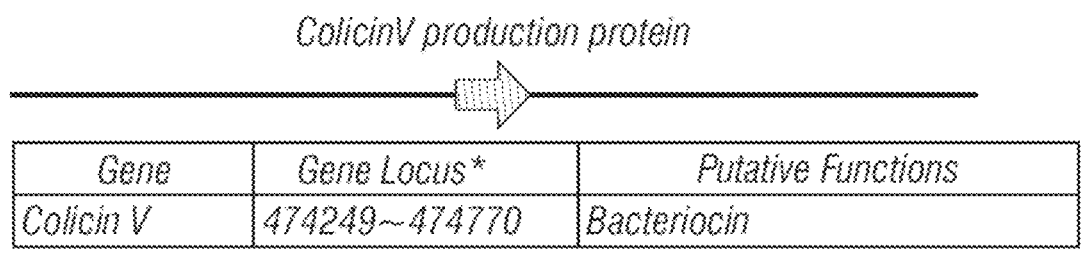
FIG. 23A-C: Hypothetical antimicrobial genes identified in anti-*S. aureus* strains AMT4-D12 (FIG. 23A), AMT5-05 (FIG. 23B), and AMT5-G6 (FIG. 23C) used for autologous microbiome transplant. Whole genome sequence of active CoNS clones were obtained by miSeq and analyzed on the RAST Server (rast.nmpdr.org) to identify antimicrobial class.
Figure 23B:
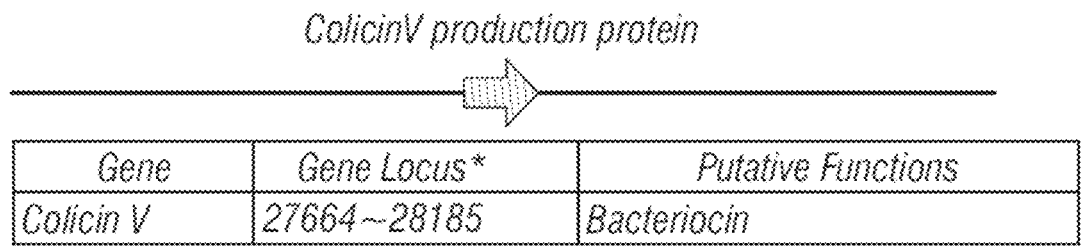
Figure 23C:
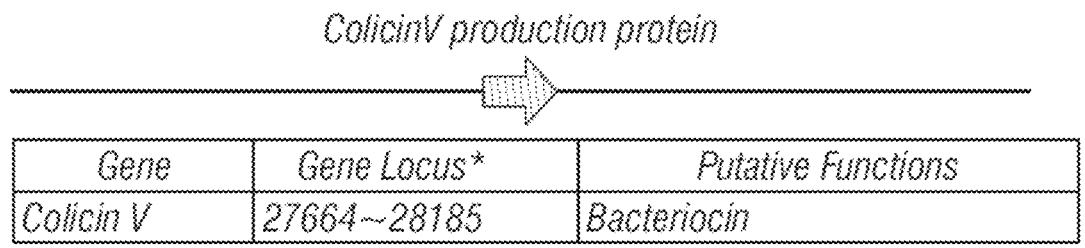
Figure 24:
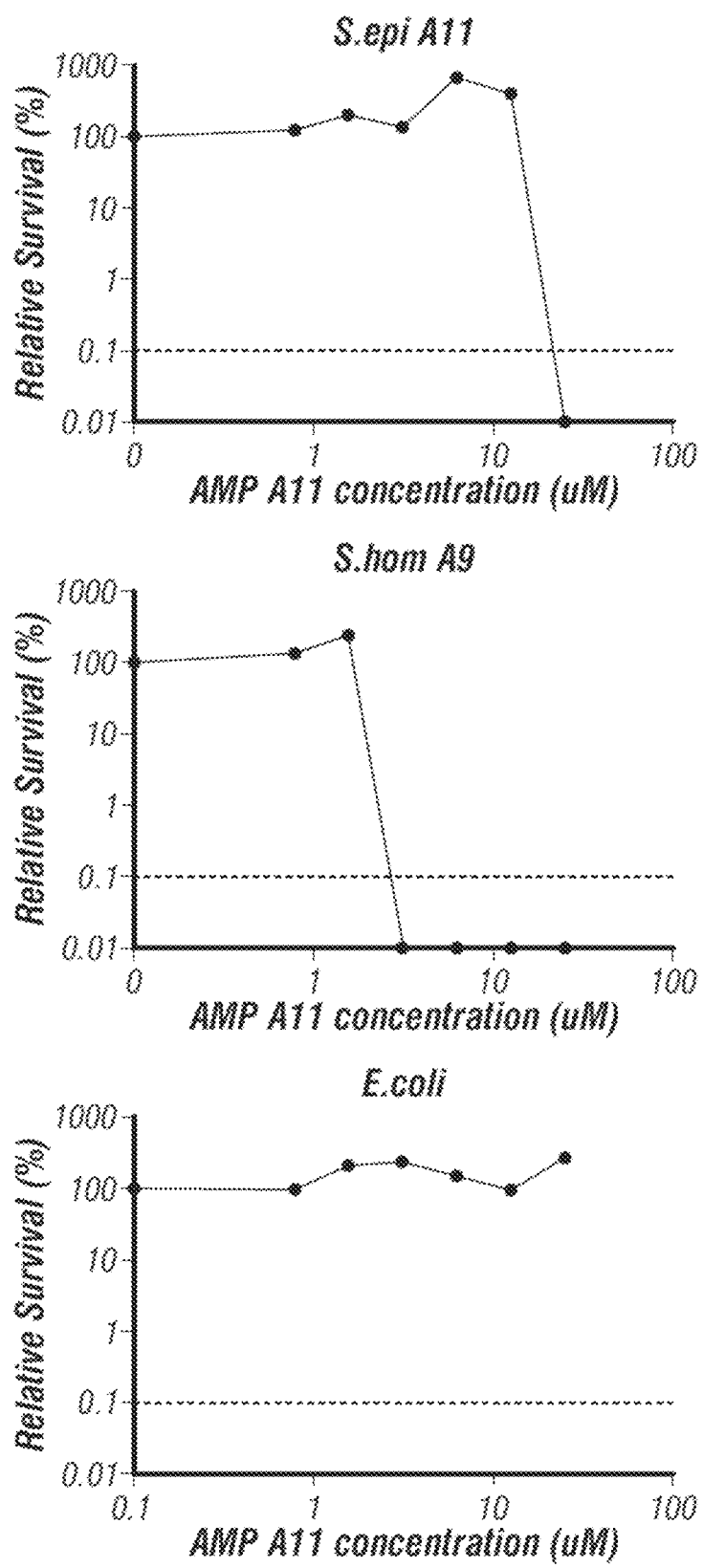
FIG. 24 shows dose-dependent killing curve of antimicrobial peptide purified from culture supernatant of *Staphylococcus epidermidis* A11 strain isolated from normal skin. Indicated bacterial species ($1\times10^5$ CFU/mL) were incubated with various concentrations of purified *Staphylococcus epidermidis* A11 antimicrobial peptide (comprising SEQ ID NO:55) in 50% Muller-Hinton Broth/50% PBS at 37° C. for 24 hrs. *Propionibacterium acnes* were incubated in 100% Reinforced-Clostridial Media under an anaerobic condition. S. epiA11, *Staphylococcus epidermidis* A11 strain; S. epi12228, *Staphylococcus epidermidis* ATCC12228 strain; S. homA9, *Staphylococcus hominis* A9 strain; S. aur113, *Staphylococcus aureus* 113 strain; P.ac, *Propionibacterium acnes* ATCC6919 strain; E. coli, *Escherichia coli* ATCC25922; P. aeruginosa, *Pseudomonas aeruginosa* ATCC14213.
Figure 24:
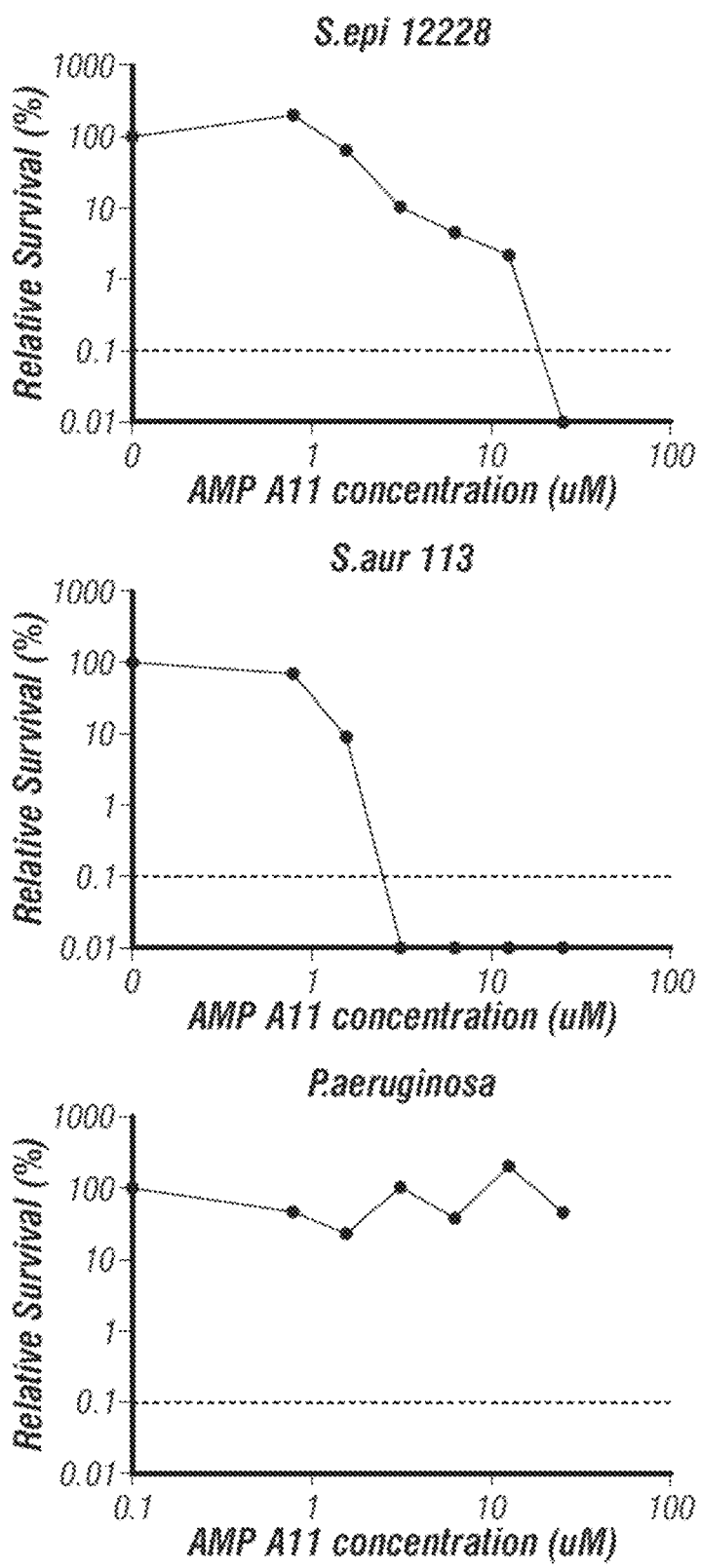
Figure 24:
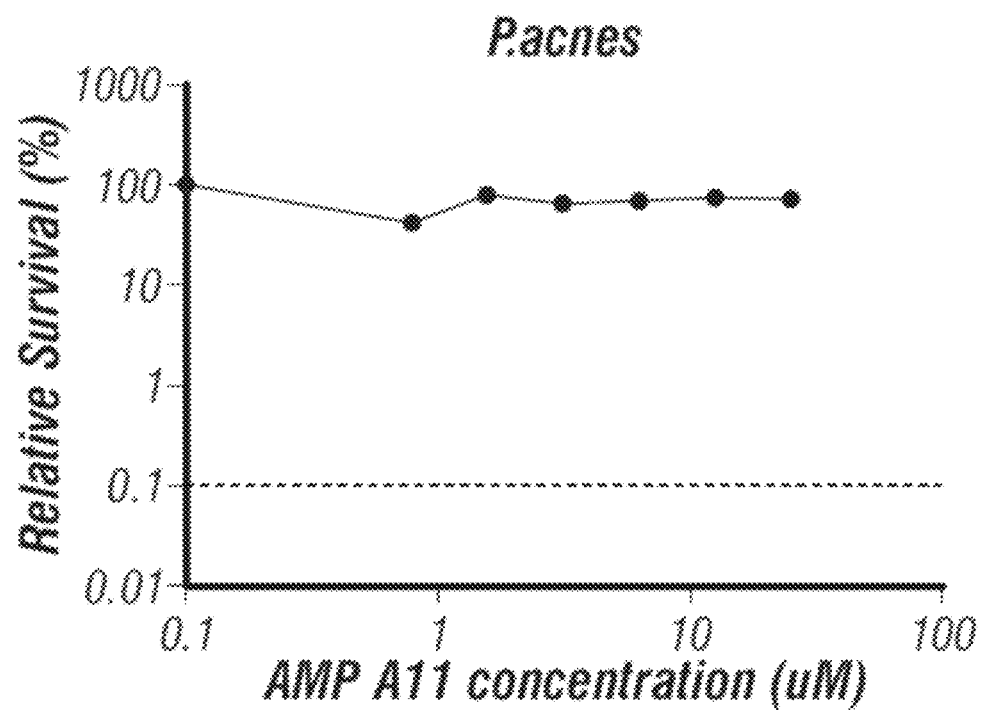

Finally, to directly test the capacity of functionally screened and isolated commensal bacteria to inhibit *S. aureus* in humans, experiments were performed to test the effect of application of these bacteria to the skin of subjects with AD. As previously shown, strains with antimicrobial activity were rare within the total CoNS community of these subjects, but could be identified if sufficient colonies were screened. 5 AD patients who were *S. aureus*-culture positive were recruited to participate in this study. CoNS clones with antimicrobial activity were identified and expanded for planned reapplication to the subject (Autologous Transplant). Each selected clone was sequenced and clusters of lantibiotic-related genes were identified in 5 *S. epidermidis* or *S. hominis* strains, and colicin V genes were seen in 2 *S. epidermidis* strains and in 1 *S. hominis* strain (FIG. 21-23). In a double-blind fashion, vehicle cream alone or bacteria formulated in cream were applied once to the skin of each arm and then *S. aureus* measured 24 hrs later. Selected strains were applied to a total final concentration of $1 \times 10^5$ CFU/cm$^2$, a density similar to previous assessments of the abundance of bacteria on normal human skin. A single application of these functionally defined and autologously derived CoNS strain(s) significantly decreased *S. aureus* CFU within 24 hrs in comparison to baseline (FIG. 20E).

Example 4

Transplantation of antimicrobial CoNS on ex vivo pig skin and mice. Frozen pig skin sheet was obtained from Loretta Tomlin Animal Technologies (Livermore, Calif.) and sanitized by surgical brush with 3% chloroxylenol. The skin sheet was cut into 2.5 cm×2.5 cm and rinsed with sterile PBS more than 20 times to remove chloroxylenol residue. Back skin of C57BL6 female, 6 week-old mice that were randomly selected was shaved, treated with depilatory cream and rinsed with water at least 24 hrs before bacteria application. The shaved skin was cleaned with alcohol swab twice to remove originally colonized bacteria. All experiments involving live animal work were in accordance with the approval of the Institutional Animal Care and Use Guidelines.

*S. aureus* (ATCC35556) ($1 \times 10^5$ CFU/cm$^2$) were epicutaneously challenged on the pig skin (2.5×2.5 cm) or dorsal skin of mice (2×2 cm). *S. hominis* A9 strain isolated from non-AD subject, that produce Sh-lantibiotics (hogocidins), or *S. hominis* strains isolated from lesional skin of AD subject, which did not produce antimicrobial activity in culture, was formulated at $1 \times 10^7$ CFU/g in skin moisturizer which was confirmed not to affect bacteria viability. Either *S. hominis* A9 strain with anti-*S. aureus* activity, UV-killed *S. hominis* A9, inactive strains of *S. hominis* C4, C5 and C6 ($1 \times 10^5$ CFU/10 µL), or vehicle were subsequently applied on the surface of pig skin or mouse dorsal skin for 20 hrs (FIGS. 20A and 20B). Purified lantibiotic (0.5 nmol), conditioned media of *S. hominis* A9 (50 µL) were applied to the surface of sanitized pig skin. Pig skin was incubated at 30° C. in a 6-well plate. Live bacteria were harvested with a Catch-All Swab pre-wetted with TSB from the skin surface as described above. Bacteria were suspended by vortex swab head vigorously in 1 mL TSB. Ten-fold serial dilution of the bacteria suspension was spread on a Baird-Parker agar with egg yolk tellurite for selective count of *S. aureus*. *S. aureus* (a large black colony with halo) were distinguished from *S. hominis* (a small gray colony without halo) on the selective agar plate.

Example 5

Autologous microbiome transplant. The approach of autologous microbiome transplant (AMT) for patients with AD has been officially approved by US Food and Drug Administration (FDA) and this protocol has been filed as an investigational new drug application (IND) (UCSD Approval #15786). At the screening visit, AD patients who are *S. aureus* carriers on the lesional sites of both antecubital fossa were screened. In the meantime, skin bacteria were obtained by swabbing from nonlesional skin of upper arm of AD patient to screen CoNS strain producing antimicrobial activity against *S. aureus*. Species of antimicrobial CoNS isolates were identified by Sanger sequencing of the full-length 16S rRNA gene. Glycerol stocks of CoNS isolates were stored at −80° C. until the second visit when patients received transplant therapy. Each CoNS strain was individually expanded in TSB overnight. Each CoNS strain was formulated at $1 \times 10^7$ CFU/g in skin moisturizer which was confirmed not to affect bacteria viability. Only a single *S. epidermidis* or *S. hominis* strain with antimicrobial activity was isolated from 3 patients. In these cases, a single strain of CoNS was formulated. Three and 2 antimicrobial *S. hominis* or *S. epidermidis* strains were isolated from 2 AD patients (FIG. 20D). In these cases, an equal CFU of each CoNS was formulated at the total concentration of $10^7$ CFU/g. At the second visit, involved area was measured and the baseline CFU of live *S. aureus* on lesional sites of both forearm was quantified as described above. One arm was treated with AMT formulation at 10 mg/cm$^2$ to get $1 \times 10^5$ CFU/cm² of CoNS. The other arm received an equal amount of moisturizer only. All treatment was conducted in double-blinded fashion and unblinded after all results were analyzed. Subjects avoided bathing, showering, exercising or applying any topical products to their arms, and wore a clean and long-sleeved shirt to avoid cross contamination of applied CoNS to the other arm until the next visit. At the third visit, S. aureus CFU in involved area was measured. Difference in S. aureus survival between vehicle and AMT arms was calculated as [AMT ($\chi$ hrs)–Vehicle ($\chi$ hrs)]/AMT (Baseline) to get Δ% S. aureus CFU ($\chi$=0 hr or 24 hrs) (FIG. 20E).

Statistical analysis. For all experiments, at least three or more biological replicates were used, and these are indicated in Figure legends. For all mouse experiments, at least six mice were used per treatment group. Therefore, for the reported differences, the sample size used gave sufficient power for reliability. Paired t-tests (two-tailed) were used to compare lesional to nonlesional samples within AD subjects and independent t-tests (two-tailed) were used to compare non-AD to AD samples. For non-normally distributed variables such as CoNS with Sh-antibiotic-α (%), non-parametric approaches such as Wilcoxon-Mann-Whitney tests for non-AD to AD samples and Wilcoxon signed rank tests for lesional to nonlesional samples within AD subjects were used. Longitudinal mixed models of frequency of antimicrobial CoNS and the ratio of live *Staphylococcus* to *Staphylococcus* DNA over time were also fit. Each model included lesion type, visit, and their interaction term as fixed effects, while a compound symmetry structure was used to account for correlation between samples obtained from the same subject at multiple time points. Frequency of antimicrobial CoNS used a cumulative log it link and multinomial distribution of categorized percentages (<=20, 21-79, >=80) to account for a bi-modal distribution. Statistical analyses were performed using SAS (version 9.3) software and R software (version 3.1.1).

Example 6

Allogeneic Transplant. $10^5$ CFU/g of strains SH-A9, SH-C2, SE-A11, AMT1, AMT2, AMT3, AMT4-C2, AMT4-G1, AMT4-D12, AMT5-C5, AMT5-G6 and/or SE-MO34, are formulated in skin moisturizer which is confirmed not to affect bacteria viability. Subjects for treatment are identified based on the existence of Atopic Dermatitis and/or active S. aureus infection. Subjects are instructed to avoid bathing, showering, exercising or applying any topical products to the affected area for three days. Compliant patients show significant reductions in S. aureus levels in the treated area after 7 days (>/=3 log reduction in recoverable S. aureus colony counts). Compliant patients show clinically observable reductions in symptoms of S. aureus infection and/or atopic dermatitis continuing for at least 14 days after the initial treatment.

Example 6

Purification of AMPS produced by S. epidermidis. Sterile conditioned media from a representative antimicrobial S. epidermidis A11 strain was used to further identify molecules with antimicrobial activity on normal skin that were in low abundance on atopics. Activity was precipitated by ammonium sulfate (70% saturation), dissolved in $H_2O$ and applied on a Sep-Pak cartridge (Waters Co). Active fractions were eluted with 40% acetonitrile in $H_2O$ and subjected to HiTrap® SP (GE Healthcare Life Sciences) separation and activity eluted at 500 mM NaCl. Third step HPLC purification was done with CapCel Pak C8 (5 μm, 300 Å, 4.6×250 mm) (Shiseido Co.) with a linear gradient of acetonitrile from 5% to 50% in 0.1% (v/v) TFA at 0.8 mL/min.

Identification of AMPs produced by S. epidermidis. Antimicrobial activity was purified from sterile conditioned media of a representative antimicrobial S. epidermidis A11 strain isolated from a non-atopic subject. The characteristics of the purified active molecule was determined by MALDI-TOF/TOF and Edman terminal sequencing.

Mass Spectrometry. Mass spectra of HPLC-purified AMPs from S. epidermidis A11 were recorded using a MALDI-TOF/TOF Bruker Autoflex™ Speed instrument (Bruker Daltonics) controlled by the flexcontrol software (Bruker Daltonics). Mass spectrometric analyses were performed in positive ion reflectron mode using cyano-4-hydroxycinnamic acid as a matrix (CHCA) 10 mg/mL (Sigma-Aldrich) dissolved in 50% acetonitrile (ACN) and 0.1% trifluoroacetic acid (TFA). Full scan mass spectra were acquired in positive ion reflectron mode for mass range 1000-6000 m/z. Each mass spectrum is the result of 750 averaged laser shots with the laser intensity set around 65% of full laser intensity and a detector gain enhanced at 8×4 GS/s (as selected within the Bruker Flex Control software). Resulting mass spectra were analyzed using flex analysis software (Bruker Daltonics). Spectra were calibrated to PepMix internal standard solutions.

Figure 25A:
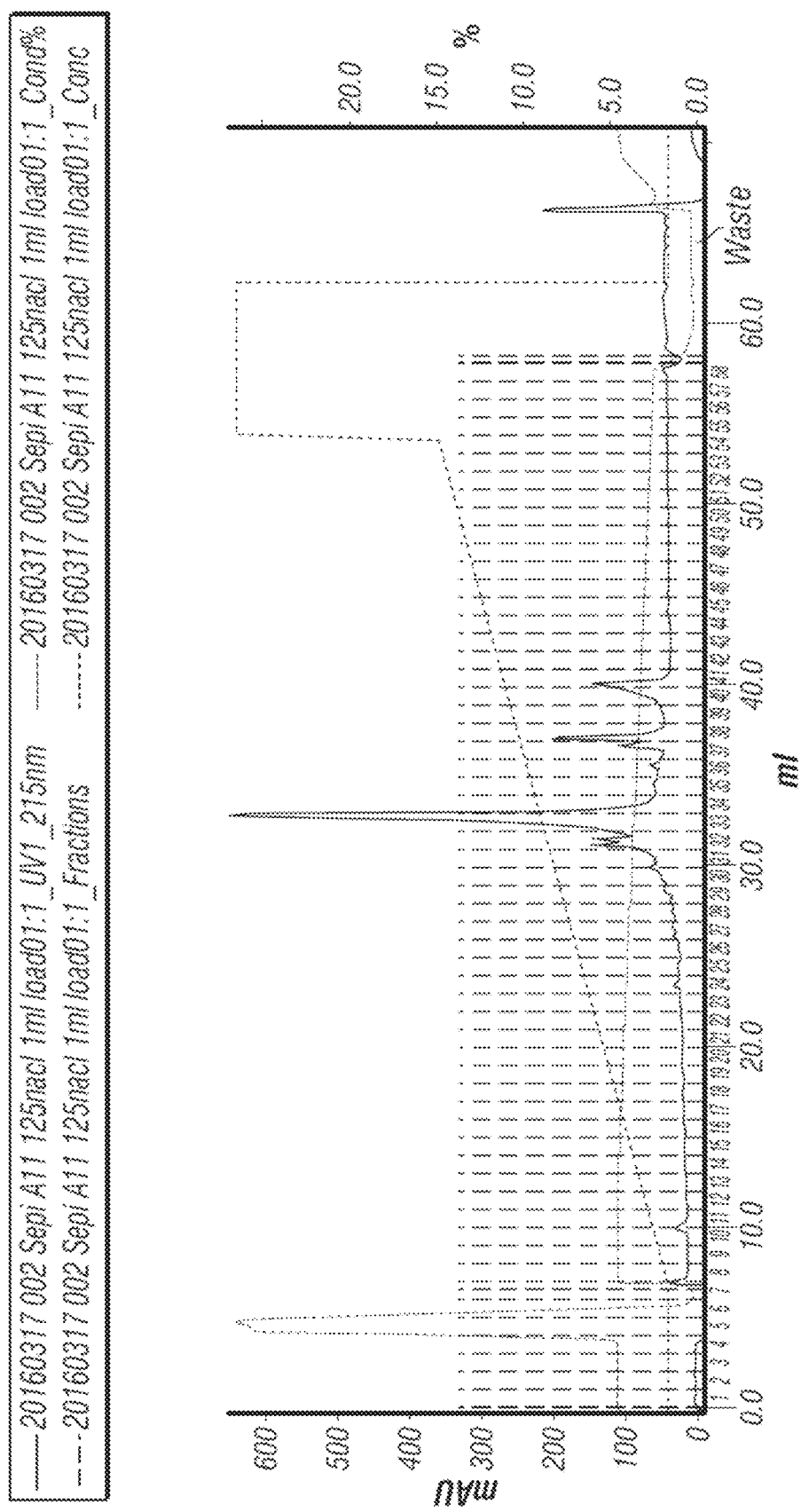
FIG. 25A-B shows data related to an antimicrobial peptide purified from culture supernatant of a clinical isolate strain of *Staphylococcus epidermidis* (A11 strain) by HPLC (A). Active fraction (Fraction 33-34) was analyzed by MALDO-TOF mass to estimate molecular weight of active antimicrobial peptide (B). Observed molecular weight was 3484.90 (m/z). N-terminal sequencing of the peptide is provided in SEQ ID NO:55.
Figure 25B:
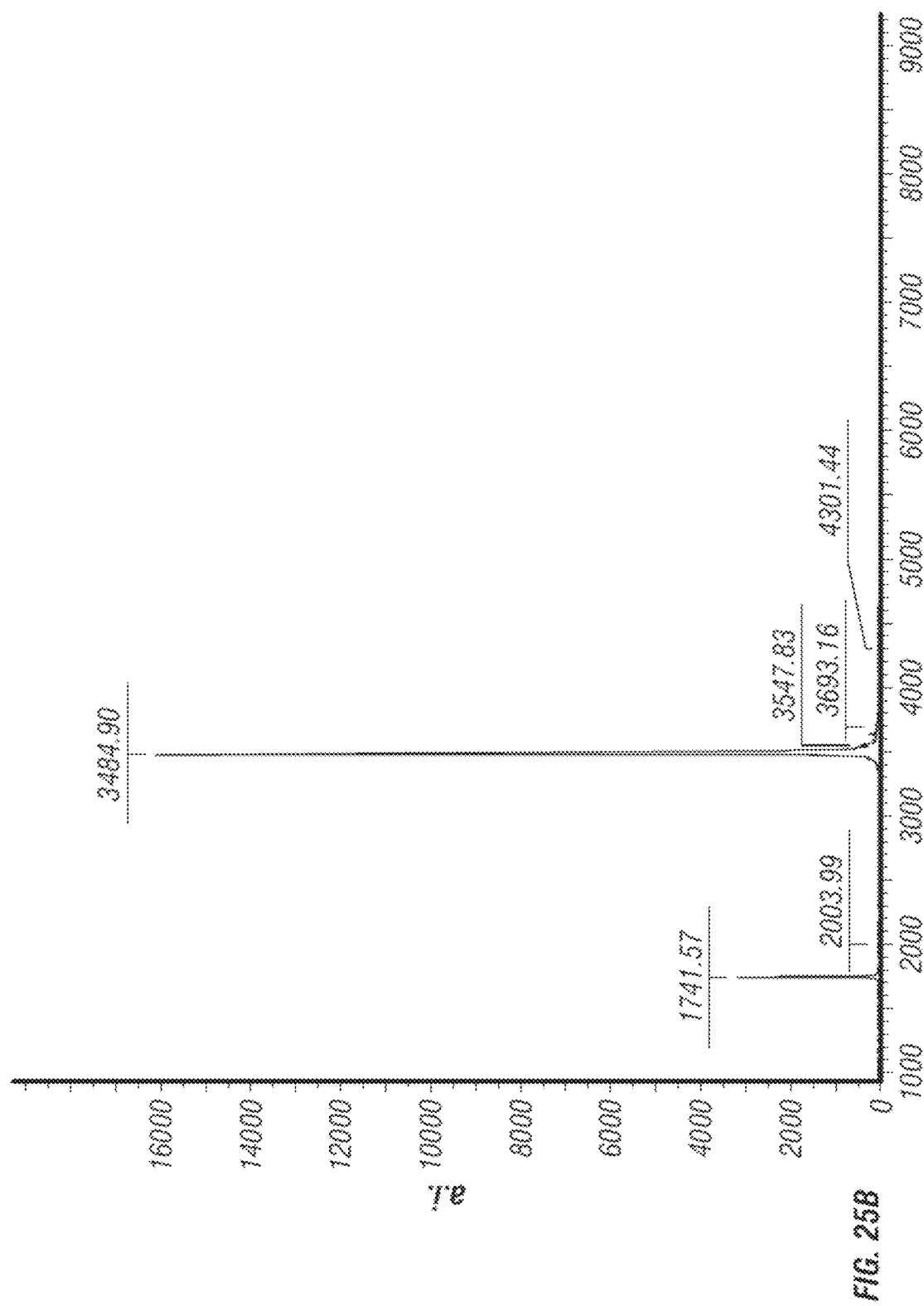

N-terminal Protein Sequencing. The N-terminal amino acid sequence of purified (Fractions 33-34, FIG. 25A) was analyzed by 15 cycles of Edman degradation on Procise® 494HT Protein Sequence system (Applied Biosystems). The N-terminal sequence is provided in SEQ ID NO:55.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a skin disease or disorder, comprising:
    contacting a subject having a skin disease or disorder with an effective amount of a composition comprising:
    a peptide comprising the sequence of KCSWWNASCHLGNNGKICTVSHECAAGCNL (SEQ ID NO: 56) or ATPTITTSSATCGGIIVAASAAQCPTLACSSRCGKRKK (SEQ ID NO: 57); and
    one or more pharmaceutical excipients.

2. The method of claim 1, wherein the composition comprises one or more probiotic bacteria capable of producing the peptide.

3. The method of claim 2, wherein the one or more probiotic bacteria comprises one or more coagulase-negative bacterial strains of the genus *Staphylococcus*.

4. The method of claim 1, wherein the skin disease or disorder is a skin infection, a skin colonization, a mucosal infection, a mucosal colonization, or any combination thereof.

5. The method of claim 1, wherein the skin disease or disorder is folliculitis, atopic dermatitis, psoriasis, mastitis, acne, or any combination thereof.

6. The method of claim 1, wherein the composition comprises a prebiotic compound, a protectant, humectant, emollient, abrasive, salt, a surfactant, or any combination thereof.

7. The method of claim 1, wherein the composition is a topical formulation.

8. The method of claim 1, wherein the skin disease or disorder comprises *Staphylococcus aureus* infection.

9. The method of claim 1, wherein the peptide is post-translationally modified.

10. The method of claim 2, wherein the one or more probiotic bacteria strains are provided in a live form.

11. The method of claim 2, wherein the one or more probiotic bacteria strains are provided in a lyophilized form, a freeze-dried form, a spray dried form, or a mixture thereof.

12. The method of claim 11, wherein the one or more probiotic bacteria strains can be reconstituted into a live form.

13. The method of claim 2, wherein the one or more probiotic bacteria strains are present in said composition at a concentration of at least $10^3$ CFU/gram.

14. The method of claim 1, wherein the composition further comprises a cathelicidin peptide.

15. The method of claim 1, wherein the peptide comprises one or more D-amino acids.

16. The method of claim 1, wherein the peptide comprises one or more non-naturally occurring amino acids.

17. The method of claim 1, wherein the subject is a mammal.

18. The method of claim 17, wherein the subject is a human.

19. The method of claim 1, wherein the composition is applied topically.

20. The method of claim 1, wherein the composition is the form of a cream, ointment, unguent, spray, powder, oil, thickened formulation or poultice.

* * * * *

SEQUENCE LISTING

```
<160> NUMBER OF SEQ ID NOS: 57

<210> SEQ ID NO 1
<211> LENGTH: 186
<212> TYPE: DNA
<213> ORGANISM: Staphylococcus hominis
<220> FEATURE:
<221> NAME/KEY: CDS
<222> LOCATION: (1)..(186)

<400> SEQUENCE: 1
```

```
atg agt aaa tta gaa cta ctt aat gaa tct aaa gca aat tat ctt gaa    48
Met Ser Lys Leu Glu Leu Leu Asn Glu Ser Lys Ala Asn Tyr Leu Glu
1               5                   10                  15 aaa ctt act gat gaa aaa att gaa gaa acg gaa gca tac ggc ggt aaa    96
Lys Leu Thr Asp Glu Lys Ile Glu Glu Thr Glu Ala Tyr Gly Gly Lys
            20                  25                  30 tgt tct tgg tgg aat gca tca tgt cat tta gga aat aat ggg aaa att   144
Cys Ser Trp Trp Asn Ala Ser Cys His Leu Gly Asn Asn Gly Lys Ile
        35                  40                  45 tgt aca gtt tct cat gag tgt gca gca gga tgt aat tta taa           186
Cys Thr Val Ser His Glu Cys Ala Ala Gly Cys Asn Leu
50                  55                  60
```

<210> SEQ ID NO 2
<211> LENGTH: 61
<212> TYPE: PRT
<213> ORGANISM: Staphylococcus hominis

<400> SEQUENCE: 2

Met Ser Lys Leu Glu Leu Leu Asn Glu Ser Lys Ala Asn Tyr Leu Glu
1               5                   10                  15

Lys Leu Thr Asp Glu Lys Ile Glu Glu Thr Glu Ala Tyr Gly Gly Lys
            20                  25                  30

Cys Ser Trp Trp Asn Ala Ser Cys His Leu Gly Asn Asn Gly Lys Ile
        35                  40                  45

Cys Thr Val Ser His Glu Cys Ala Ala Gly Cys Asn Leu
50                  55                  60

<210> SEQ ID NO 3
<211> LENGTH: 201
<212> TYPE: DNA
<213> ORGANISM: Staphylococcus hominis
<220> FEATURE:
<221> NAME/KEY: CDS
<222> LOCATION: (1)..(201)

<400> SEQUENCE: 3

```
atg ttt agt aaa aat ttc caa aga aat gaa aag atg gaa aat act ttg    48
Met Phe Ser Lys Asn Phe Gln Arg Asn Glu Lys Met Glu Asn Thr Leu
1               5                   10                  15 aaa aag gta agt tca gct aat gat gtg aat gga gga gct aca ccg act    96
Lys Lys Val Ser Ser Ala Asn Asp Val Asn Gly Gly Ala Thr Pro Thr
            20                  25                  30 att act aca tct tca gca act tgt ggt ggt att att gtt gcg gca agt   144
Ile Thr Thr Ser Ser Ala Thr Cys Gly Gly Ile Ile Val Ala Ala Ser
        35                  40                  45 gct gct cag tgt ccg aca tta gct tgc tct tct aga tgt gga aaa aga   192
Ala Ala Gln Cys Pro Thr Leu Ala Cys Ser Ser Arg Cys Gly Lys Arg
50                  55                  60 aaa aaa taa                                                       201
Lys Lys
65
```

<210> SEQ ID NO 4
<211> LENGTH: 66
<212> TYPE: PRT
<213> ORGANISM: Staphylococcus hominis

<400> SEQUENCE: 4

Met Phe Ser Lys Asn Phe Gln Arg Asn Glu Lys Met Glu Asn Thr Leu
1               5                   10                  15

Lys Lys Val Ser Ser Ala Asn Asp Val Asn Gly Gly Ala Thr Pro Thr

```
              20                  25                  30
Ile Thr Thr Ser Ser Ala Thr Cys Gly Gly Ile Ile Val Ala Ala Ser
              35                  40                  45

Ala Ala Gln Cys Pro Thr Leu Ala Cys Ser Arg Cys Gly Lys Arg
          50                  55                  60

Lys Lys
65

<210> SEQ ID NO 5
<211> LENGTH: 170
<212> TYPE: PRT
<213> ORGANISM: Homo sapiens

<400> SEQUENCE: 5

Met Lys Thr Gln Arg Asn Gly His Ser Leu Gly Arg Trp Ser Leu Val
1               5                  10                  15

Leu Leu Leu Leu Gly Leu Val Met Pro Leu Ala Ile Ile Ala Gln Val
              20                  25                  30

Leu Ser Tyr Lys Glu Ala Val Leu Arg Ala Ile Asp Gly Ile Asn Gln
              35                  40                  45

Arg Ser Ser Asp Ala Asn Leu Tyr Arg Leu Leu Asp Leu Asp Pro Arg
          50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
              85                  90                  95

Cys Asp Phe Lys Lys Asp Gly Leu Val Lys Arg Cys Met Gly Thr Val
             100                 105                 110

Thr Leu Asn Gln Ala Arg Gly Ser Phe Asp Ile Ser Cys Asp Lys Asp
             115                 120                 125

Asn Lys Arg Phe Ala Leu Leu Gly Asp Phe Phe Arg Lys Ser Lys Glu
         130                 135                 140

Lys Ile Gly Lys Glu Phe Lys Arg Ile Val Gln Arg Ile Asp Asp Phe
145                 150                 155                 160

Leu Arg Asn Leu Val Pro Arg Thr Glu Ser
                165                 170

<210> SEQ ID NO 6
<211> LENGTH: 5
<212> TYPE: PRT
<213> ORGANISM: Artificial Sequence
<220> FEATURE:
<223> OTHER INFORMATION: Synthetic linker

<400> SEQUENCE: 6

Gly Gly Gly Gly Ser
1               5

<210> SEQ ID NO 7
<211> LENGTH: 22
<212> TYPE: PRT
<213> ORGANISM: Artificial Sequence
<220> FEATURE:
<223> OTHER INFORMATION: Synthetic linker

<400> SEQUENCE: 7

Gly Gly Gly Gly Gly Gly Ser Met Phe Gly Gly Ala Lys Lys Arg Ser
1               5                  10                  15

Gly Gly Gly Gly Gly Gly
```

<210> SEQ ID NO 8
<211> LENGTH: 20
<212> TYPE: DNA
<213> ORGANISM: Artificial Sequence
<220> FEATURE:
<223> OTHER INFORMATION: Staphylococcus aureus-specific PCR primer

<400> SEQUENCE: 8
aactgttggc cactatgagt                                         20

<210> SEQ ID NO 9
<211> LENGTH: 21
<212> TYPE: DNA
<213> ORGANISM: Artificial Sequence
<220> FEATURE:
<223> OTHER INFORMATION: Staphylococcus aureus-specific PCR primer

<400> SEQUENCE: 9
ccagcattac ctgtaatctc g                                       21

<210> SEQ ID NO 10
<211> LENGTH: 20
<212> TYPE: DNA
<213> ORGANISM: Artificial Sequence
<220> FEATURE:
<223> OTHER INFORMATION: Staphylococcus epidermidis-specific PCR primer

<400> SEQUENCE: 10
tcagcagttg aaggacagat                                         20

<210> SEQ ID NO 11
<211> LENGTH: 22
<212> TYPE: DNA
<213> ORGANISM: Artificial Sequence
<220> FEATURE:
<223> OTHER INFORMATION: Staphylococcus epidermidis-specific PCR primer

<400> SEQUENCE: 11
ccagaacaat gaatggttaa gg                                      22

<210> SEQ ID NO 12
<211> LENGTH: 30
<212> TYPE: DNA
<213> ORGANISM: Artificial Sequence
<220> FEATURE:
<223> OTHER INFORMATION: Staphylococcus-genus specific 16S sequence PCR
      primer

<400> SEQUENCE: 12
tttgggctac acacgtgcta caatggacaa                              30

<210> SEQ ID NO 13
<211> LENGTH: 24
<212> TYPE: DNA
<213> ORGANISM: Artificial Sequence
<220> FEATURE:
<223> OTHER INFORMATION: Staphylococcus-genus specific 16S sequence PCR
      primer

<400> SEQUENCE: 13
aacaacttta tgggatttgc wtga                                    24

<210> SEQ ID NO 14
<211> LENGTH: 21

```
<212> TYPE: DNA
<213> ORGANISM: Artificial Sequence
<220> FEATURE:
<223> OTHER INFORMATION: Universal sequence of bacterial 16S rRNA PCR
      primer

<400> SEQUENCE: 14
agagtttgga tcmtggctca g                                              21

<210> SEQ ID NO 15
<211> LENGTH: 17
<212> TYPE: DNA
<213> ORGANISM: Artificial Sequence
<220> FEATURE:
<223> OTHER INFORMATION: Universal sequence of bacterial 16S rRNA PCR
      primer

<400> SEQUENCE: 15
aaggaggtgw tccarcc                                                   17

<210> SEQ ID NO 16
<211> LENGTH: 21
<212> TYPE: DNA
<213> ORGANISM: Artificial Sequence
<220> FEATURE:
<223> OTHER INFORMATION: Staphylococcus epidermidis epidermn PCR primer

<400> SEQUENCE: 16
gattcaggag ctgaaccaag a                                              21

<210> SEQ ID NO 17
<211> LENGTH: 20
<212> TYPE: DNA
<213> ORGANISM: Artificial Sequence
<220> FEATURE:
<223> OTHER INFORMATION: Staphylococcus epidermidis epidermn PCR primer

<400> SEQUENCE: 17
ttgaagccct gccaatctaa                                                20

<210> SEQ ID NO 18
<211> LENGTH: 24
<212> TYPE: DNA
<213> ORGANISM: Artificial Sequence
<220> FEATURE:
<223> OTHER INFORMATION: Staphylococcus epidermidis pep5 PCR primer

<400> SEQUENCE: 18
ctgatgaact tgaacctcaa actg                                           24

<210> SEQ ID NO 19
<211> LENGTH: 23
<212> TYPE: DNA
<213> ORGANISM: Artificial Sequence
<220> FEATURE:
<223> OTHER INFORMATION: Staphylococcus epidermidis pep5 PCR primer

<400> SEQUENCE: 19
gacactgtaa ataaacgcgt agc                                            23

<210> SEQ ID NO 20
<211> LENGTH: 24
<212> TYPE: DNA
<213> ORGANISM: Artificial Sequence
<220> FEATURE:
<223> OTHER INFORMATION: Staphylococcus epidermidis epicidin280 PCR
      primer
```

```
<400> SEQUENCE: 20
gcaactagac aggtatgtcc taaa                                            24

<210> SEQ ID NO 21
<211> LENGTH: 25
<212> TYPE: DNA
<213> ORGANISM: Artificial Sequence
<220> FEATURE:
<223> OTHER INFORMATION: Staphylococcus epidermidis epicidin280 PCR
      primer

<400> SEQUENCE: 21
catctaagat taaatgaggg tggtt                                           25

<210> SEQ ID NO 22
<211> LENGTH: 21
<212> TYPE: DNA
<213> ORGANISM: Artificial Sequence
<220> FEATURE:
<223> OTHER INFORMATION: Staphylococcus epidermidis epilancin K7 PCR
      primer

<400> SEQUENCE: 22
taagtccgca atctgctagt g                                               21

<210> SEQ ID NO 23
<211> LENGTH: 22
<212> TYPE: DNA
<213> ORGANISM: Artificial Sequence
<220> FEATURE:
<223> OTHER INFORMATION: Staphylococcus epidermidis epilancin K7 PCR
      primer

<400> SEQUENCE: 23
cagtaatatt gcaaccgcat gt                                              22

<210> SEQ ID NO 24
<211> LENGTH: 25
<212> TYPE: DNA
<213> ORGANISM: Artificial Sequence
<220> FEATURE:
<223> OTHER INFORMATION: Staphylococcus hominis Hogocidin-alpha PCR
      primer

<400> SEQUENCE: 24
atgagtaaat tagaactact taatg                                           25

<210> SEQ ID NO 25
<211> LENGTH: 25
<212> TYPE: DNA
<213> ORGANISM: Artificial Sequence
<220> FEATURE:
<223> OTHER INFORMATION: Staphylococcus hominis Hogocidin-alpha PCR
      primer

<400> SEQUENCE: 25
ttataaatta catcctgctg cacac                                           25

<210> SEQ ID NO 26
<211> LENGTH: 8
<212> TYPE: PRT
<213> ORGANISM: Staphylococcus hominis

<400> SEQUENCE: 26

Lys Cys Ser Asp Asp Asn Ala Ala
```

```
<210> SEQ ID NO 27
<211> LENGTH: 138
<212> TYPE: DNA
<213> ORGANISM: Staphylococcus hominis
<220> FEATURE:
<221> NAME/KEY: CDS
<222> LOCATION: (1)..(138)

<400> SEQUENCE: 27 atg gat att ata aaa gta aat aaa aca gaa aga atg aat gat aat aga      48
Met Asp Ile Ile Lys Val Asn Lys Thr Glu Arg Met Asn Asp Asn Arg
1               5                   10                  15 aaa att gta atg att ttt tct tta tac gat aca ttt ttt aac gct act      96
Lys Ile Val Met Ile Phe Ser Leu Tyr Asp Thr Phe Phe Asn Ala Thr
                20                  25                  30 aat aca cat aag cta aag agt atg aag ctt aat gcg aaa taa             138
Asn Thr His Lys Leu Lys Ser Met Lys Leu Asn Ala Lys
            35                  40                  45

<210> SEQ ID NO 28
<211> LENGTH: 45
<212> TYPE: PRT
<213> ORGANISM: Staphylococcus hominis

<400> SEQUENCE: 28

Met Asp Ile Ile Lys Val Asn Lys Thr Glu Arg Met Asn Asp Asn Arg
1               5                   10                  15

Lys Ile Val Met Ile Phe Ser Leu Tyr Asp Thr Phe Phe Asn Ala Thr
                20                  25                  30

Asn Thr His Lys Leu Lys Ser Met Lys Leu Asn Ala Lys
            35                  40                  45

<210> SEQ ID NO 29
<211> LENGTH: 168
<212> TYPE: DNA
<213> ORGANISM: Staphylococcus epidermidis
<220> FEATURE:
<221> NAME/KEY: CDS
<222> LOCATION: (1)..(168)

<400> SEQUENCE: 29 atg gta tgg atc cat ggt ggt ggt aac tta ggt ggt gct ggc tta gaa      48
Met Val Trp Ile His Gly Gly Gly Asn Leu Gly Gly Ala Gly Leu Glu
1               5                   10                  15 gat gct ttt gat ggt aat act tta gct aaa cat aca tca aaa att aaa      96
Asp Ala Phe Asp Gly Asn Thr Leu Ala Lys His Thr Ser Lys Ile Lys
                20                  25                  30 tat gtt ttt gga aat ttg caa cct gaa aac cat tat gat gat att gat     144
Tyr Val Phe Gly Asn Leu Gln Pro Glu Asn His Tyr Asp Asp Ile Asp
            35                  40                  45 ata ata atc tca aaa caa tta taa                                      168
Ile Ile Ile Ser Lys Gln Leu
        50                  55

<210> SEQ ID NO 30
<211> LENGTH: 55
<212> TYPE: PRT
<213> ORGANISM: Staphylococcus epidermidis

<400> SEQUENCE: 30

Met Val Trp Ile His Gly Gly Gly Asn Leu Gly Gly Ala Gly Leu Glu
1               5                   10                  15
```

```
Asp Ala Phe Asp Gly Asn Thr Leu Ala Lys His Thr Ser Lys Ile Lys
         20                  25                  30

Tyr Val Phe Gly Asn Leu Gln Pro Glu Asn His Tyr Asp Asp Ile Asp
         35                  40                  45

Ile Ile Ile Ser Lys Gln Leu
 50                  55

<210> SEQ ID NO 31
<211> LENGTH: 207
<212> TYPE: DNA
<213> ORGANISM: Staphylococcus epidermidis
<220> FEATURE:
<221> NAME/KEY: CDS
<222> LOCATION: (1)..(207)

<400> SEQUENCE: 31 atg att tca gtg ata ctg ccg atg gaa gaa ata att att gca ata ata      48
Met Ile Ser Val Ile Leu Pro Met Glu Glu Ile Ile Ile Ala Ile Ile
1               5                  10                  15 aat aac gac tta ggc cat tta att ttt gag aat aaa aaa aat agt ggg      96
Asn Asn Asp Leu Gly His Leu Ile Phe Glu Asn Lys Lys Asn Ser Gly
             20                  25                  30 ttt tct ttt ttc ata ata aaa cct ttc ata act aat att tat ttt cta    144
Phe Ser Phe Phe Ile Ile Lys Pro Phe Ile Thr Asn Ile Tyr Phe Leu
         35                  40                  45 tca ggt att aaa aaa att tta caa aaa cag aga aaa tat tat acg atg    192
Ser Gly Ile Lys Lys Ile Leu Gln Lys Gln Arg Lys Tyr Tyr Thr Met
     50                  55                  60 cta ata aaa gta taa                                                 207
Leu Ile Lys Val
65

<210> SEQ ID NO 32
<211> LENGTH: 68
<212> TYPE: PRT
<213> ORGANISM: Staphylococcus epidermidis

<400> SEQUENCE: 32

Met Ile Ser Val Ile Leu Pro Met Glu Glu Ile Ile Ile Ala Ile Ile
1               5                  10                  15

Asn Asn Asp Leu Gly His Leu Ile Phe Glu Asn Lys Lys Asn Ser Gly
             20                  25                  30

Phe Ser Phe Phe Ile Ile Lys Pro Phe Ile Thr Asn Ile Tyr Phe Leu
         35                  40                  45

Ser Gly Ile Lys Lys Ile Leu Gln Lys Gln Arg Lys Tyr Tyr Thr Met
     50                  55                  60

Leu Ile Lys Val
65

<210> SEQ ID NO 33
<211> LENGTH: 210
<212> TYPE: DNA
<213> ORGANISM: Staphylococcus epidermidis
<220> FEATURE:
<221> NAME/KEY: CDS
<222> LOCATION: (1)..(210)

<400> SEQUENCE: 33 atg aac ata tac tta aaa gta att tta act tct tta ttt ttt gct tta      48
Met Asn Ile Tyr Leu Lys Val Ile Leu Thr Ser Leu Phe Phe Ala Leu
1               5                  10                  15
```

```
ata att ttt att gta act tat ata acg act aag caa tgg gga aca tcg      96
Ile Ile Phe Ile Val Thr Tyr Ile Thr Thr Lys Gln Trp Gly Thr Ser
            20                  25                  30 tta ggt ttt tca tct tta tca ttt atc ggt aac ttt att tac gat tat     144
Leu Gly Phe Ser Ser Leu Ser Phe Ile Gly Asn Phe Ile Tyr Asp Tyr
        35                  40                  45 tca acg aaa tta agt gat aaa aaa tat gaa aaa aga ata aat agc aac     192
Ser Thr Lys Leu Ser Asp Lys Lys Tyr Glu Lys Arg Ile Asn Ser Asn
50                  55                  60 aaa aaa gat aaa ctt tag                                             210
Lys Lys Asp Lys Leu
65

<210> SEQ ID NO 34
<211> LENGTH: 69
<212> TYPE: PRT
<213> ORGANISM: Staphylococcus epidermidis

<400> SEQUENCE: 34

Met Asn Ile Tyr Leu Lys Val Ile Leu Thr Ser Leu Phe Phe Ala Leu
1               5                   10                  15

Ile Ile Phe Ile Val Thr Tyr Ile Thr Thr Lys Gln Trp Gly Thr Ser
            20                  25                  30

Leu Gly Phe Ser Ser Leu Ser Phe Ile Gly Asn Phe Ile Tyr Asp Tyr
        35                  40                  45

Ser Thr Lys Leu Ser Asp Lys Lys Tyr Glu Lys Arg Ile Asn Ser Asn
50                  55                  60

Lys Lys Asp Lys Leu
65

<210> SEQ ID NO 35
<211> LENGTH: 183
<212> TYPE: DNA
<213> ORGANISM: Staphylococcus epidermidis
<220> FEATURE:
<221> NAME/KEY: CDS
<222> LOCATION: (1)..(183)

<400> SEQUENCE: 35 atg aaa aat aac aaa aat tta ttt gat tta gaa att aaa aaa gaa aca      48
Met Lys Asn Asn Lys Asn Leu Phe Asp Leu Glu Ile Lys Lys Glu Thr
1               5                   10                  15 agt caa aac act gat gaa ctt gaa cct caa act gct gga cca gcg att      96
Ser Gln Asn Thr Asp Glu Leu Glu Pro Gln Thr Ala Gly Pro Ala Ile
            20                  25                  30 aga gct tct gtg aaa caa tgt cag aaa act ttg aaa gct acg cgt tta     144
Arg Ala Ser Val Lys Gln Cys Gln Lys Thr Leu Lys Ala Thr Arg Leu
        35                  40                  45 ttt aca gtg tct tgc aaa gga aaa aac gga tgt aaa tag                 183
Phe Thr Val Ser Cys Lys Gly Lys Asn Gly Cys Lys
50                  55                  60

<210> SEQ ID NO 36
<211> LENGTH: 60
<212> TYPE: PRT
<213> ORGANISM: Staphylococcus epidermidis

<400> SEQUENCE: 36

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30
```

```
Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
        50                  55                  60

<210> SEQ ID NO 37
<211> LENGTH: 171
<212> TYPE: DNA
<213> ORGANISM: Staphylococcus hominis
<220> FEATURE:
<221> NAME/KEY: CDS
<222> LOCATION: (1)..(171)

<400> SEQUENCE: 37 atg gaa aac aaa aaa gat tta ttt gat tta gaa atc aaa aaa gat aat      48
Met Glu Asn Lys Lys Asp Leu Phe Asp Leu Glu Ile Lys Lys Asp Asn
1               5                  10                  15 atg gaa aat aat aat gaa tta gaa gct caa tct ctt ggt cct gca att      96
Met Glu Asn Asn Asn Glu Leu Glu Ala Gln Ser Leu Gly Pro Ala Ile
            20                  25                  30 aag gca act aga cag gta tgt cct aaa gca aca cgt ttt gtt aca gtt     144
Lys Ala Thr Arg Gln Val Cys Pro Lys Ala Thr Arg Phe Val Thr Val
        35                  40                  45 tct tgt aaa aaa agt gat tgt caa tag                                 171
Ser Cys Lys Lys Ser Asp Cys Gln
        50                  55

<210> SEQ ID NO 38
<211> LENGTH: 56
<212> TYPE: PRT
<213> ORGANISM: Staphylococcus hominis

<400> SEQUENCE: 38

Met Glu Asn Lys Lys Asp Leu Phe Asp Leu Glu Ile Lys Lys Asp Asn
1               5                  10                  15

Met Glu Asn Asn Asn Glu Leu Glu Ala Gln Ser Leu Gly Pro Ala Ile
            20                  25                  30

Lys Ala Thr Arg Gln Val Cys Pro Lys Ala Thr Arg Phe Val Thr Val
        35                  40                  45

Ser Cys Lys Lys Ser Asp Cys Gln
        50                  55

<210> SEQ ID NO 39
<211> LENGTH: 135
<212> TYPE: DNA
<213> ORGANISM: Staphylococcus hominis
<220> FEATURE:
<221> NAME/KEY: CDS
<222> LOCATION: (1)..(135)

<400> SEQUENCE: 39 atg aaa gtt gtt aaa gaa aag aaa gaa ctt ttt gat ctt gac gtt aaa      48
Met Lys Val Val Lys Glu Lys Lys Glu Leu Phe Asp Leu Asp Val Lys
1               5                  10                  15 gta aat gcg aga gac atg aat aat tca gaa tca ggt cca cct aat aca      96
Val Asn Ala Arg Asp Met Asn Asn Ser Glu Ser Gly Pro Pro Asn Thr
            20                  25                  30 agt tta ata tgg tgt acg gat gga tgc gct aaa cgg taa                 135
Ser Leu Ile Trp Cys Thr Asp Gly Cys Ala Lys Arg
        35                  40

<210> SEQ ID NO 40
```

```
<211> LENGTH: 44
<212> TYPE: PRT
<213> ORGANISM: Staphylococcus hominis

<400> SEQUENCE: 40

Met Lys Val Val Lys Glu Lys Glu Leu Phe Asp Leu Asp Val Lys
1               5                   10                  15

Val Asn Ala Arg Asp Met Asn Asn Ser Glu Ser Gly Pro Pro Asn Thr
                20                  25                  30

Ser Leu Ile Trp Cys Thr Asp Gly Cys Ala Lys Arg
            35                  40

<210> SEQ ID NO 41
<211> LENGTH: 138
<212> TYPE: DNA
<213> ORGANISM: Staphylococcus hominis
<220> FEATURE:
<221> NAME/KEY: CDS
<222> LOCATION: (1)..(138)

<400> SEQUENCE: 41 atg gat att ata aaa gta aat aaa aca gaa aga atg aat gat aat aga      48
Met Asp Ile Ile Lys Val Asn Lys Thr Glu Arg Met Asn Asp Asn Arg
1               5                   10                  15 aaa att gta atg att ttt tct tta tac gat aca ttt ttt aac gct act      96
Lys Ile Val Met Ile Phe Ser Leu Tyr Asp Thr Phe Phe Asn Ala Thr
                20                  25                  30 aat aca cat aag cta aag agt atg aag ctt aat gcg aaa taa             138
Asn Thr His Lys Leu Lys Ser Met Lys Leu Asn Ala Lys
            35                  40                  45

<210> SEQ ID NO 42
<211> LENGTH: 45
<212> TYPE: PRT
<213> ORGANISM: Staphylococcus hominis

<400> SEQUENCE: 42

Met Asp Ile Ile Lys Val Asn Lys Thr Glu Arg Met Asn Asp Asn Arg
1               5                   10                  15

Lys Ile Val Met Ile Phe Ser Leu Tyr Asp Thr Phe Phe Asn Ala Thr
                20                  25                  30

Asn Thr His Lys Leu Lys Ser Met Lys Leu Asn Ala Lys
            35                  40                  45

<210> SEQ ID NO 43
<211> LENGTH: 201
<212> TYPE: DNA
<213> ORGANISM: Staphylococcus hominis
<220> FEATURE:
<221> NAME/KEY: CDS
<222> LOCATION: (1)..(201)

<400> SEQUENCE: 43 atg agt aat aaa gat tta gaa tta ttt aat aca gcc ggt gat tta ata      48
Met Ser Asn Lys Asp Leu Glu Leu Phe Asn Thr Ala Gly Asp Leu Ile
1               5                   10                  15 caa gaa tta aaa gat ggt gac cta aat atc cat tta tat ggt gaa tcg      96
Gln Glu Leu Lys Asp Gly Asp Leu Asn Ile His Leu Tyr Gly Glu Ser
                20                  25                  30 gaa att aga aaa aaa tct ttc tct caa aaa aca ggg aat gat ggg aaa     144
Glu Ile Arg Lys Lys Ser Phe Ser Gln Lys Thr Gly Asn Asp Gly Lys
            35                  40                  45 cat tgt aca att act tgg gaa tgt tct ata tgt cct act aaa act tgt     192
His Cys Thr Ile Thr Trp Glu Cys Ser Ile Cys Pro Thr Lys Thr Cys
```

```
His Cys Thr Ile Thr Trp Glu Cys Ser Ile Cys Pro Thr Lys Thr Cys
     50                  55                  60 tgg tgc taa                                                                201
Trp Cys
65

<210> SEQ ID NO 44
<211> LENGTH: 66
<212> TYPE: PRT
<213> ORGANISM: Staphylococcus hominis

<400> SEQUENCE: 44

Met Ser Asn Lys Asp Leu Glu Leu Phe Asn Thr Ala Gly Asp Leu Ile
1               5                   10                  15

Gln Glu Leu Lys Asp Gly Asp Leu Asn Ile His Leu Tyr Gly Glu Ser
            20                  25                  30

Glu Ile Arg Lys Lys Ser Phe Ser Gln Lys Thr Gly Asn Asp Gly Lys
        35                  40                  45

His Cys Thr Ile Thr Trp Glu Cys Ser Ile Cys Pro Thr Lys Thr Cys
     50                  55                  60

Trp Cys
65

<210> SEQ ID NO 45
<211> LENGTH: 117
<212> TYPE: DNA
<213> ORGANISM: Staphylococcus hominis
<220> FEATURE:
<221> NAME/KEY: CDS
<222> LOCATION: (1)..(117)

<400> SEQUENCE: 45 atg gga act tca gag gta aga aaa gga aaa gga ggc ggt ttt agt acc         48
Met Gly Thr Ser Glu Val Arg Lys Gly Lys Gly Gly Gly Phe Ser Thr
1               5                   10                  15 gta acc gtt gta aca cca att gta ccg aca tcg aag tgt gcc tca att         96
Val Thr Val Val Thr Pro Ile Val Pro Thr Ser Lys Cys Ala Ser Ile
            20                  25                  30 gta aaa cca tgt aac aaa taa                                             117
Val Lys Pro Cys Asn Lys
            35

<210> SEQ ID NO 46
<211> LENGTH: 38
<212> TYPE: PRT
<213> ORGANISM: Staphylococcus hominis

<400> SEQUENCE: 46

Met Gly Thr Ser Glu Val Arg Lys Gly Lys Gly Gly Gly Phe Ser Thr
1               5                   10                  15

Val Thr Val Val Thr Pro Ile Val Pro Thr Ser Lys Cys Ala Ser Ile
            20                  25                  30

Val Lys Pro Cys Asn Lys
            35

<210> SEQ ID NO 47
<211> LENGTH: 165
<212> TYPE: DNA
<213> ORGANISM: Staphylococcus hominis
<220> FEATURE:
<221> NAME/KEY: CDS
<222> LOCATION: (1)..(165)
```

```
<400> SEQUENCE: 47 atg act aaa ata act aaa gat gat ttg aaa aag att aca gaa aat cgt         48
Met Thr Lys Ile Thr Lys Asp Asp Leu Lys Lys Ile Thr Glu Asn Arg
1               5                   10                  15 att gaa gca cgt aca cat cca acc gtt gtt cct gta agt gct gct gta         96
Ile Glu Ala Arg Thr His Pro Thr Val Val Pro Val Ser Ala Ala Val
                20                  25                  30 tgc gga gtt gct act aaa tta gta cca aca tcg aaa tgt gct tca att        144
Cys Gly Val Ala Thr Lys Leu Val Pro Thr Ser Lys Cys Ala Ser Ile
        35                  40                  45 gta aaa cca tgt aat aaa taa                                            165
Val Lys Pro Cys Asn Lys
    50

<210> SEQ ID NO 48
<211> LENGTH: 54
<212> TYPE: PRT
<213> ORGANISM: Staphylococcus hominis

<400> SEQUENCE: 48

Met Thr Lys Ile Thr Lys Asp Asp Leu Lys Lys Ile Thr Glu Asn Arg
1               5                   10                  15

Ile Glu Ala Arg Thr His Pro Thr Val Val Pro Val Ser Ala Ala Val
                20                  25                  30

Cys Gly Val Ala Thr Lys Leu Val Pro Thr Ser Lys Cys Ala Ser Ile
        35                  40                  45

Val Lys Pro Cys Asn Lys
    50

<210> SEQ ID NO 49
<211> LENGTH: 522
<212> TYPE: DNA
<213> ORGANISM: Staphylococcus hominis
<220> FEATURE:
<221> NAME/KEY: CDS
<222> LOCATION: (1)..(522)

<400> SEQUENCE: 49 atg act ata gat tta gta atg ata ctt att att ttg atg tat atg ata         48
Met Thr Ile Asp Leu Val Met Ile Leu Ile Ile Leu Met Tyr Met Ile
1               5                   10                  15 att ggt ttt aga aga ggc ctt tgg ctg aat agt ctt cat ttg tcg tct         96
Ile Gly Phe Arg Arg Gly Leu Trp Leu Asn Ser Leu His Leu Ser Ser
                20                  25                  30 aca ctt gtc tca cta ttc att gcg cat cgt ttt tac caa tat ata tca        144
Thr Leu Val Ser Leu Phe Ile Ala His Arg Phe Tyr Gln Tyr Ile Ser
        35                  40                  45 aaa caa atg att gtt ttt gtt cca ttt cct aaa aca gtt gct ttt gac        192
Lys Gln Met Ile Val Phe Val Pro Phe Pro Lys Thr Val Ala Phe Asp
    50                  55                  60 acg cac ttc gca ttt caa tac cat gat gta caa caa cgt ttt gat act        240
Thr His Phe Ala Phe Gln Tyr His Asp Val Gln Gln Arg Phe Asp Thr
65                  70                  75                  80 att gtg gca ttt tta tgt att gct ttt ata agt aag ttg ctt tta tat        288
Ile Val Ala Phe Leu Cys Ile Ala Phe Ile Ser Lys Leu Leu Leu Tyr
                85                  90                  95 ctt att att gta act ttt gat aat ata gtg tca tat cat aat att cat        336
Leu Ile Ile Val Thr Phe Asp Asn Ile Val Ser Tyr His Asn Ile His
                100                 105                 110 gtt aca agt cga ata ttg gga agc gta tta ggt agt att gca agt gtg        384
Val Thr Ser Arg Ile Leu Gly Ser Val Leu Gly Ser Ile Ala Ser Val
```

```
              115                 120                 125
att gta ctg caa ctt gtt tta tat tta gta tct tta tat cct aat gaa    432
Ile Val Leu Gln Leu Val Leu Tyr Leu Val Ser Leu Tyr Pro Asn Glu
    130                 135                 140 tgg att caa gaa agt tta aaa tac ggt tat tta agc cat att att cta    480
Trp Ile Gln Glu Ser Leu Lys Tyr Gly Tyr Leu Ser His Ile Ile Leu
145                 150                 155                 160 ttt aag atg ccg ttt tta tca tct tat ata cta aat tta taa            522
Phe Lys Met Pro Phe Leu Ser Ser Tyr Ile Leu Asn Leu
                165                 170

<210> SEQ ID NO 50
<211> LENGTH: 173
<212> TYPE: PRT
<213> ORGANISM: Staphylococcus hominis

<400> SEQUENCE: 50

Met Thr Ile Asp Leu Val Met Ile Leu Ile Leu Met Tyr Met Ile
1               5                   10                  15

Ile Gly Phe Arg Arg Gly Leu Trp Leu Asn Ser Leu His Leu Ser Ser
                20                  25                  30

Thr Leu Val Ser Leu Phe Ile Ala His Arg Phe Tyr Gln Tyr Ile Ser
            35                  40                  45

Lys Gln Met Ile Val Phe Val Pro Phe Pro Lys Thr Val Ala Phe Asp
    50                  55                  60

Thr His Phe Ala Phe Gln Tyr His Asp Val Gln Gln Arg Phe Asp Thr
65                  70                  75                  80

Ile Val Ala Phe Leu Cys Ile Ala Phe Ile Ser Lys Leu Leu Leu Tyr
                85                  90                  95

Leu Ile Ile Val Thr Phe Asp Asn Ile Val Ser Tyr His Asn Ile His
            100                 105                 110

Val Thr Ser Arg Ile Leu Gly Ser Val Leu Gly Ser Ile Ala Ser Val
    115                 120                 125

Ile Val Leu Gln Leu Val Leu Tyr Leu Val Ser Leu Tyr Pro Asn Glu
130                 135                 140

Trp Ile Gln Glu Ser Leu Lys Tyr Gly Tyr Leu Ser His Ile Ile Leu
145                 150                 155                 160

Phe Lys Met Pro Phe Leu Ser Ser Tyr Ile Leu Asn Leu
                165                 170

<210> SEQ ID NO 51
<211> LENGTH: 522
<212> TYPE: DNA
<213> ORGANISM: Staphylococcus epidermidis
<220> FEATURE:
<221> NAME/KEY: CDS
<222> LOCATION: (1)..(522)

<400> SEQUENCE: 51 atg ctc att gat ata gtt gtt ctt ctt att att tgt tac ttt ata gtg    48
Met Leu Ile Asp Ile Val Val Leu Leu Ile Ile Cys Tyr Phe Ile Val
1               5                   10                  15 ata ggg ttt cgt aga ggt att tgg tta tcg ata ttg cac ttt gct tct    96
Ile Gly Phe Arg Arg Gly Ile Trp Leu Ser Ile Leu His Phe Ala Ser
                20                  25                  30 tca att gta tct tta tat att gcg tca caa cat tat caa tcg att gcg    144
Ser Ile Val Ser Leu Tyr Ile Ala Ser Gln His Tyr Gln Ser Ile Ala
            35                  40                  45 caa cgt tta gtt gta ttt gtg cca ttt ccg aaa acg gtg gcg ttt gat    192
```

```
                                                                              240
atg gtc tat act ata cct tat gat cat ttg caa tac aga ttt gaa aaa
Met Val Tyr Thr Ile Pro Tyr Asp His Leu Gln Tyr Arg Phe Glu Lys
 65                  70                  75                  80 gtg ata gca ttt att ata ata ttt ggt atg tgt aag ctt att ttg tat    288
Val Ile Ala Phe Ile Ile Ile Phe Gly Met Cys Lys Leu Ile Leu Tyr
                 85                  90                  95 cta gtt gtt gtt aca ttt gat aat ata ata acg tat aaa aag ata cat    336
Leu Val Val Val Thr Phe Asp Asn Ile Ile Thr Tyr Lys Lys Ile His
            100                 105                 110 tta gta agt cgg ata tcg agt gtc gtt ttg agt atc ata tcg gtt ttt    384
Leu Val Ser Arg Ile Ser Ser Val Val Leu Ser Ile Ile Ser Val Phe
        115                 120                 125 ata tat tta caa att gga ctt tat tta tta tcg cta tat ccg cat tca    432
Ile Tyr Leu Gln Ile Gly Leu Tyr Leu Leu Ser Leu Tyr Pro His Ser
    130                 135                 140 ttt ata cag tac caa tta tct caa tcg cta gta agt cga gtt gtg att    480
Phe Ile Gln Tyr Gln Leu Ser Gln Ser Leu Val Ser Arg Val Val Ile
145                 150                 155                 160 gaa caa att cct tat tta tca caa ttt att tta aat tta taa            522
Glu Gln Ile Pro Tyr Leu Ser Gln Phe Ile Leu Asn Leu
                165                 170
```

<210> SEQ ID NO 52
<211> LENGTH: 173
<212> TYPE: PRT
<213> ORGANISM: Staphylococcus epidermidis

<400> SEQUENCE: 52

```
Met Leu Ile Asp Ile Val Val Leu Leu Ile Cys Tyr Phe Ile Val
 1               5                  10                  15

Ile Gly Phe Arg Arg Gly Ile Trp Leu Ser Ile Leu His Phe Ala Ser
                 20                  25                  30

Ser Ile Val Ser Leu Tyr Ile Ala Ser Gln His Tyr Gln Ser Ile Ala
            35                  40                  45

Gln Arg Leu Val Val Phe Val Pro Phe Pro Lys Thr Val Ala Phe Asp
        50                  55                  60

Met Val Tyr Thr Ile Pro Tyr Asp His Leu Gln Tyr Arg Phe Glu Lys
 65                  70                  75                  80

Val Ile Ala Phe Ile Ile Ile Phe Gly Met Cys Lys Leu Ile Leu Tyr
                 85                  90                  95

Leu Val Val Val Thr Phe Asp Asn Ile Ile Thr Tyr Lys Lys Ile His
            100                 105                 110

Leu Val Ser Arg Ile Ser Ser Val Val Leu Ser Ile Ile Ser Val Phe
        115                 120                 125

Ile Tyr Leu Gln Ile Gly Leu Tyr Leu Leu Ser Leu Tyr Pro His Ser
    130                 135                 140

Phe Ile Gln Tyr Gln Leu Ser Gln Ser Leu Val Ser Arg Val Val Ile
145                 150                 155                 160

Glu Gln Ile Pro Tyr Leu Ser Gln Phe Ile Leu Asn Leu
                165                 170
```

<210> SEQ ID NO 53
<211> LENGTH: 1260
<212> TYPE: DNA
<213> ORGANISM: Staphylococcus epidermidis
<220> FEATURE:
<221> NAME/KEY: CDS

<222> LOCATION: (1)..(1260)

<400> SEQUENCE: 53

| | | | | | | | | | | | | | | | | |
|---|---|---|---|---|---|---|---|---|---|---|---|---|---|---|---|---|
| atg | att | ggt | aga | aaa | aaa | gaa | acc | ctt | tta | aaa | aac | gaa | gtt | att | tct | 48 |
| Met | Ile | Gly | Arg | Lys | Lys | Glu | Thr | Leu | Leu | Lys | Asn | Glu | Val | Ile | Ser | |
| 1 | | | | 5 | | | | | 10 | | | | | 15 | | |
| gcg | ttt | act | act | ttt | ttt | acc | tgc | agt | tat | ata | ata | gtt | aat | ggt | | 96 |
| Ala | Phe | Thr | Thr | Phe | Phe | Thr | Cys | Ser | Tyr | Ile | Ile | Val | Asn | Gly | | |
| | | | 20 | | | | | 25 | | | | | 30 | | | |
| ata | ttg | tta | cat | caa | gca | gga | atg | tct | ttg | tta | tgg | acg | att | ata | gct | 144 |
| Ile | Leu | Leu | His | Gln | Ala | Gly | Met | Ser | Leu | Leu | Trp | Thr | Ile | Ile | Ala | |
| | | | 35 | | | | 40 | | | | | 45 | | | | |
| act | act | cta | gtt | tgt | tgc | att | agt | tgc | atc | ctt | ctt | ggt | ata | tat | gct | 192 |
| Thr | Thr | Leu | Val | Cys | Cys | Ile | Ser | Cys | Ile | Leu | Leu | Gly | Ile | Tyr | Ala | |
| | 50 | | | | | 55 | | | | | 60 | | | | | |
| aat | gtt | cca | cta | att | att | ata | cca | gga | atc | ggt | gaa | act | att | ttt | ttt | 240 |
| Asn | Val | Pro | Leu | Ile | Ile | Ile | Pro | Gly | Ile | Gly | Glu | Thr | Ile | Phe | Phe | |
| 65 | | | | | 70 | | | | | 75 | | | | | 80 | |
| act | tat | aca | atc | att | aaa | agt | cat | tac | tat | aat | tat | cat | gaa | gcg | cta | 288 |
| Thr | Tyr | Thr | Ile | Ile | Lys | Ser | His | Tyr | Tyr | Asn | Tyr | His | Glu | Ala | Leu | |
| | | | | 85 | | | | | 90 | | | | | 95 | | |
| gct | att | gtt | ttg | att | tca | ggt | ttg | att | ttc | act | ttt | att | gca | tac | aca | 336 |
| Ala | Ile | Val | Leu | Ile | Ser | Gly | Leu | Ile | Phe | Thr | Phe | Ile | Ala | Tyr | Thr | |
| | | | 100 | | | | | 105 | | | | | 110 | | | |
| ccg | ttt | gct | aga | gtt | cta | gac | aag | tcc | ata | cca | aag | aat | tta | aaa | gaa | 384 |
| Pro | Phe | Ala | Arg | Val | Leu | Asp | Lys | Ser | Ile | Pro | Lys | Asn | Leu | Lys | Glu | |
| | | | | 115 | | | | | 120 | | | | | 125 | | |
| gga | ata | act | att | ggt | ata | ggt | ctg | ttt | atg | gcg | ttt | gtt | gga | cta | caa | 432 |
| Gly | Ile | Thr | Ile | Gly | Ile | Gly | Leu | Phe | Met | Ala | Phe | Val | Gly | Leu | Gln | |
| | 130 | | | | | 135 | | | | | 140 | | | | | |
| aac | agc | aaa | ata | att | ata | cca | aac | agg | caa | agt | att | gtt | gag | cta | aac | 480 |
| Asn | Ser | Lys | Ile | Ile | Ile | Pro | Asn | Arg | Gln | Ser | Ile | Val | Glu | Leu | Asn | |
| 145 | | | | | 150 | | | | | 155 | | | | | 160 | |
| cac | ata | aac | att | tat | agt | ggg | tta | gcg | ata | cta | cta | cta | tta | ttt | gca | 528 |
| His | Ile | Asn | Ile | Tyr | Ser | Gly | Leu | Ala | Ile | Leu | Leu | Leu | Leu | Phe | Ala | |
| | | | | 165 | | | | | 170 | | | | | 175 | | |
| att | gtt | ata | ttt | act | tta | ggg | acc | aag | ttg | gct | ttc | ttt | tat | aca | gta | 576 |
| Ile | Val | Ile | Phe | Thr | Leu | Gly | Thr | Lys | Leu | Ala | Phe | Phe | Tyr | Thr | Val | |
| | | | 180 | | | | | 185 | | | | | 190 | | | |
| att | att | ggt | atc | att | ata | tct | ttt | tta | gct | ggg | att | ata | aag | gtg | aaa | 624 |
| Ile | Ile | Gly | Ile | Ile | Ile | Ser | Phe | Leu | Ala | Gly | Ile | Ile | Lys | Val | Lys | |
| | | | | 195 | | | | | 200 | | | | | 205 | | |
| tat | cat | ttt | tat | aat | ttt | agt | ttg | cga | tca | ata | gta | agc | gag | aat | aat | 672 |
| Tyr | His | Phe | Tyr | Asn | Phe | Ser | Leu | Arg | Ser | Ile | Val | Ser | Glu | Asn | Asn | |
| | 210 | | | | | 215 | | | | | 220 | | | | | |
| att | ttt | agt | tac | agt | ttt | gat | aaa | ata | ggt | cat | ttt | tct | ttt | tgg | tct | 720 |
| Ile | Phe | Ser | Tyr | Ser | Phe | Asp | Lys | Ile | Gly | His | Phe | Ser | Phe | Trp | Ser | |
| 225 | | | | | 230 | | | | | 235 | | | | | 240 | |
| tta | gtg | ttc | tca | ctt | act | att | ttg | tta | ctg | ttt | caa | aat | tta | ggt | aca | 768 |
| Leu | Val | Phe | Ser | Leu | Thr | Ile | Leu | Leu | Leu | Phe | Gln | Asn | Leu | Gly | Thr | |
| | | | | 245 | | | | | 250 | | | | | 255 | | |
| tta | cat | gga | ttg | aaa | att | aat | gat | aaa | gta | aaa | ttg | tca | aga | att | ttt | 816 |
| Leu | His | Gly | Leu | Lys | Ile | Asn | Asp | Lys | Val | Lys | Leu | Ser | Arg | Ile | Phe | |
| | | | 260 | | | | | 265 | | | | | 270 | | | |
| aaa | atg | gtc | ggt | att | act | aac | ata | att | tca | agc | tta | ttt | ggt | gtg | agt | 864 |
| Lys | Met | Val | Gly | Ile | Thr | Asn | Ile | Ile | Ser | Ser | Leu | Phe | Gly | Val | Ser | |
| | | 275 | | | | | 280 | | | | | 285 | | | | |
| tct | aca | gtt | att | gca | gtc | gaa | agt | tct | act | gca | act | cat | tca | gga | gct | 912 |
| Ser | Thr | Val | Ile | Ala | Val | Glu | Ser | Ser | Thr | Ala | Thr | His | Ser | Gly | Ala | |
| | | | 290 | | | | | 295 | | | | | 300 | | | |

```
aaa aca gga aaa gta tct att ttt gta ggt ata atg ttt ctt tta tct    960
Lys Thr Gly Lys Val Ser Ile Phe Val Gly Ile Met Phe Leu Leu Ser
305                 310                 315                 320 ttg tta ata atg ccc gtt att ata gca ata cct agt tta gtt gta tca   1008
Leu Leu Ile Met Pro Val Ile Ile Ala Ile Pro Ser Leu Val Val Ser
            325                 330                 335 cct atc tta ata att gtt ggc ggt tta atg ttt act aat att aaa gaa   1056
Pro Ile Leu Ile Ile Val Gly Gly Leu Met Phe Thr Asn Ile Lys Glu
        340                 345                 350 tta gat ttt aat gat atg act gaa ttt att cct tgt tat ata aca att   1104
Leu Asp Phe Asn Asp Met Thr Glu Phe Ile Pro Cys Tyr Ile Thr Ile
    355                 360                 365 ata atg ata cca ctt act ttt gat att gca act gga atg gga ttt gga   1152
Ile Met Ile Pro Leu Thr Phe Asp Ile Ala Thr Gly Met Gly Phe Gly
370                 375                 380 ttt att tca tat gtt cta att aat ttt gta tgc aaa aaa acc gaa cgt   1200
Phe Ile Ser Tyr Val Leu Ile Asn Phe Val Cys Lys Lys Thr Glu Arg
385                 390                 395                 400 tta aat cca att tta ata att att gct tta ctt ttt aca ata aat tta   1248
Leu Asn Pro Ile Leu Ile Ile Ala Leu Leu Phe Thr Ile Asn Leu
            405                 410                 415 gtt tta caa taa                                                   1260
Val Leu Gln <210> SEQ ID NO 54
<211> LENGTH: 419
<212> TYPE: PRT
<213> ORGANISM: Staphylococcus epidermidis

<400> SEQUENCE: 54

Met Ile Gly Arg Lys Lys Glu Thr Leu Leu Lys Asn Glu Val Ile Ser
1               5                   10                  15

Ala Phe Thr Thr Phe Thr Cys Ser Tyr Ile Ile Val Asn Gly
            20                  25                  30

Ile Leu Leu His Gln Ala Gly Met Ser Leu Leu Trp Thr Ile Ile Ala
        35                  40                  45

Thr Thr Leu Val Cys Cys Ile Ser Cys Ile Leu Gly Ile Tyr Ala
    50                  55                  60

Asn Val Pro Leu Ile Ile Pro Gly Ile Gly Glu Thr Ile Phe Phe
65                  70                  75                  80

Thr Tyr Thr Ile Ile Lys Ser His Tyr Tyr Asn Tyr His Glu Ala Leu
                85                  90                  95

Ala Ile Val Leu Ile Ser Gly Leu Ile Phe Thr Phe Ile Ala Tyr Thr
            100                 105                 110

Pro Phe Ala Arg Val Leu Asp Lys Ser Ile Pro Lys Asn Leu Lys Glu
        115                 120                 125

Gly Ile Thr Ile Gly Ile Gly Leu Phe Met Ala Phe Val Gly Leu Gln
130                 135                 140

Asn Ser Lys Ile Ile Ile Pro Asn Arg Gln Ser Ile Val Glu Leu Asn
145                 150                 155                 160

His Ile Asn Ile Tyr Ser Gly Leu Ala Ile Leu Leu Leu Phe Ala
                165                 170                 175

Ile Val Ile Phe Thr Leu Gly Thr Lys Leu Ala Phe Phe Tyr Thr Val
            180                 185                 190

Ile Ile Gly Ile Ile Ile Ser Phe Leu Ala Gly Ile Ile Lys Val Lys
        195                 200                 205
```

-continued

```
Tyr His Phe Tyr Asn Phe Ser Leu Arg Ser Ile Val Ser Glu Asn Asn
            210                 215                 220

Ile Phe Ser Tyr Ser Phe Asp Lys Ile Gly His Phe Ser Phe Trp Ser
225                 230                 235                 240

Leu Val Phe Ser Leu Thr Ile Leu Leu Phe Gln Asn Leu Gly Thr
            245                 250                 255

Leu His Gly Leu Lys Ile Asn Asp Lys Val Lys Leu Ser Arg Ile Phe
            260                 265                 270

Lys Met Val Gly Ile Thr Asn Ile Ser Ser Leu Phe Gly Val Ser
            275                 280                 285

Ser Thr Val Ile Ala Val Glu Ser Ser Thr Ala Thr His Ser Gly Ala
290                 295                 300

Lys Thr Gly Lys Val Ser Ile Phe Val Gly Ile Met Phe Leu Leu Ser
305                 310                 315                 320

Leu Leu Ile Met Pro Val Ile Ala Ile Pro Ser Leu Val Val Ser
            325                 330                 335

Pro Ile Leu Ile Ile Val Gly Gly Leu Met Phe Thr Asn Ile Lys Glu
            340                 345                 350

Leu Asp Phe Asn Asp Met Thr Glu Phe Ile Pro Cys Tyr Ile Thr Ile
            355                 360                 365

Ile Met Ile Pro Leu Thr Phe Asp Ile Ala Thr Gly Met Gly Phe Gly
370                 375                 380

Phe Ile Ser Tyr Val Leu Ile Asn Phe Val Cys Lys Lys Thr Glu Arg
385                 390                 395                 400

Leu Asn Pro Ile Leu Ile Ile Ala Leu Leu Phe Thr Ile Asn Leu
            405                 410                 415

Val Leu Gln

<210> SEQ ID NO 55
<211> LENGTH: 10
<212> TYPE: PRT
<213> ORGANISM: Staphylococcus epidermidis
<220> FEATURE:
<221> NAME/KEY: MISC_FEATURE
<222> LOCATION: (10)..(10)
<223> OTHER INFORMATION: Xaa at 10 is V or L

<400> SEQUENCE: 55

Lys Asn Gly Ala Tyr Lys Ala Gln Gly Xaa
1               5                   10

<210> SEQ ID NO 56
<211> LENGTH: 30
<212> TYPE: PRT
<213> ORGANISM: Artificial Sequence
<220> FEATURE:
<223> OTHER INFORMATION: Staphylococcus hominis Hogocidin peptide

<400> SEQUENCE: 56

Lys Cys Ser Trp Trp Asn Ala Ser Cys His Leu Gly Asn Asn Gly Lys
1               5                   10                  15

Ile Cys Thr Val Ser His Glu Cys Ala Ala Gly Cys Asn Leu
            20                  25                  30

<210> SEQ ID NO 57
<211> LENGTH: 38
<212> TYPE: PRT
<213> ORGANISM: Artificial Sequence
<220> FEATURE:
<223> OTHER INFORMATION: Staphylococcus hominis Hogocidin peptide
```

```
<400> SEQUENCE: 57

Ala Thr Pro Thr Ile Thr Thr Ser Ser Ala Thr Cys Gly Gly Ile Ile
1               5                   10                  15

Val Ala Ala Ser Ala Ala Gln Cys Pro Thr Leu Ala Cys Ser Ser Arg
            20                  25                  30

Cys Gly Lys Arg Lys Lys
            35
```